US008703121B2

(12) United States Patent
Harris et al.

(10) Patent No.: US 8,703,121 B2
(45) Date of Patent: Apr. 22, 2014

(54) POSTPARTUM-DERIVED CELLS FOR USE IN TREATMENT OF DISEASE OF THE HEART AND CIRCULATORY SYSTEM

(75) Inventors: Ian Ross Harris, Belle Mead, NJ (US); Alexander M. Harmon, Clinton, NJ (US); Anthony J. Kihm, Princeton, NJ (US); Anna Gosiewska, Skillman, NJ (US)

(73) Assignee: DePuy Synthes Products, LLC, Raynham, MA (US)

( * ) Notice: Subject to any disclaimer, the term of this patent is extended or adjusted under 35 U.S.C. 154(b) by 696 days.

(21) Appl. No.: 10/877,445

(22) Filed: Jun. 25, 2004

(65) Prior Publication Data

US 2005/0058630 A1 Mar. 17, 2005

Related U.S. Application Data

(60) Provisional application No. 60/483,264, filed on Jun. 27, 2003.

(51) Int. Cl.
*A01N 63/00* (2006.01)
*C12N 5/071* (2010.01)

(52) U.S. Cl.
USPC ........... 424/93.7; 435/366; 435/378; 435/381

(58) Field of Classification Search
None
See application file for complete search history.

(56) References Cited

U.S. PATENT DOCUMENTS

| | | |
|---|---|---|
| 4,352,883 A | 10/1982 | Lim |
| 4,882,162 A | 11/1989 | Ikada et al. |
| 4,963,489 A | 10/1990 | Naughton et al. |
| 5,004,681 A | 4/1991 | Boyse et al. |
| 5,192,553 A | 3/1993 | Boyse et al. |
| 5,286,632 A | 2/1994 | Jones |
| 5,320,962 A | 6/1994 | Stiles et al. |
| 5,342,761 A | 8/1994 | MacLeod |
| 5,437,994 A | 8/1995 | Emerson et al. |
| 5,443,950 A | 8/1995 | Naughton et al. |
| 5,466,233 A | 11/1995 | Weiner et al. |
| 5,486,359 A | 1/1996 | Caplan et al. |
| 5,580,777 A | 12/1996 | Bernard et al. |
| 5,589,376 A | 12/1996 | Anderson et al. |
| 5,670,483 A | 9/1997 | Zhang et al. |
| 5,677,181 A | 10/1997 | Parish |
| 5,693,332 A | 12/1997 | Hansbrough |
| 5,698,518 A | 12/1997 | Carson et al. |
| 5,707,643 A | 1/1998 | Ogura et al. |
| 5,718,922 A | 2/1998 | Herrero-Vanrell et al. |
| 5,736,516 A | 4/1998 | Louis |
| 5,811,094 A | 9/1998 | Caplan et al. |
| 5,827,735 A | 10/1998 | Young et al. |
| 5,834,308 A | 11/1998 | Peck et al. |
| 5,840,580 A | 11/1998 | Terstappen et al. |
| 5,842,477 A | 12/1998 | Naughton et al. |
| 5,843,780 A | 12/1998 | Thomson |
| 5,843,781 A | 12/1998 | Ballermann et al. |
| 5,869,079 A | 2/1999 | Wong et al. |
| 5,902,598 A | 5/1999 | Chen et al. |
| 5,902,741 A | 5/1999 | Purchio et al. |
| 5,906,934 A | 5/1999 | Grande et al. |
| 5,919,702 A | 7/1999 | Purchio et al. |
| 5,942,225 A | 8/1999 | Bruder et al. |
| 5,955,343 A | 9/1999 | Holmes et al. |
| 5,962,325 A | 10/1999 | Naughton et al. |
| 5,994,094 A | 11/1999 | Hötten et al. |
| 6,001,647 A | 12/1999 | Peck et al. |
| 6,022,743 A | 2/2000 | Naughton et al. |
| 6,059,968 A | 5/2000 | Wolf |
| 6,140,039 A | 10/2000 | Naughton et al. |
| 6,153,591 A | 11/2000 | Cai et al. |
| 6,171,610 B1 | 1/2001 | Vacanti et al. |
| 6,179,872 B1 | 1/2001 | Bell et al. |
| 6,200,606 B1 | 3/2001 | Peterson et al. |
| 6,200,806 B1 | 3/2001 | Thomson |
| 6,214,369 B1 | 4/2001 | Grande et al. |
| 6,251,090 B1 | 6/2001 | Avery et al. |
| 6,291,240 B1 * | 9/2001 | Mansbridge et al. ......... 435/395 |
| 6,323,188 B1 * | 11/2001 | Weissman ...................... 514/52 |
| 6,326,201 B1 | 12/2001 | Fung et al. |
| 6,331,313 B1 | 12/2001 | Wong et al. |
| 6,333,029 B1 | 12/2001 | Vyakarnam et al. |
| 6,355,239 B1 | 3/2002 | Bruder et al. |
| 6,355,699 B1 | 3/2002 | Vyakarnam et al. |
| 6,358,737 B1 | 3/2002 | Bonewald et al. |

(Continued)

FOREIGN PATENT DOCUMENTS

| | | |
|---|---|---|
| CN | 1407088 | 2/2003 |
| EP | 1 216 718 | 6/2002 |

(Continued)

OTHER PUBLICATIONS

Taylor et al. Cardiac chimerism as a mechanism for self-repair: does it happen and if so to what degree? Circulation. 106(1):2-4, Jul. 2002.*
Foley et al. Heart induction: embryology to cardiomyocyte regeneration. Trends Cardiovasc Med. 14(3):121-5, Apr. 2004.*
Jikuhara et al. Left atrial function as a reliable predictor of exercise capacity in patients with recent myocardial infarction. Chest. vol. 111, No. 4, pp. 922-928, Apr. 1997.*
Timmermans et al. Stem cells for the heart, are we there yet? Cardiology. vol. 100, No. 4, pp. 176-185, 2003.*
Verma et al. Gene therapy—promises, problems and prospects. Nature. vol. 389, No. 6648, pp. 239-242, Sep. 1997.*
Palu et al. In pursuit of new developments for gene therapy of human diseases. J Biotechnol. vol. 68, No. 1, pp. 1-13, Feb. 1999.*

(Continued)

*Primary Examiner* — Jennifer Dunston
(74) *Attorney, Agent, or Firm* — Philip J. Johnson; Johnson & Johnson

(57) ABSTRACT

Cells derived from postpartum tissue and methods for their use in treatment of diseases of the heart or circulatory system are disclosed. Cells may be used in either differentiated or undifferentiated forms, in homogenous cultures, or as populations with other cells, and in conjunction with other bioactive factors.

6 Claims, No Drawings

(56) References Cited

U.S. PATENT DOCUMENTS

| | | |
|---|---|---|
| 6,372,494 B1 | 4/2002 | Naughton et al. |
| 6,375,972 B1 | 4/2002 | Guo et al. |
| 6,387,367 B1 | 5/2002 | Davis-Sproul et al. |
| 6,391,297 B1 | 5/2002 | Halvorsen |
| 6,429,013 B1 | 8/2002 | Halvorsen et al. |
| 6,436,704 B1 | 8/2002 | Roberts et al. |
| 6,497,875 B1 | 12/2002 | Sorrell et al. |
| 6,528,245 B2 | 3/2003 | Sanchez-Ramos et al. |
| 6,534,084 B1 | 3/2003 | Vyakarnam et al. |
| 6,555,374 B1 | 4/2003 | Gimble et al. |
| 6,599,323 B2 | 7/2003 | Melican et al. |
| 6,610,535 B1 | 8/2003 | Lu et al. |
| 6,638,765 B1 | 10/2003 | Rosenberg |
| 6,673,606 B1 | 1/2004 | Tennekoon et al. |
| 6,680,198 B1 | 1/2004 | Snyder et al. |
| 6,686,198 B1 | 2/2004 | Melton et al. |
| 6,703,017 B1 | 3/2004 | Peck et al. |
| 6,916,655 B2 | 7/2005 | Yasumoto et al. |
| 7,413,734 B2 | 8/2008 | Mistry et al. |
| 7,510,873 B2 | 3/2009 | Mistry et al. |
| 7,524,489 B2 | 4/2009 | Messina et al. |
| 7,560,276 B2 | 7/2009 | Harmon et al. |
| 7,875,272 B2 | 1/2011 | Messina et al. |
| 7,875,273 B2 | 1/2011 | Messina et al. |
| 8,277,796 B2 | 10/2012 | Messina et al. |
| 8,318,483 B2 | 11/2012 | Mistry et al. |
| 2001/0024824 A1 | 9/2001 | Moss et al. |
| 2001/0031256 A1 | 10/2001 | Edge |
| 2001/0046489 A1 | 11/2001 | Habener et al. |
| 2002/0022676 A1 | 2/2002 | He et al. |
| 2002/0028510 A1 | 3/2002 | Sanberg et al. |
| 2002/0062151 A1 | 5/2002 | Altman et al. |
| 2002/0081725 A1 | 6/2002 | Tsang et al. |
| 2002/0098584 A1 | 7/2002 | Palmer et al. |
| 2002/0119565 A1 | 8/2002 | Clarke et al. |
| 2002/0123141 A1 | 9/2002 | Hariri |
| 2002/0150986 A1 | 10/2002 | Lau |
| 2002/0151056 A1 | 10/2002 | Sasai et al. |
| 2002/0160471 A1 | 10/2002 | Kisiday et al. |
| 2002/0160510 A1* | 10/2002 | Hariri ............................ 435/368 |
| 2002/0164307 A1 | 11/2002 | Habener et al. |
| 2002/0164791 A1 | 11/2002 | Van Der Kooy et al. |
| 2002/0168763 A1 | 11/2002 | Yan et al. |
| 2002/0182728 A1 | 12/2002 | Ramiya et al. |
| 2002/0187550 A1 | 12/2002 | Dinsmore et al. |
| 2002/0192816 A1 | 12/2002 | Roberts et al. |
| 2003/0003574 A1 | 1/2003 | Toma et al. |
| 2003/0007954 A1* | 1/2003 | Naughton et al. ............ 424/93.7 |
| 2003/0022369 A1 | 1/2003 | Fillmore et al. |
| 2003/0031657 A1 | 2/2003 | Habener et al. |
| 2003/0032179 A1 | 2/2003 | Hariri |
| 2003/0032183 A1 | 2/2003 | Sheridan |
| 2003/0049837 A1 | 3/2003 | Weiss et al. |
| 2003/0059939 A1 | 3/2003 | Page et al. |
| 2003/0082155 A1 | 5/2003 | Habener et al. |
| 2003/0082160 A1 | 5/2003 | Yu et al. |
| 2003/0096409 A1 | 5/2003 | Yasumoto et al. |
| 2003/0104997 A1 | 6/2003 | Black et al. |
| 2003/0109036 A1 | 6/2003 | Wu |
| 2003/0113910 A1 | 6/2003 | Levanduski |
| 2003/0118566 A1 | 6/2003 | Neuman et al. |
| 2003/0124721 A1 | 7/2003 | Cheatham et al. |
| 2003/0138948 A1 | 7/2003 | Fisk et al. |
| 2003/0138951 A1 | 7/2003 | Yin |
| 2003/0148513 A1 | 8/2003 | Sugaya et al. |
| 2003/0161818 A1 | 8/2003 | Weiss et al. |
| 2003/0162290 A1 | 8/2003 | Inoue et al. |
| 2003/0170215 A1 | 9/2003 | Tsang et al. |
| 2003/0175963 A1 | 9/2003 | Rosenberg |
| 2003/0180269 A1 | 9/2003 | Hariri |
| 2003/0186439 A1 | 10/2003 | Nakauchi et al. |
| 2003/0199447 A1 | 10/2003 | Goldman et al. |
| 2003/0203483 A1 | 10/2003 | Seshi |
| 2003/0203484 A1 | 10/2003 | Black et al. |
| 2003/0207450 A1 | 11/2003 | Young et al. |
| 2003/0211087 A1 | 11/2003 | Goldman |
| 2003/0211603 A1 | 11/2003 | Earp et al. |
| 2003/0211605 A1 | 11/2003 | Lee et al. |
| 2003/0212024 A1 | 11/2003 | Keating et al. |
| 2003/0219894 A1 | 11/2003 | Seino et al. |
| 2003/0228295 A1 | 12/2003 | Svendsen .................... 424/93.21 |
| 2003/0235563 A1 | 12/2003 | Strom et al. ................ 424/93.21 |
| 2003/0235909 A1 | 12/2003 | Hariri et al. ..................... 435/372 |
| 2004/0005704 A1 | 1/2004 | Csete et al. ..................... 435/368 |
| 2004/0009593 A1 | 1/2004 | Keirstead et al. ............. 435/368 |
| 2004/0014206 A1 | 1/2004 | Robl et al. ..................... 435/325 |
| 2004/0014210 A1 | 1/2004 | Jessell et al. .................. 435/368 |
| 2004/0014211 A1 | 1/2004 | Ogle et al. ..................... 435/368 |
| 2004/0014662 A1 | 1/2004 | Lindquist et al. ................ 514/12 |
| 2004/0028660 A1 | 2/2004 | Hariri et al. |
| 2004/0029269 A1 | 2/2004 | Goldman et al. ............. 435/368 |
| 2004/0033597 A1 | 2/2004 | Toma et al. .................... 435/368 |
| 2004/0037818 A1 | 2/2004 | Brand et al. ................ 424/93.21 |
| 2004/0048372 A1 | 3/2004 | Hariri ............................ 435/366 |
| 2004/0058412 A1 | 3/2004 | Ho et al. ........................ 435/69.1 |
| 2004/0063202 A1 | 4/2004 | Petersen et al. ................ 435/368 |
| 2004/0072344 A1 | 4/2004 | Inoue et al. .................... 435/366 |
| 2004/0136967 A1 | 7/2004 | Weiss et al. |
| 2005/0019865 A1 | 1/2005 | Kihm et al. |
| 2005/0032209 A1 | 2/2005 | Messina et al. |
| 2005/0037491 A1 | 2/2005 | Mistry et al. |
| 2005/0054098 A1 | 3/2005 | Mistry et al. |
| 2005/0058629 A1 | 3/2005 | Harmon et al. |
| 2005/0058631 A1 | 3/2005 | Kihm et al. |
| 2005/0074435 A1* | 4/2005 | Casper et al. ................. 424/93.7 |
| 2005/0148074 A1 | 7/2005 | Davies et al. |
| 2005/0249731 A1 | 11/2005 | Aslan et al. |
| 2006/0153815 A1 | 7/2006 | Seyda et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154366 A1 | 7/2006 | Brown et al. |
| 2006/0154367 A1 | 7/2006 | Kihm et al. |
| 2006/0166361 A1 | 7/2006 | Seyda et al. |
| 2006/0171930 A1 | 8/2006 | Seyda et al. |
| 2006/0188983 A1 | 8/2006 | Harris et al. |
| 2006/0223177 A1 | 10/2006 | Harris et al. |
| 2006/0233765 A1 | 10/2006 | Messina et al. |
| 2006/0233766 A1 | 10/2006 | Messina et al. |
| 2006/0234376 A1 | 10/2006 | Mistry et al. |
| 2007/0009494 A1 | 1/2007 | Mistry et al. |
| 2007/0014771 A1 | 1/2007 | Mistry et al. |
| 2007/0036767 A1 | 2/2007 | Mistry et al. |
| 2007/0141700 A1 | 6/2007 | Harmon |
| 2007/0160588 A1 | 7/2007 | Kihm et al. |
| 2007/0218549 A1 | 9/2007 | Mansbridge |
| 2007/0264269 A1 | 11/2007 | Harmon et al. |
| 2007/0264713 A1 | 11/2007 | Terstegge et al. |
| 2007/0275362 A1 | 11/2007 | Edinger et al. |
| 2008/0112939 A1 | 5/2008 | Colter et al. |
| 2008/0145934 A1 | 6/2008 | Harris et al. |
| 2008/0166328 A1 | 7/2008 | Harmon et al. |
| 2010/0210013 A1 | 8/2010 | Mistry et al. |
| 2010/0215714 A1 | 8/2010 | Messina et al. |
| 2010/0260843 A1 | 10/2010 | Messina et al. |
| 2012/0315251 A1 | 12/2012 | Harris et al. |
| 2013/0022585 A1 | 1/2013 | Messina et al. |

FOREIGN PATENT DOCUMENTS

| | | |
|---|---|---|
| EP | 1 316 322 | 6/2003 |
| EP | 0 333 328 B1 | 12/2003 |
| EP | 1 405 649 | 4/2004 |
| JP | 2003-235549 | 8/2003 |
| JP | 2004-254682 | 9/2004 |
| WO | 90/11354 A1 | 10/1990 |
| WO | 92/03917 A1 | 3/1992 |
| WO | 93/04169 A1 | 3/1993 |
| WO | WO 94/25584 A1 | 11/1994 |
| WO | 95/17911 A1 | 7/1995 |
| WO | WO 95/23216 | 8/1995 |
| WO | WO 96/01316 A1 | 1/1996 |
| WO | WO 96/05309 A2 | 2/1996 |
| WO | WO 98/17791 A1 | 4/1998 |

(56) References Cited

FOREIGN PATENT DOCUMENTS

| WO | WO 98/51317 | | 4/1998 |
|---|---|---|---|
| WO | WO 9903973 | A1 * | 1/1999 |
| WO | WO 99/28444 | | 6/1999 |
| WO | WO 00/09666 | | 2/2000 |
| WO | WO 00/38762 | | 7/2000 |
| WO | WO 00/46351 | | 8/2000 |
| WO | 00/73421 | A3 | 12/2000 |
| WO | WO 01/11011 | A2 | 2/2001 |
| WO | WO 01/19379 | A3 | 3/2001 |
| WO | WO 01/34775 | A1 | 5/2001 |
| WO | WO 02/29971 | A1 | 4/2002 |
| WO | WO 02/36751 | | 5/2002 |
| WO | WO 02/46373 | A1 | 6/2002 |
| WO | WO 02/059278 | A2 | 8/2002 |
| WO | WO 02/061053 | | 8/2002 |
| WO | WO 02/062969 | A2 | 8/2002 |
| WO | WO 02/063962 | A1 | 8/2002 |
| WO | WO 02/064748 | A2 | 8/2002 |
| WO | WO 02/064755 | A2 | 8/2002 |
| WO | WO 02/086107 | A2 | 10/2002 |
| WO | WO 03/023020 | A1 | 3/2003 |
| WO | WO 03/025149 | A2 | 3/2003 |
| WO | WO 03/029443 | A1 | 4/2003 |
| WO | WO 03/029445 | A1 | 4/2003 |
| WO | 03/039489 | A3 | 5/2003 |
| WO | WO 03/042405 | A2 | 5/2003 |
| WO | WO 03/048336 | A2 | 6/2003 |
| WO | WO 03/055992 | A2 | 7/2003 |
| WO | WO 03/064601 | A2 | 8/2003 |
| WO | WO 03/066832 | A2 | 8/2003 |
| WO | WO 03/068937 | A2 | 8/2003 |
| WO | WO 03/070922 | A1 | 8/2003 |
| WO | WO 03/072728 | A2 | 9/2003 |
| WO | WO 03/080822 | A1 | 10/2003 |
| WO | WO 03/087333 | A2 | 10/2003 |
| WO | WO 03/087392 | A2 | 10/2003 |
| WO | WO 03/089619 | A2 | 10/2003 |
| WO | 03/102151 | A2 | 12/2003 |
| WO | WO 03/010038 | A1 | 12/2003 |
| WO | WO 03/102134 | A2 | 12/2003 |
| WO | WO 03/104442 | A1 | 12/2003 |
| WO | WO 2004/011012 | A2 | 2/2004 |
| WO | WO 2004/011621 | A2 | 2/2004 |
| WO | WO 2004/016747 | A2 | 2/2004 |
| WO | WO 2004/023100 | A2 | 3/2004 |
| WO | 2004/072273 | A1 | 8/2004 |
| WO | WO 2006/036826 | | 9/2004 |
| WO | 2005/001076 | A2 | 1/2005 |
| WO | 2005/001077 | A2 | 1/2005 |
| WO | 2005/001078 | A2 | 1/2005 |
| WO | 2005/001079 | A2 | 1/2005 |
| WO | 2005/001080 | A2 | 1/2005 |
| WO | 2005/003334 | A2 | 1/2005 |
| WO | WO 2005/001080 | A3 | 3/2005 |
| WO | WO 2005/021738 | | 3/2005 |
| WO | 2005/038012 | A2 | 4/2005 |
| WO | 2005/042703 | A2 | 5/2005 |
| WO | WO 2005/001080 | R | 12/2005 |
| WO | WO 2006/027229 | | 3/2006 |
| WO | 2006/071773 | A2 | 7/2006 |
| WO | 2006/071777 | A2 | 7/2006 |
| WO | 2006/071778 | A2 | 7/2006 |
| WO | 2006/071794 | A2 | 7/2006 |
| WO | 2006/071802 | A2 | 7/2006 |
| WO | WO 2006/083394 | | 8/2006 |
| WO | WO 2006/105152 | | 10/2006 |
| WO | WO 2007/073552 | | 6/2007 |
| WO | WO 2007/108003 | | 9/2007 |
| WO | WO 2008/045498 | | 4/2008 |
| WO | WO 2008/060541 | | 5/2008 |

OTHER PUBLICATIONS

Luo et al. Synthetic DNA delivery systems. Nat Biotechnol. vol. 18, No. 1, pp. 33-36 Jan. 2000.*

Edelstein et al. Gene therapy clinical trials worldwide 1989-2004—an overview. J Gene Med. vol. 6, No. 6, pp. 597-602, Jun. 2004.*

Taylor et al. Regenerating funcitonal myocardium: Improved performance after sekeletal myoblast transplantation. Nature Medicine. vol. 4, No. 8, pp. 929-933. Erratum in Nature Medicine, vol. 4, No. 10, p. 1200.*

Hoynowski et al. Characterization and differentiation of equine umbilical cord-derived matrix cells. Biochemical and Biophysical Research Communications, vol. 362, pp. 347-353, Aug. 2007.*

Pountos et al. Mesenchymal stem cell tissue engineering: techniques for isolation, expansion and application. Injury, Int. J. Care Injured, vol. 38, Supplement 4, pp. S23-S33, 2007.*

Product information for Antibiotic-Antimycotic (100X). liquid, SKU# 15240-096, printed from http://products/invitrogen.com on Mar. 9, 2009.*

Covas et al. Isolation and culture of umbilical vein mesnchymal stem cells. Brazilian Journal of Medical and Biological Research, vol. 36, pp. 1179-1183, 2003.*

Baksh et al. Comparison of proliferative and multilineage differentiation potential of human mesenchymal stem cells derived from umbilical cord and bone marrow. Stem Cells, vol. 25, pp. 1384-1392, 2007.*

Kestendjieva et al. Characterization of mesenchymal stem cells isolated from the human umbilical cord. Cell Biology International, vol. 32, pp. 724-732, 2008.*

Taylor et al. Regenerating functional myocardium: Improved performance after skeletal myoblast transplantation. Nature Medicine, vol. 4, No. 8, pp. 929-933, 1998. Erratum in Nature Medicine, vol. 4, No. 10, p. 1200, 1998.*

Eblenkamp, M. et al., "Umbilical cord stromal cells (UCSC). Cells featuring osteogenic differentiation potential," *Der Orthopade*, Dec. 2004, 33(12), 1338-1345.

Fukuchi, Y. et al., "Human Placenta-Derived Cells Have Mesenchymal Stem/Progenitor Cell Potential," *Stem Cells*, Alphamed Press, Dayton Ohio, 2004, 22(5), 649-658.

Wulf, G. G. et al., "Mesengenic Progenitor Cells Derived From Human Placenta," *Tissue Engineering*, Larchmont, NY, Jul. 2004, 10(7/8), 1136-1147.

Aboody, K.S., et al., "Neural stem cells display extensive tropism for pathology in adult brain: evidence from intracranial gliomase," *PNAS*, 2000, 97(23), 12846-12851.

Age-Related Eye Disease Study Research Group, "A randomized, placebo-controlled, clinical trial of high-dose supplementation with vitamins C and E, beta carotene, and zinc for age-related macular degeneration and vision loss," AREDS Report No. 8, *Arch. Ophthalmal*, 2001, 119, 1417-1436.

Allcock, H.R., et al., "Synthesis of poly[amino acid alkyl ester)phosphazenes]$^{1-3}$," *Macromolecule*, 1977, 10(4), 824-830.

Altman, G.H., et al., "Advanced bioreactor with controlled application of multi-dimensional strain for tissue engineering," *J. Biomech. Eng.*, 2002, 124, 742-749.

Altman, R.D., et al., "Radiographic assessment of progression in osteoarthritis," *Arthritis & Rheum.*, 1987, 30(11), 1214-1225.

Anseth, K.S., et al., "In situ forming degradable networks and their application in tissue engineering and drug delivery," *J. of Control Release*, 2002, 78, 199-209.

Avital, I., et al., "Isolation, characterization, and transplantation of bone marrow-derived hepatocyte stem cells," *Biochem. & Biophys. Res. Comm.*, 2001, 288, 156-164.

Azizi, S.A., et al., "Engraftment and migration of human bone marrow stromal cells implanted in the brains of albino rats—similarities to astrocyte grafts," *Proc. Natl. Acad. Sci. USA*, 1998, 95, 3908-3913.

Baker, K.A., et al., "Intrastriatal and intranigral grafting of hNT neurons in the 6-OHDA rat model of Parkinson's Disease," *Exper. Neurol.*, 2000, 162, 350-360.

Balis, F., et al., "Central nervous system pharmacology of antileukemic drugs," *Am. J. of Pediatric. Hematol. Oncol.*, 1989, 11(1), 74-86.

Balkema, G.W., et al., "Impaired visual thresholds in hypopigmented animals," *Visual Neuroscience*, 1991, 6, 577-585.

(56) References Cited

OTHER PUBLICATIONS

Barberi, T., et al., "Neural subtype specification of fertilization and nuclear transfer embryonic stem cells and application in parkinsonian mice," *Nature Biotechnology*, 2003, 21(10), 1200-1207.
Beck, R.W., et al., "A clinical comparison of visual field testing with a new automated perimeter, the Humphrey field analyzer, and the Goldmann perimeter," *Ophthalmology*, 1985, 92(1), 77-82.
Björklund, L.M., et al., "Embryonic stem cells develop into functional dopaminergic neurons after transplantation in a Parkinson rat model," *PNAS*, 2002, 99(4), 2344-2349.
Bouteiller, P.L., et al., "Soluble HLA-G1 at the materno-foetal interface—a review," *Placenta*, 2003, 24 (Suppl. A), S10-S15.
Brodsky, S.V., et al., "Coagulation, fibrinolysis and angiogenesis: new insights from knockout mice," *Exp. Nephrol.*, 2002, 10, 299-306.
Brooks, P., "Inflammation as an important feature of osteoarthritis," *Bull. World Health Org.*, 2003, 81(9), 689-690.
Brown, J.A., et al., "Blockade of programmed death-1 ligands on dendritic cells enhances T cell activation and cytokine production," *The J. of Immunology*, 2003, 170, 1257-1266.
Burnstein, R.M., et al., "Differentiation and migration of long term expanded human neural progenitors in a partial lesion model of Parkinson's disease," *Intern. J. of Biochem. & Cell Biology*, 2004, 36, 702-713.
Caballero, S., et al., "The many possible roles of stem cells in age-related macular degeneration," *Graefe's Arch Clin. Exp. Ophthalmol*, 2004, 242, 85-90.
Campbell, I.K., et al., "Human articular cartilage and chondrocytes produce hemopoietic colony-stimulating factors in culture in response to IL-$1^1$," *J. of Immun.*, 1991, 147, 1238-1246.
Cao, Q., et al., "Stem cell repair of central nervous system injury," *J. of Neuroscience Res.*, 2002, 68, 501-510.
Caplan, A.I., et al., "Mesenchymal stem cells: building blocks for molecular medicine in the $21^{st}$ century," *Trends in Molecular Med.*, 2001, 7(6), 259-264.
Chargracui, J., et al., "Fetal liver stroma consists of cells in epithelial-to-mesenchymal transition," *Blood*, 2003, 101, 2973-2982.
Chen, D., et al., "Differential roles for bone morphogenic protein (BMP) receptor type IB and IA in differentiation and specification of mesenchymal precursor cells to osteoblast and adipocyte lineages," *J. Cell Biol.*, 1998, 142(1), 295-305.
Cheng, A., et al., "Nitric oxide acts in a positive feedback loop with BDNF to regulate neural progenitor cell proliferation and differentiation in the mammalian brain," *Dev. Biol.*, 2003, 258, 319-333.
Coumans, B., et al., "Lymphoid cell apoptosis induced by trophoblastic cells: a model of active foeto-placental tolerance," *J. of Immunological Methods*, 1999, 224, 185-196.
D'Cruz, P.M., et al., "Mutation of the receptor tyrosine kinase gene Mertk in the retinal dystrophic RCS rat," *Hum. Mol. Genet.*, 2000, 9(4), 645-651.
Danon, D., et al., "Macrophage treatment of pressure sores in paraplegia," *J. of Wound Care*, 1998, 7(6), 281-283.
Danon, D., et al., "Treatment of human ulcers by application of macrophages prepared from a blood unit," *Exp. Gerontol.*, 1997, 32(6), 633-641.
Dimri, G.P., et al., "A biomarker that identifies senescent human cells in culture and in aging skin in vivo," *Proc. Natl. Acad. Sci. USA*, 1995, 92, 9363-9367.
Domb, A., et al., "Degradable polymers for site-specific drug delivery," *Polymers for Advanced Technologies*, 1992, 3, 279-292.
Doshi, S.N., et al., "Evolving role of tissue factor and its pathway inhibitor," *Critical Care Med.*, 2002, 30(5), S241-S250.
Du, Y., et al., "Functional reconstruction of rabbit corneal epithelium by human limbal cells cultured on amniotic membrane," *Molecular Vision*, 2003, 9, 635-643.
Edlund, H., "Pancreatic organogenesis—developmental mechanisms and implications for therapy," *Nat. Rev. Genet.*, 2002, 3, 524-532.
Efrat, S., et al., "Cell replacement therapy for type 1 diabetes," *TRENDS in Molecular Medicine*, 2002, 8(7), 334-339.
Ehtesham, M., et al., "Induction of glioblastoma apoptosis using neural stem cell-mediated delivery of tumor necrosis factor-related apoptosis-inducing ligand," *Cancer Res.*, 2002, 62, 7170-7174.
Ehtesham, M., et al., "The use of interleukin 12-secreting neural stem cells for the treatment of intracranial glioma," *Cancer Res.*, 2002, 5657-5663.
Ende, N., et al., "Parkinson's disease mice and human umbilical cord blood," *J. Med.*, 2002, 33(1-4), 173-180, 1 page (Abstract).
Engstad, C.S., et al., "The effect of soluble β-1,3-glucan and lipopolysaccharide on cytokine production and coagulation activation in whole blood," *Int. Immunopharmacol.*, 2002, 2, 1585-1597.
Enzmann, V., et al, "Enhanced induction of RPE lineage markers in pluripotent neural stem cells engrafted into the adult rat subretinal space," *Investig. Ophthalmol. Visual Sci.*, 2003, 44, 5417-5422.
Fazeabas, A.T., et al., "Endometrial function: cell specific changes in the uterine environment," *Mol. & Cellular. Endo.*, 2002, 186, 143-147.
Fiegel, H.C., et al., "Liver-specific gene expression in cultured human hematopoietic stem cells," *Stem Cells*, 2003, 21, 98-104.
Fischer, D., et al., "Lens-injury-stimulated axonal regeneration throughout the optic pathway of adult rats," *Exp. Neurol.*, 2001, 172, 257-272.
Freed, C.R., et al., "Transplantation of embryonic dopamine neurons for severe Parkinson's disease," *N. Engl. J. Med.*, 2001, 344(10), 710-719.
Frenkel, O., et al., "Activated macrophages for treating skin ulceration: gene expression in human monocytes after hypo-osmotic shock," *Clin. Exp. Immunol.*, 2002, 128, 59-66.
Friedman, J.A., et al., "Biodegradable polymer grafts for surgical repair of the injured spinal cord," *Neurosurgery*, 2002, 51(3), 742-751.
Fukuda, K., et al., "Reprogramming of bone marrow mesenchymal stem cells into cardiomyocytes," *C.R. Biol.*, 2002, 325, 1027-1038.
Gerdes, D., et al., "Cloning and tissue expression of two putative steroid membrane receptors," *Biol. Chem.*, 1998, 379, 907-911.
Gellersen, B., et al., "Cyclic AMP and progesterone receptor crosstalk in human endometrium: a decidualizing affair," *J. of Endocrinol.*, 2003, 178, 357-372.
Gökhan, ç., et al., "Basic and clinical neuroscience applications of embryonic stem cells," *Anat. Rec. (New Anat)*, 2001, 265, 142-156.
Gosiewska, A., et al., "Development of a three-dimensional transmigration assay for testing cell-polymer interactions for tissue engineering applications," *Tissue Eng.*, 2001, 7(3), 267-277.
Gottleib, D.I., "Large-scale sources of neural stem cells," *Ann. Rev. Neurosci.*, 2002, 25, 381-407.
Halvorsen, Y.D., et al., "Extracellular matrix mineralization and osteoblast gene expression by human adipose tissue-derived stromal cells," *Tissue Eng.*, 2001, 7, 729-741.
Hanahan, D., "Heritable formation of pancreatic β-cell tumours in transgenic mice expressing recombinant insulin/simian virus 40 oncogenes," *Nature*, 1985, 315, 115-122.
Haruta, M., et al., "In vitro and in vivo characterization of pigment epithelial cells differentiated from primate embryonic stem cells," *Investig. Ophthalmol. & Visual Sci.*, 2004, 45(3), 1020-1025.
Hayflick, L., "The longevity of cultured human cells," *J. Am. Geriatr. Soc.*, 1974, 22(1), 1-12.
Hayflick, L., "The strategy of senescence," *Gerontologist*, 1974, 14(1), 37-45.
Hongpaisan, J., "Inhibition of proliferation of contaminating fibroblasts by D-valine in cultures of smooth muscle cells from human myometrium," *Cell Biol. Int.*, 2000, 24, 1-7.
Hu, A., et al., "Hepatic differentiation from embryonic stem cells in vitro," *Chin. Med. J.*, 2003, 116(12), 1893-1897.
Hughes, G.C., et al., "Therapeutic angiogenesis in chronically ischemic porcine myocardium: comparative effects of bFGF and VEGF," *Ann. Thorac. Surg.*, 2004, 77, 812-818.
Hutmacher, D.W., "Scaffold design and fabrication technologies for engineering tissues—state of the art and future perspectives," *J. Biomater. Sci. Polymer Edn.*, 2001, 12(1), 107-124.
Isacson, O., et al., "Specific axon guidance factors persist in the adult brain as demonstrated by pig neuroblasts transplanted to the rat," *Neurosci.*, 1996, 75(3), 827-837.

(56) References Cited

OTHER PUBLICATIONS

Isacson, O., "The production and use of cells as therapeutic agents in neurodegenerative diseases," *The Lancet (Neurology)*, 2003, 2, 417-424.
Ito, Y., et al., "A quantitative assay using basement membrane extracts to study tumor angiogenesis in vivo," *Int. J. Cancer*, 1996, 67, 148-152.
Jackson, J.A., et al., "Regeneration of ischemic cardiac muscle and vascular endothelium by adult stem cells," *J. Clin. Invest.*, 2001, 107, 1395-1402.
Janderova, L., et al., "Human mesenchymal stem cells as an in vitro model for human adipogenesis," *Obes. Res.*, 2003, 11(1), 65-74.
Jang, Y.K., et al., "Retinoic acid-mediated induction of neurons and glial cells from human umbilical cord-derived hematopoietic stem cells," *J. of Neurosci. Res.*, 2004, 75, 573-584.
Johe, K.K., et al., "Single factors direct the differentiation of stem cells from the fetal and adult central nervous system," *Genes & Devel.*, 1996, 10, 3129-3140.
Johnstone, B., et al., "In vitro chondrogenesis of bone-marrow-derived mesenchymal stem cells," *Exp. Cell Res.*, 1998, 238, 265-272.
Jones-Villeneuve, E.M., et al., "retinoic acid-induced neural differentiation of embryonal carcinoma cells," *Mol. & Cellu. Biol.*, 1983, 3(12), 2271-2279.
Kadiyala, S., et al., "Culture expanded canine mesenchymal stem cells possess osteochondrogenic potential in vivo and in vitro," *Cell Transplant*, 1997, 6(2), 125-134.
Kicic, A., et al., "Differentiation of marrow stromal cells into photoreceptors in the rat eye," *J. of Neurosci.*, 2003, 23(21), 7742-7749.
Kim, S.K., et al., "Intercellular signals regulating pancreas development and function," *Genes Dev.*, 2001, 15, 111-127.
Kim, J.-H., et al., "Dopamine neurons derived from embryonic stem cells function in an animal model of Parkinson's disease," *Nature*, 2002, 418, 50-56.
Kim, J.Y., et al., "Ocular surface reconstruction: limbal stem cell transplantation," *Ophthal. Clin. N Am.*, 2003, 16, 67-77.
Lang, K.J.D., et al., "Differentiation of embryonic stem cells to a neural fate: a route to re-building the nervous system," *J. of Neurosci. Res.*, 2004, 76, 184-192.
Le Belle, J.E., et al., "Stem cells for neurodegenerative disorders: where can we go from here?," *BioDrugs*, 2002, 16, 389-401.
Li, A., et al., "IL-8 directly enhanced endothelial cell survival, proliferation, and matrix metalloproteinases production and regulated angiogenesis," *J. Immunol.*, 2003, 170(6), 3369-3376.
Li, L.X., et al., "Inherited retinal dystrophy in the RCS rat: prevention of photoreceptor degeneration by pigment epithelial cell transplantation," *Exp. Eye Res.*, 1988, 47, 911-917.
Li, Y., et al., "Intracerebral transplantation of bone marrow stromal cells in a 1-methyl-4-phenyl-1,2,3,6-tetrahydropyridine mouse model of Parkinson's disease," *Neuroscience Letts.*, 2001, 315, 67-70.
Li, Y., et al., "Transplanted olfactory ensheathing cells promote regeneration of cut adult rat optic nerve axons," *J. of Neuro.*, 2003, 23(21), 7783-7788.
Liu, Y.-J., et al., "Molecular and genetic mechanisms of obesity: implications for future management," *Curr. Mol. Med.*, 2003, 3, 325-340.
Lockhart, et al., "Expression monitoring by hybridization to high-density oligonucleotide arrays," *Nat. Biotechnol.*, 1996, 14(13), 1675-1680.
Lund, R.D., et al., "Subretinal transplantation of genetically modified human cell lines attenuates loss of visual function in dystrophic rats," *Proc. Natl. Acad. Sci. USA*, 2001, 98(17), 9942-9947.
Lund, R.D., et al., "Cell transplantation as a treatment for retinal disease," *Progress in Retinal and Eye Research*, 2001, 20(4), 415-449.
Lund, R.L., et al., "Retinal transplantation: progress and problems in clinical application," *J. Leukocyte Biol.*, 2003, 74, 151-160.

Marx, W.F., et al., "Endovascular treatment of experimental aneurysms by use of biologically modified embolic devices: coil-mediated intraaneurysamal delivery of fibroblast tissue allografts," *Am. J. Neuroradiol.*, 2001, 22, 323-333.
Mason, A.J., et al., "The hypogonadal mouse: reproductive functions restored by gene therapy," *Science*, 1986, 234, 1372-1378.
Mayer-Proschel, M., et al., "Isolation of lineage-restricted neuronal precursors from multipotent neuroepithelial stem cells," *Neuron.*, 1997, 19, 773-785.
McDonald, J.A., et al., "Diminished responsiveness of male homosexual chronic hepatitis B virus carriers with HTLV-III antibodies to recombinant α-interferon," *Hepatology*, 1987, 7(4), 719-723.
Messina, D.J., et al., "Comparison of pure and mixed populations of human fetal-derived neural progenitors transplanted into intact and adult rat brain," *Exper. Neurol.*, 2003, 184, 816-829.
Mitchell, et al., "Matrix cells from Wharton's jelly form neurons and glia," *Stem Cells*, 2003, 21, 50-60.
Moll, S., et al., "Monitoring warfarin therapy in patients with lupus anticoagulants," *Ann. Intern. Med.*, 1997, 127(3), 177-185.
Mombaerts, et al., "Creation of a large genomic deletion at the T-cell antigen receptor β-subunit locus in mouse embryonic stem cells by gene targeting," *Proc. Nat. Acad. Sci. USA*, 1991, 88, 3084-3087.
Nakamura, T., et al., "Ocular surface reconstruction using cultivated mucosal epithelial stem cells," *Cornea*, 2003, 22(Supp. 1), S75-S80.
Nicosia, R.F., et al., "Modulation of microvascular growth and morphogenesis by reconstituted basement membrane gel in three-dimensional cultures of rat aorta: a comparative study of angiogenesis in matrigal, collagen, fibrin, and plasma clot," in *Vitro Cell Dev. Biol.*, 1990, 26, 119-128.
Nishida K., et al., "Functional bioengineered corneal epithelial sheet grafts from corneal stem cells expanded ex vivo on a temperature-responsive cell culture surface," *Transplantation*, 2004, 77(3), 379-385.
Nixon, P.J., et al., "The contribution of cone responses to rat electroretinograms," *Clin. Experiment Ophthalmol.*, 2001, 29(3), 193-196.
Nusinowitz, S., et al., "Rod multifocal electroretinograms in mice," *Invest Ophthalmol Vis. Sci.*, 1999, 40(12), 2848-2858.
Oh, S.-H., et al., "Hepatocyte growth factor induces differentiation of adult rat bone marrow cells into a hepatocyte lineage in vitro," *Biochem. & Biophys. Res. Comm.*, 2000, 279, 500-504.
Okumoto, K., et al., "Differentiation of bone marrow cells into cells that express liver-specific genes in vitro: implication of the notch signals in differentiation," *Biochem. & Biophys. Res. Commun.*, 2003, 304, 691-695.
Orlic, D., et al., "Stem cells for myocardial regeneration," *Circ. Res.*, 2002, 91, 1092-1102.
Ornitz, D.M., et al., "Elastase I promoter directs expression of human growth hormone and SV40 T antigen genes to pancreatic acinar cells in transgenic mice," *Cold Spring Harbor Symp.Quant. Biol.*, 1985, vol. L, 399-409.
Osborne, N.N., et al., "Some current ideas on the pathogenesis and the role of neuroprotection in glaucomatous optic neuropathy," *Eur. J. Ophthalmol.*, 2003, 13(Supp. 3), S19-S26.
Rabbany, S.Y., et al., "Molecular pathways regulating mobilization of marrow-derived stem cells for tissue revascularization," *TRENDS in Molecular Med.*, 2003, 9(3), 109-117.
Rafii, S., et al., "Therapeutic stem and progenitor cell transplantation for organ vascularization and regeneration," *Nature Med.*, 2003, 9(6), 702-712.
Raman-Cueto, A., et al., "Functional recovery of paraplegic rats and motor axon regeneration in their spinal cords by olfactory ensheathing glia," *Neuron*, 2000, 25, 425-435.
Readhead, C., et al., "Expression of a myelin basic protein gene in transgenic shiverer mice: correction of the dysmyelinating phenotype," *Cell*, 1987, 48, 703-712.
Refaie, A., et al., "Experimental islet cell transplantation in rats: optimization of the transplantation site," *Trans. Proc.*, 1998, 30, 400-403.
Reubinoff, B.E., et al., "Neural progenitors from human embryonic stem cells," *Nature Biotechnology*, 2001, 19, 1134-1140.

(56) References Cited

OTHER PUBLICATIONS

Rickard, D.J., et al., "Induction of rapid osteoblast differentiation in rat bone marrow stromal cell cultures by dexamethasone and BMP-2," *Dev. Biol.*, 1994, 161, 218-228.
Romanov, Y.A., et al., "Searching for alternative sources of postnatal human mesenchymal stem cells," *Stem Cells*, 2003, 21, 105-110.
Rosen, E.M., et al., "HGF/SF in angiogenesis," *Ciba Found. Symp.*, 1997, 212, 215-229.
Rutherford, A., et al., "Eyeing-up stem cell transplantation," *Trends in Molecular Medicine*, 2003, 7(1), p. 11.
Sahn, D.J., et al., "Recommendations regarding quantitation in M-Mode echocardiography: results of a survey of echocardiographic measurements," *Circulation*, 1978, 58, 1072-1083.
Sakariassen, K.S., et al., "Methods and models to evaluate shear-dependent and surface reactivity-dependent antithrombotic efficacy," *Thromb. Res.*, 2001, 104, 149-174.
Salcedo, et a., "Human endothelial cells express CCR2 and respond to MCP-1: direct role of MCP-1 in angiogenesis and tunior progression," *Blood*, 2000, 96(1), 34-40.
Sauve, Y., et al., "The relationship between full field electroretinogram and perimetry-like visual thresholds in RCS rats during photoreceptor degeneration and rescue by cell transplants," *Vision Res.*, 2004, 44(1), 9-18.
Schraermeyer, U., et al., "Subretinally transplanted embryonic stem cells rescue photoreceptor cells from degeneration in the RCS rats," *Cell Transplantation*, 2001, 10, 673-680.
Schwartz, R.E., et al., "Multipotent adult progenitor cells from bone marrow differentiate into functional hepatocyte-like cells," *J. of Clin. Invest.*, 2002, 109(10), 1291-1302.
Sebire, G., et al., "In vitro production of IL-6,IL-1 β, and tumor necrosis factor-alpha by human embryonic microglial and neural cells," *J. Immunol.*, 1993, 150, 1 517-1523.
Shani, M., "Tissue-specific expression of rat myosin light-chain 2 gene in transgenic mice," *Nature*, 1985, 314, 283-286.
Shimizu, T., et al., "Cell sheet engineering for myocardial tissue reconstruction," *Biomaterials*, 2003, 24, 2309-2316.
Siminoff, R., et al., "Properties of reptilian cutaneous mechanoreceptors," *Exp. Neurol.*, 1968, 20(3), 403-414.
Sordillo, L.M., et al., "Culture of bovine mammary epithelial cells in D-valine modified medium: selective removal of contaminating fibroblasts," *Cell Biol. Int. Rep.*, 1988, 12, 355-364.
Storch, T.G., "Oxygen concentration regulates 5-azacytidine-induced myogenesis in $C_3H/10T1/2$ cultures," *Biochim. Biophys. Acta*, 1990, 1055, 126-129.
Street, C.N., et al., "Stem cells: a promising source of pancreatic islets for transplantation in type 1 diabetes," *Curr. Top Dev. Biol.*, 2003, 58, 111-136.
Svendsen, C.N., et al., "Long-term survival of human central nervous system progenitor cells transplanted into a rat model of Parkinson's disease," *Experim. Neurol.*, 1997, 148, 135-146.
Svendsen, C.N., "The amazing astrocyte," *Nature*, 2002, 417, 29-32.
Swift, G.H., et al., "Tissue-specific expression of the rat pancreatic elastase I gene in transgenic mice," *Cell*, 1984, 38, 639-646.
Tomita, M., et al., "Bone marrow-derived stem cells can differentiate into retinal cells in injured rat retina," *Stem Cells*, 2002, 20, 279-283.
Tresco, P.A., et al., "Cellular transplants as sources for therapeutic agents," *Advanced Drug Delivery Reviews*, 2000, 42, 3-27.
Tsonis, P.A., et al., "Lens and retina regeneration: transdifferentiation, stem cells and clinical applications," *Experim. Eye Res.*, 2004, 78, 161-172.
Turner, J.F., "Inherited retinal dystrophy in the RCS rat: prevention of photoreceptor degeneration by pigment epithelial cell transplantation," *Exp. Eye Res.*, 1988, 47, 911-917.
Tusher, V.G., et al., "Significance analysis of microarrays applied to the ionizing radiation response," *Proc. Natl. Acad. Sci. USA*, 2001, 98(9), 5116-5121.
Van Hoffelen, S.J., et al., "Incorporation of murine brain progenitor cells into the developing mammalian retina," *Invest. Ophthalmol. Vis. Sci.*, 2003, 44, 426-434.

Vassliopoulos, G., et al., "Transplanted bone marrow regenerates liver by cell fusion," *Nature*, 2003, 422, 901-904.
Villegas-Perez, M.P., et al., "Influences of peripheral nerve grafts on the survival and regrowth of axotomized retinal ganglion cells in adult rats," *J. of Neurosci.*, 1988, 8(1), 265-280.
Von Koskull, H., et al., "Induction of cytokeratin expression in human mesenchymal cells," *J. Cell Physiol.*, 1987, 133, 321-329.
Walboomers, X.F., et al., "Cell and tissue behavior on micro-grooved surfaces," *Odontology*, 2001, 89, 2-11.
Wang, D., et al., "Synthesis and characterization of a novel degradable phosphate-containing hydrogel," *Biomaterials*, 2003, 24, 3969-3980.
Wang, X., et al., "Cell fusion is the principal source of bone-marrow-derived hepatocytes," *Nature*, 2003, 422, 897-900.
Wegman, A., et al., "Nonsteroidal anti-inflammatory drugs or acetaminophen for osteoarthritis of the hip or knee? A synstematic review of evidence and guidelines," *J. Rheumatol.*, 2004, 31, 344-354.
Weiss, M.L., et al., "Transplantation of porcine umbilical cord matrix cells into the rat brain," *Exp. Neur.*, 2003, 182, 288-299.
Wobus, A.M., et al., "Retinoic acid accelerates embryonic stem cell-derived cardiac differentiation and enhances development of ventricular cardiomyocytes," *J. Mol. Cell Cardiol.*, 1997, 29, 1525-1539.
Woodbury, D., et al., "Adult rat and human bone marrow stromal cells differentiate into neurons," *J. of Neurosci. Res.*, 2000, 61, 364-370.
Xu, C., et al., "Characterization and enrichment of cardiomyocytes derived from human embryonic stem cells," *Circ. Res.*, 2002, 91, 501-508.
Yang, H., et al., "Region-specific differentiation of neural tube-derived neuronal restricted progenitor cells after heterotopic transplantation," *PNAS*, 2000, 97(24), 13366-13371.
Yip, H.K., et al., "Axonal regeneration of retinal ganglion cells: effect of trophic factors," *Prog. Retin Eye Res.*, 2000, 19(5), 559-575.
Yu, M., et al., "Mid-trimester fetal blood-derived adherent cells share characteristics similar to mesenchymal stem cells but full-term umbilical cord blood does not," *British J. of Haematology*, 2004, 124, 666-675.
Zangani, D., et al., "Multiple differentiation pathways of rat mammary stromal cells in vitro: acquisition of a fibroblast, adipocyte or endothelial phenotype is dependent on hormonal and extracellular matrix stimulation," *Differentiation*, 1999, 64, 91-101.
Zeng, B.Y., et al., "Regenerative and other responses to injury in the retinal stump of the optic nerve in adult albino rats: transaction of the intracranial optic nerve," *J. Anat.*, 1995, 186, 495-508.
Zhang, S.-C., et al., "In vitro differentiation of transplantable neural precursors from human embryonic stem cells," *Nature Biotechnology*, 2001, 19, 1129-1133.
Abbas, A.K., Lichtman, A.H., *Cellular and Molecular Immunology*, 5th Ed. (2003) Saunders, Philadelphia, p. 171.
Agbulut, O. et al., "Comparison of Human Skeletal Myoblasts and Bone Marrow-Derived CD133+ Progenitors for the Repair of Infarcted Myocardium," Journal of the American College of Cardiology, 2004, 44(2), 458-463.
Auda-Boucher, G., et al., "Staging of the commitment of murine cardiac cell progenitors," *Dev. Bio.*, 2000, 225(1), 214-225 (Abstract 2 pages).
Bao, Z.Z.., et al., "Regulation of chamber-specific gene expression in the developing heart by Irx4," *Science*, 1999, 283(5405), 1161-1164 (Abstract 1 page).
Bhindi, R. et al., "Rat models of myocardial infarction," *Thromb Haemost*, 2006, 96, 602-610.
Constantini, S., et al., "The effects of methylprednisolone and the ganglioside GM1 on acute spinal cord injury in rats," *J. Neurosurg.*, 1994, 80(1), 97-111 (Abstract 2 pages.
Dawson, T.M., et al., "Neuroprotective and neurorestorative strategies for Parkinson's disease," *Nat. Neurosci.*, 2002, 5 Suppl., 1058-1061 (Abstract 1 page).
Doyle, J., "Spiraling complexity, robustness, and fragility in biology," http://www.cds.caltech.edu/~doyle/CmplxNets/Biol.pdf, available online Feb. 28, 2004.

(56) References Cited

OTHER PUBLICATIONS

Eagle, H., "The specific amino acid requirements of a mammalian cell (strain L) in tissue culture," *J. Biol. Chem.*, Jun. 1955, 214(2), 839-852.

Eisenhofer, G., E., et al., "Tyrosinase: a developmentally specific major determinant of peripheral dopamine," *FASEB J.*, 2003, 1248-1255.

Goodwin, H. S. et al., "Multilineage differentiation activity by cells isolated from umbilical cord blood: Expression of bone, fat and neural markers," *Biology of Blood and Marrow Transplantation*, 2001, 7, 581-588.

Hill, M. et al., "Treatment for swallowing difficulties (dysphagia) in chronic muscle disease," *Cochrane Database Syst Rev.*, 2004, (2):CD004303.

Holz, F. G. et al., "Intraocular microablation of choroidal tissue by a 308 nm AIDA excimer laser for RPE-transplantation in patients with age-related macular degeneration," *Biomed Tech* (Berlin), Apr. 2003, 48(4), 82-85.

Ishii, M. et al., "Molecular markers distinguish bone marrow mesenchymal stem cells from fibroblasts," *Biochemical and Biophysical Research Communications*, Jun. 24, 2005, 332(1), 297-303.

Jaffe, E. A. et al., "Culture of human endothelial cells derived from umbilical veins," *J Clin Invest*, 1973, 52, 2745-2756.

Jomura, S., et al., "Potential Treatment of Cerebral Global Ischemia with Oct-4+ Umbilical Cord Matrix Cells," *Stem Cells*, Sep. 7, 2006, AlphaMed Press, Downloaded from www.StemCells.com at Ethicon, Inc. on Sep. 11, 2006 and Supplemental Data: 2 pages.

Joussen, A. M., "Cell transplantation in age related macular degeneration: current concepts and future hopes," *Graefe's Arch. Clin. Exp. Ophthalmol.*, 2004, 242, 1-2.

Klassen, H. et al., "Stem cells and retinal repair," *Prog. Retin. Eye Res.*, 2004, 23(2), 149-181 (Abstract 1 page).

Laface, D., et. al., "Genetransfer into hematopoietic progenitor cells mediated by an adeno-associated virus vector," *Virology*, 1998, 162, 483-486.

Langeggen, H. et al., "HUVEC take up opsonized zymosan particles and secrete cytokines IL-6 and IL-8 in vitro," *FEMS Immunol. Med. Microbiol.*, 2003, 36, 55-61.

Le Bouteiller, P., et al., "Soluble HLA-G1 at the materno-foetal interface—a review," *Placenta*, 2003, 24 (Suppl. A), S10-S15.

Lodie, T. A. et al., "Systematic Analysis of Reportedly Distinct Populations of Mulitpotent Bone Marrow-Derived Stem Cells Reveals a Lack of Distinction," *Tissue Engineering*, Oct. 2002, 8(5), 739-751.

Luyten, F. P. et al., "Skeletal tissue engineering: opportunities and challenges," *Best Pract. Res. Clin. Rheumatol.*, Dec. 2001, 15(5), 759-769.

MacDonald, R.J., "Expression of the pancreatic elastase I gene in transgenic mice," *Hepatology*, 1987, 7(1), 42S-51S.

Medicetty, S. et al., "Transplantation of Human Umbilical Cord Matrix Stem Cells Alleviates Apomorphine-Induced Rotations in Parkinsonian Rats", 2003, XP-002383776, 1 page, Society for Neuroscience Abstract Viewer and Itinerary Planner.

Merx, M. W. et al., "Transplantation of human umbilical vein endothelial cells improves left ventricular function in a rat model of myocardial infarction," *Basic Res. Cardiol.*, 2005, 100, 208-216.

Morgenstern, J. P., et al., "Advanced mammalian gene transfer: high titre retroviral vectors with multiple drug selection markers and a complementary helper-free packaging cell line," *Nucleic Acids Res.*, 1990, 18(12), 3587-3596.

Moulder, J. E., "Pharmacological intervention to prevent or ameliorate chronic radiation injuries," *Semin. Radiat. Oncol.*, 2003, 13, 73-84.

Nork, T. M. et al., "Swelling and Loss of Photoreceptors in Chronic and Experimental Glaucomas," *Arch. Ophthalmol.*, 2000, 118, 235-245.

Phipps, J. A. et al., "Paired-flash identification of rod and cone dysfunction in the diabetic rat," *Investigative Ophthalmology & Visual Science*, 2004, 45(12), 4592-4600.

Pittenger, M. F. et al., "Mesenchymal Stem Cells and Their Potential as Cardiac Therapeutics," *Circ. Res.*, 2004, 95, 9-20.

Reyes, M., et al., "Purification and ex vivo expansion of postnatal human marrow mesodermal progenitor cells," *Blood*, 2001, 98(9), 2615-2625.

Rezai, KA., et al., "Iris pigment epithelium transplantation," *Graefes Arch. Clin. Ophthalmol.*, 1997, 235, 558-562.

Rios, M., et al., "Catecholamine Synthesis is Mediated by Tyrosinase in the Absence Tyrosine Hydroxylase," *J. Neurosci.*, 1999, 3519-3526.

Salgado, A. J. et al., "Bone Tissue Engineering: State of the Art and Future Trends," *Macromol. Biosci.*, Aug. 2004, 4, 743-765.

Tremain, N. et al., "MicroSAGE Analysis of 2,353 Expressed Genes in a Single Cell-Derived Colony of Undifferentiated Human Mesenchymal Stem Cells Reveals mRNAs of Multiple Cell Lineages," *Stem Cells*, 2001, 19, 408-418.

Unigene entry for Hs.522632, *Homo sapiens* TMP metallopeptidase inhibitor 1 (TIMP1), printed from http://www.nebi.nlm.nih.gov/UniGene on Oct. 12, 2006.

Vajsar, J. et al., "Walker-Warburg syndrome," *Orphanet Journal of Rare Diseases*, 2006, 1, 29.

Vermot-Desroches, C. et al., "Heterogeneity of antigen expression among human umbilical cord vascular endothelial cells: identification of cell subsets by co-expression of haemopoietic antigens," *Immunol. Lett.*, 1995, 48, 1-9.

Weiss, M. L. et al., "Human umbilical cord matrix stem cells: preliminary characterization and effect of transplantation in a rodent model of Parkinson's disease," *Stem Cells*, 2006, 24, 781-792.

Xu, Y., et al., "Dopamine, in the presence of tyrosinase, covalently modifies and inactivates tyrosine hydroxylase," *J. Neurosci. Res.*, 1998, 54(5), 691-697 (Abstract, 3 pages).

Ye, Q. et al., "Recovery of Placental-Derived Adherent Cells with Mesenchymal Stem Cell Characteristics", 2001, 98(11), 147B, XP-009026843, Blood.

Yokoo, T. et al., "Stem cell gene therapy for chronic renal failure," *Curr Gene Ther.*, 2003, 3, 387-394.

Zuloff-Shani, A. et al., "Macrophage suspensions prepared from a blood unit for treatment of refractory human ulcers," *Transfus Apheresis Sci.* 2004, 30(2), 163-167.

Aldskogius, H. et al., "Strategies for repair of the deafferented spinal cord," *Brain Res. Rev.*, 2002, 20, 301-308.

Armulik A et al., "Endothelial/Pericyte Interactions," *Circ. Res.*, 2005, 97, 512-23.

Bergers G. et al., "The role of pericytes in blood-vessel formation and maintenance," *Neuro-Oncology*, 7, 452-464 2005.

Daley, G. Q. et al., "Realistic Prospects for Stem Cell Therapeutics," *Hematol.*, 2003, 398-418.

Kawata, M. et al., "Transcriptional control of HLA-A,B,C antigen in human placental cytotrophoblast isolated using trophoblast- and HLA-specific monoclonal antibodies and the fluorescence-activated cell sorter," *J. Exp. Med.*, Sep. 1984, 160, 633-651.

Kirschstein, R. et al., "Can stem cells repair a damaged heart?" *Stem Cells: Scientific Progress and Future Research Directions*, 2001, 87-92.

Lindvall, O. et al., "Stem cell therapy for human neurodegenerative disorders—how to make it work," *Nature Medicine*, Jul. 2004, 542-550.

Nishishita, T. et al., "A potential pro-angiogenic cell therapy with human placenta-derived mesenchymal cells," *Biochemical and Biophysical Research Communications*, 2004, 325, 24-31.

Rehman, J. et al., "Secretion of Angiogenic and Antiapoptotic Factors by Human Adipose Stromal Cells," *Circulation*, 2004, 109, 1292-1298.

Roskams, A. J. et al., "Directing stem cells and progenitor cells on the stage of spinal cord injury," *Exp. Neurol.*, 2005, 193, 267-272.

Urbich, C. et al., "Endothelial Progenitor Cells,", *Circ. Res.*, 2004, 95, 343-353.

Yang Chen et al., "Enhancement of neovascularization with cord blood CD133+ cell-derived endothelial progenitor cell transplantation," *Thrombosis and Haemostasis*, Jun. 2004, 91(6), 1202-1212.

Bergers G. et al., "The role of pericytes in blood-vessel formation and maintenance," Neuro-Oncology, 2005, 7, 452-464.

(56) References Cited

OTHER PUBLICATIONS

Blakemore, W. F. et al., "Modelling Large Areas of Demyelination in the Rat Reveals the Potential and Possible Limitations of Transplanted Glial Cells for Remyelination in the CNS," GLIA, 2002, 38, 155-168.
Franc, S. et al., "Microfibrillar composition of umbilical cord matrix: characterization of fibrillin, collagen VI and intact collagen V," Placenta, 1988, 19, 95-104.
Mackay et al., "Chondrogenic differentiation of cultured human mesenchymal stem cells from marrow," Tissue Engineering, 1998, 4(4), 415-428.
Schouten, J.W. et al., "A Review and Rationale for the Use of Cellular Transplantation as a Therapeutic Strategy for Traumatic Brain Injury," Journal of Neurotrauma, 2004, 21(11), 1501-1538.
Merriam-Webster Medline Plus Online Medical Dictionary, definitions of "iliac", "ilium" ileal/ileac and "ileum". [online] [retrieved on Feb. 13, 2008]. Retrieved from the Internet: URL://www.nlm.nih.gov/medlineplus/mplusdictionary.html.
Aggarwal et al., "Human Mesenchymal Stem Cells Modulate Allogeneic Immune Cell Responses," Blood, 2005; 105(4):1815-1822.
Aston, J. E., et al., "Repair of Articular Surfaces by Allografts of Articular and Growth-Plate Cartilage," *Journal of Bone and Joint Surgery*, 1986; 68-B(1):29-35.
Bai, M., et al, "Dimerization of the Extracellular Calcium-sensing Receptor (CaR) on the Cell Surface of CaR-Transfected HEK293 Cells," J. Biol Chem., 1998; 273(36): 23605-23610.
Bradley, B.A., "The Role of HLA Matching in Transplantation," Immunol. Lett., 1991; 29:55-59.
Bussolati et al., "Isolation of Renal Progenitor Cells from Adult Human Kidney," American Journal of Pathology, 2005; 166(2):545-555.
Carter, D. et al., "Characterization of MSC Potential to Treat GVHD Using Molecular Markers Linked to MSC-Mediated Immunosuppression In Vitro," Blood, 2005; 106(11) part 2, Abstract No. 4322, 160B.
"Cell Lysis, p. 2" http://www.piercenet.com/objects/view.cfm?type=Page&ID=1904ED25-8FA4-475C-8068-C2EB13D5F4E7; assessed Aug. 7, 2008.
Chen, J. et al., "Therapeutic Benefit of Intravenous Administration of Bone Marrow Stromal Cells after Cerebral Ischemia in Rats," Stroke, 2001; 32 (4) :1005-1011.
Dickinson, A.M. et al., "Non-HLA Immunogenetics in Hematopoietic Stem Cell Transplantation," Curr. Opin. Immunol., 2005; 17(5):517-525.
Fernandes, A.M. et al., "Mouse Embryonic Stem Cell Expansion in a Microcarrier-based Stirred Culture System," Journal of Biotechnology, 2007; 132(2): 227-236.
Gröhn, P. et al., "Collagen-coated BA2+-Alginate Microcarriers for the Culture of Anchorage-Dependent Mammalian Cells," BioTechniques, 1997; 22(5): 970-975.
Gupta, S. et al., "Isolation and Characterization of Kidney-Derived Stem Cells," J. of Am. Soci. of Nephrol., 2006; 17(11):3028-3040.
Herrera, M.B. et al., "Mesenchymal Stem Cells Contribute to the Renal Repair of Acute Tubular Epithelial Injury," Int. J. Mol. Med., 2004; 14(6):1035-1041.
Hill, D.P. et al., "Screening for Novel Pattern Formation Genes Using Gene Trap Approaches," Methods in Enzymology, 1993; 225:664-681.
Hishikawa, K. et al., "Musculin/MyoR is Expressed in Kidney Side Population Cells and Can Regulate Their Function," Journal of Cell Biology, 2005; 169(6):921-928.
In'T Anker, P., et al., "Isolation of Mesenchymal Stem Cells of Fetal or Maternal Origin from Human Placenta," Stem Cells, 2004; 22:1338-1345.
Jones, J. et al., "Insulin-Like Growth Factors and Their Binding Proteins: Biological Actions," Endocrine Review, 1995; 16 (1) :3-34.
Jørgensen, N.R. et al., "Intercellular Calcium Signaling Occurs Between Human Osteoblasts and Osteoclasts and Requires Activation of Osteoclast P2X7 Receptors," The Journal of Biological Chemistry, 2002; 277(9): 7574-7580.
Kisiday, J. et al., "Self-Assembling Peptide Hydrogel Fosters Chondrocyte Extracellular Matrix Production and Cell Division: Implications for Cartilage Tissue Repair," PNAS, 2002; 99(15):9996-10001.
Kurtz, A. et al., "Activity in Fetal Bovine Serum that Stimulates Erythroid Colony Formation in Fetal Mouse Livers is Insulinlike Growth Factor I," J. Clin. Invest., 1985; 76;1643-1648.
Kushida, A., et al., "Decrease in Culture Temperature Releases Monolayer Endothelial Cell Sheets Together with Deposited Fibronectin Matrix from Temperature-Responsive Culture Surfaces," J. of Biomedical Materials Research, 1999; 45(4):355-362.
Li, C.D. et al, "Mesenchymal Stem Cells Derived From Human Placenta Suppress Allogeneic Umbilical Cord Blood Lymphocyte Proliferation," Cell Research, 2005; 15(7):539-547.
Li, Y. et al., "Intact, Injured, Necrotic and Apoptotic Cells after Focal Cerebral Ischemia in the Rat," J. Neurol. Sci., 1998; 156(2):119-132.
Li, Y. et al., "Ultrastructural and Light Microscopic Evidence of Apoptosis after Middle Cerebral Artery Occlusion in the Rat " Am. J. Pathol., 1995; 146(5):1045-1051.
Lindenlaub, T. et al., "Partial Sciatic Nerve Transection as a Model of Neuropathic Pain: A Qualitative and Quantitative Stud ," PAIN, 2000; 89(1): 97-106.
Ma, L. et al., "Human Umbilical Cord Wharton's Jelly-Derived Mesenchymal Stem Cells Differentiation into Nerve-Like Cells," Chinese Med. Jour., 2005; 118(23):1987-1993.
Ma, P.X . et al., "Synthetic Nano-Scale Fibrous Extracellular Matrix ," J. Biomed Mater Res., 1999; 46(1):60-72.
Maeshima, A. et al., "Adult Kidney Tubular Cell Population Showing Phenotypic Plasticity, Tubulogenic Capacity, and Integration Capability into Developing Kidney," Journal of American Society of Nephrology , 2006; 17(1):188-198.
Merriam Webster Medline Plus Online Medical Dictionary, definitions of "undifferentiated," and "differentiate," and "differentiation." Retrieved online Mar. 6, 2007, URL:www.nlm.nih.gov/medlineplus/mplusdictionary.html.
Melero-Martin, J. et al., "Optimal in Vitro Expansion of Chondroprogenitor Cells in Monolayer Culture," Biotechnology and Bioengineering, 2006; 93(3):519-533.
Moore, A.E. et al., "Parkinsonian Motor Deficits are Reflected by Proportional A9/A10 Dopamine Neuron Degeneration in the Rat," Exp. Neurol., 2001; 172(2):363-376.
Morigi, M. et al., "Mesenchymal Stem Cells are Renotropic, Helping to Repair the Kidney and Improve Function in Acute Renal Failure," J. Am. Soc. Nephrol., 2004; 15(7):1794-1804.
Morishima, Y. et al., "The Clinical Significance of Human Leukocyte Antigen (HLA) Allele Compatibility in Patients Receiving a Marrow Transplant from Serologically HLA-A, HLA-B, and HLA-DR Matched Unrelated Donors," Blood, 2002; 99(11):4200-4206.
Newman, K.D. et al., "Poly(D,L lactic-co-glycolic acid) Microspheres as Biodegradable Microcarriers for Pluripotent Stem Cells," Biomaterials, 2004; 25:5763-5771.
Oliver, J.A. et al., "The Renal Papilla is a Niche for Adult Kidney Stem Cells," J. Clin Invest., 2004, 114(6):795-804.
Panepucci, R.A. et al., "Comparison of Gene Expression of Umbilical Cord Vein and Bone Marrow-Derived Mesenchymal Stem Cells," Stem Cells, 2004; 22(7):1263-1278.
Pera, M.F. et al., "Human Embryonic Stem Cells", J. Cell Science, 2000; 113:5-10.
Pisharodi, M. et al., "An Animal Model for Neuron-Specific Spinal Cord Lesions by the Microinjection of N-Methylaspartate, Kainic Acid, and Quisqualic Acid," 1985; Appl. Neurophysiology 48:226-233.
Pittenger, M.F. et al., Multilineage potential of adult human mesenchymal stem cells. Science, 1999, 284:143-147.
Plaia, T., et al., "Characterization of a New Nih-Registered Variant Human Embryonic Stem Cell Line, BG01V: A Tool for Human Embryonic Stem Cell Research," Stem Cells, 2006: 24(3): 531-546.
Russo, E., Cultivating Policy from Cell Types, The Scientist, 2001; 15(11):6 (printout is numbered 1-6).

(56) References Cited

OTHER PUBLICATIONS

Sagrinati, C. et al., "Isolation and Characterization of Multipotent Progenitor Cells from the Bowman's Capsule of Adult Human Kidney," Journal of American Society of Nephrology, 2006; 17(9)2443-2456.
Schallert, T. et al., "Use-Dependent Structural Events in Recovery of Function," Brain Plasticity, Adv. Neurol., 1997; 73:229-238.
Schreuder, G.M. et al., "The HLA Dictionary 1999: A Summary of HLA-A, -B, -C, -DRB1/3/4/5, -DQB1 Alleles and Their Association with Serologically Defined HLA-A, -B, -C, -DR and -DQ Antigens," Tissue Antigens, 1999; 54 (4):409-437.
Sethe, S. et al., "Aging of Mesenchymal Stem Cells," Ageing Research Reviews, 2006; 5:91-116.
Shimizu, T. et al., "Fabrication of Pulsatile Cardiac Tissue Grafts Using a Novel 3-Dimensional Cell Sheet Manipulation Technique and Temperature-Responsive Cell Culture Surfaces," Circulation Research, 2002; 90(3):e40-e48.
Shuto, T. et al., "Dexamethasone Stimulates Osteoclast-Like Cell Formation by Inhibiting Granulocyte-Macrophage Colony-Stimulating Factor Production in Mouse Bone Marrow Cultures," Endocrinology, 1994; 134(3):1121-1126.
Song, H. et al., "Astroglia Induce Neurogenesis From Adult Neural Stem Cells," Nature, 2002; 417(6884):39-44.
Tao, W., "Application of Encapsulated Cell Technology for Retinal Degenerative Disease," Expert. Opin. Biol. Ther., 2006; 6(7): 717-726.
Toma, C. et al., "Human Mesenchymal Stem Cells Differentiate to a Cardiomyocyte Phenotype in the Adult Murine Heart," Circulation 2002; 105:93-98.
Turner, D., "The Human Leucocyte Antigen (HLA) System," Vox Sang., 2004; 87(Suppl 1):S87-S90.
Ujike, H. et al., "Gene Expression Related to Synaptogenesis, Neuritogenesis, and MAP Kinase in Behavioral Sensitization to Psychostimulants," Ann. N.Y. Acad. Sci., 2002; 965:55-67.
Ulloa-Montoya, F. et al., "Culture Systems for Pluripotent Stem Cells," Journal of Bioscience and Bioengineering, 2005. 100(1):12-27.
Webster, T.J. et al., "Nanoceramic Surface Roughness Enhances Osteoblast and Osteoclast Functions for Improved Orthopaedic/Dental Implant Efficacy," Scripta Materialia, 2001; 44(8/9):1639-1642.
Wenning, G.K. et al., "Neural Transplantation in Animal Models of Multiple System Atrophy: A Review," J. Nueral Transm., 1999; Suppl.(55):103-113.
Wikipedia, Definition of "Iliac crest" provided by Wikipedia, the free encyclopedia; retrieved from the Internet at URL: http://en.wikipedia.org/wiki/Iliac_crest; downloaded on Dec. 18, 2007.
Williams, J.T. et al., "Cells Isolated From Adult Human Skeletal Muscle Capable of Differentiating Into Multiple Mesodermal Phenotypes," Am. Surg. Jan. 1999:65(I):22-6.
Wolford, L.M. et al., "Considerations in Nerve Repair," BUMC Proceedings, 2003; 16:152-156.
Xu, A. et al.,"Soft, Porous Poly(D,L lactide-co-glycotide) Microcarriers Designed for Ex Vivo Studies and for Transplantation of Adherent Cell Types including Progenitors," Annals of the New York Academy of Sciences, 2001, vol. 944: 144-159.
Yamashima, T., "Implication of Cysteine Proteases Calpain, Cathepsin and Caspase in Ischemic Neuronal Death of Primates," Progress in Neurobiology, 2000; 62:273-295.
Zhang, L. et al., "A Test for Detecting Long-Term Sensorimotor Dysfunction in the Mouse after Focal Cerebral Ischemia," J. Neurosci. Methods, 2002; 117(2):207-14.
Zhang, X. et al., "Efficient Adeno-Associated Virus-Mediated Gene Expression in Human Placenta-Derived Mesenchymal Cells," Microbiol. Immunol., 2003; 47(1):109-116.
Zhang, Y. et al., "Comparison of Mesenchymal Stem Cells from Human Placenta and Bone Marrow," Chinese Medical Journal, 2004; 117(6):882-887.
Zhang, Z.G. et al., "Correlation of VEGF and Angiopoietin Expression with D-ISRuption of Blood-Brain Barrier and Angiogenesis after Focal Cerebral Ischemia," J. Cereb. Blood Flow Metab., 2002; 22(4):379-392.
Zimmerman, S. et al., "Lack of Telomerase Activity in Human Mesenchymal Stem Cells," Leukemia, 2003; 17:1146-1149.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 11/315,897, dated Jun. 13, 2008, 12 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated. Nov. 20, 2006, 24 pages.
In the U.S. Patent and Trademark Office, Non-Final Office Action in re: U.S. Appl. No. 10/877,269, dated Jan. 17, 2008, 10 pages.
In the U.S. Patent and Trademark Office, Final Office Action in re: U.S. Appl. No. 10/877,269, dated Aug. 14, 2007, 6 pages.
In the U.S. Patent and Trademark Office, Non-Final Office Action in re: U.S. Appl. No. 10/877,269, dated May 3, 2007, 12 pages.
In the U.S. Patent and Trademark Office, Non-Final Office Action in re: U.S. Appl. No. 11/315,898, dated Feb. 13, 2008, 12 pages.
In the U.S. Patent and Trademark Office, Final Office Action in re: U.S. Appl. No. 11/315,943, dated Aug. 20, 2008, 7 pages.
In the U.S. Patent and Trademark Office, Non-Final Office Action in re: U.S. Appl. No. 11/315,943, dated Feb. 12, 2008, 11 pages.
In the U.S. Patent and Trademark Office, Non-Final Office Action in re: U.S. Appl. No. 10/877,541, dated Jul. 25, 2007, 13 pages.
In the U.S. Patent and Trademark Office, Advisory Office Action in re: U.S. Appl. No. 10/877,541, dated Apr. 18, 2007, 4 pages.
In the U.S. Patent and Trademark Office, Final Office Action in re: U.S. Appl. No. 10/877,541, dated Jan. 10, 2007, 19 pages.
In the U.S. Patent and Trademark Office, Non-Final Office Action in re: U.S. Appl. No. 10/877,541, dated Feb. 22, 2006, 13 pages.
In the U.S. Patent and Trademark Office, Advisory Office Action in re: U.S. Appl. No. 11/317,574, dated Jun. 4, 2008, 3 pages.
In the U.S. Patent and Trademark Office, Final Office Action in re: U.S. Appl. No. 11/317,574, dated Mar. 5, 2008, 10 pages.
In the U.S. Patent and Trademark Office, Final Office Action in re: U.S. Appl. No. 11/317,574, dated Aug. 10, 2007, 14 pages.
In the U.S. Patent and Trademark Office, Non-Final Office Action in re: U.S. Appl. No. 10/877,009 dated Jan. 9, 2008, 12 pages.
In the U.S. Patent and Trademark Office, Final Office Action in re: U.S. Appl. No. 10/877,009, dated Jul. 25, 2007, 17 pages.
In the U.S. Patent and Trademark Office, Non-Final Office Action in re: U.S. Appl. No. 10/877,009, dated Nov. 21, 2006, 15 pages.
In the U.S. Patent and Trademark Office, Non-Final Office Action in re: U.S. Appl. No. 10/876,998, dated Jun. 25, 2008, 9 pages.
In the U.S. Patent and Trademark Office, Final Office Action in re: U.S. Appl. No. 10/876,998, dated Feb. 27, 2008, 18 pages.
In the U.S. Patent and Trademark Office, Non-Final Office Action in re: U.S. Appl. No. 10/876,998, dated Jul. 13, 2007, 30 pages.
In the U.S. Patent and Trademark Office, Final Office Action in re: U.S. Appl. No. 10/876,998, dated Oct. 18, 2006, 29 pages.
In the U.S. Patent and Trademark Office, Non-Final Office Action in re: U.S. Appl. No. 10/876,998, dated Mar. 30, 2006, 24 pages.
In the U.S. Patent and Trademark Office, Non-Final Office Action in re: U.S. Appl. No. 11/321,863, dated Aug. 19, 2008, 15 pages.
In the U.S. Patent and Trademark Office, Non-Final Office Action in re: U.S. Appl. No. 11/322,003, dated Jun. 2, 2008, 14 pages.
In the U.S. Patent and Trademark Office, Non-Final Office Action in re: U.S. Appl. No. 11/321,864, dated Apr. 21, 2008, 7 pages.
In the U.S. Patent and Trademark Office, Final Office Action in re: U.S. Appl. No. 11/315,969, dated May 19, 2008, 9 pages.
In the U.S. Patent and Trademark Office, Non-Final Office Action in re: U.S. Appl. No. 11/315,969, dated Nov. 1, 2007, 1 page.

(56) References Cited

OTHER PUBLICATIONS

In the U.S. Patent and Trademark Office, Non-Final Office Action in re: U.S. Appl. No. 11/297,778, dated Feb. 22, 2007, 14 pages.
In the U.S. Patent and Trademark Office, Final Office Action in re: U.S. Appl. No. 11/297,778, dated Apr. 11, 2008, 9 pages.
In the U.S. Patent and Trademark Office, Final Office Action in re: U.S. Appl. No. 11/304,091, dated Apr. 11, 2008, 11 pages.
In the U.S. Patent and Trademark Office, Non-Final Office Action in re: U.S. Appl. No. 11/304,091, dated Feb. 23, 2007, 9 pages.
In the United States Patent and Trademark Office, Final Office Action in re: U.S. Appl. No. 11/315,898, dated Sep. 16, 2008, 19 pages.
In the United States Patent and Trademark Office, Non-Final Office Action in re: U.S. Appl. No. 11/322,372, dated Sep. 3, 2008, 45 pages.
In the United States Patent and Trademark Office, Non-Final Office Action, in re: U.S. Appl. No. 11/297,156, dated Oct. 10, 2008, 36 pages.
In the United States Patent and Trademark Office, Non-Final Office Action in re: U.S. Appl. No. 11/317,574, dated Sep. 30, 2008, 26 pages.
In the U. S. Patent and Trademark Office, Non-Final Office Action in re: U.S. Appl. No. 11/315,969, dated Dec. 23, 2008, 18 pages.
In the U. S. Patent and Trademark Office, Non-Final Office Action in re: U.S. Appl. No. 11/321,864, dated Jan. 8, 2009, 34 pages.
In the United States Patent and Trademark Office, Non-Final Office Action in re: U.S. Appl. No. 11/315,943, dated Feb. 20, 2009, 17 pages.
In the United States Patent and Trademark Office, Non-Final Office Action in re: U.S. Appl. No. 11/481,481, dated Mar. 20, 2009, 48 pages.
In the United States Patent and Trademark Office, Final Office Action in re: U.S. Appl. No. 11/315,897, dated Mar. 20, 2009, 21 pages.
In the United States Patent and Trademark Office, Non-Final Office Action in re: U.S. Appl. No. 11/481,480, dated Mar. 20, 2009, 50 pages.
In the United States Patent and Trademark Office, Final Office Action in re: U.S. Appl. No. 11/321,863, dated Feb. 12, 2009, 24 pages.
In the United States Patent and Trademark Office, Final Office Action in re: U.S. Appl. No. 11/322,003 dated Feb. 13, 2009, 24 pages.
In the United States Patent and Trademark Office, Final Office Action in re: U.S. Appl. No. 10/876,998 dated Feb. 13, 2009, 25 pages.
In the United States Patent and Trademark Office, Final Office Action in re: U.S. Appl. No. 11/322,372 dated Feb. 13, 2009, 46 pages.
In the U. S. Patent and Trademark Office, Non-Final Office Action in re: U.S. Appl. No. 11/481,456 dated Apr. 16, 2009, 50 pages.
In the U. S. Patent and Trademark Office, Non-Final Office Action in re: U.S. Appl. No. 11/317,574 dated Apr. 29, 2009, 29 pages.
In the U. S. Patent and Trademark Office, Final Office Action in re: U.S. Appl. No. 11/315,969 dated May 15, 2009, 7 pages.
In the U. S. Patent and Trademark Office, Non-Final Office Action in re: U.S. Appl. No. 11/315,898 dated Feb. 18, 2009, 18 pages.
In the U. S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/322,372 dated Aug. 6, 2009, 13 pages.
In the U. S. Patent and Trademark Office, Final Office Action in re: U.S. Appl. No. 11/322,372 dated Aug. 31, 2010, 11 pages.
In the U. S. Patent and Trademark Office, Non-Final Office Action in re: U.S. Appl. No. 11/322,372 dated Jan. 21, 2010, 10 pages.
In the U. S. Patent and Trademark Office, Non-Final Action in re: U.S. Appl. No. 10/876,998 dated Feb. 1, 2011, 11 pages.
In the U. S. Patent and Trademark Office, Non-Final Action in re: U.S. Appl. No. 11/481,456 dated Feb. 3, 2011, 10 pages.
In the U. S. Patent and Trademark Office, Non-Final Action in re: U.S. Appl. No. 11/481,481 dated Feb. 3, 2011, 10 pages.
In the U. S. Patent and Trademark Office, Non-Final Action in re: U.S. Appl. No. 12/389,305 dated Feb. 8, 2011, 14 pages.
In the U. S. Patent and Trademark Office, Non-Final Action in re: U.S. Appl. No. 11/481,480 dated Feb. 3, 2011, 10 pages.
In the U.S. Patent and Trademark Office, Final Office Action in re: U.S. Appl. No. 10/877,446 dated Nov. 2, 2011, 12 pages.
In the U.S. Patent and Trademark Office, Final Office Action in re: U.S. Appl. No. 12/389,305 dated Oct. 12, 2011, 12 pages.
In the U.S. Patent and Trademark Office, Final Office Action in re: U.S. Appl. No. 12/429,849 dated Mar. 20, 2012, 9 pages.
In the U. S. Patent and Trademark Office, Final Action in re: U.S. Appl. No. 11/481,456 dated Oct. 11, 2011, 6 pages.
In the U. S. Patent and Trademark Office, Final Action in re: U.S. Appl. No. 10/877,446 dated Nov. 2, 2011, 12 pages.
In the U.S. Patent and Trademark Office, Non-Final Office Action in re: U.S. Appl. No. 12/697,081 dated Apr. 2, 2012, 8 pages.
In the U.S. Patent and Trademark Office, Non-Final Office Action in re: U.S. Appl. No. 13/605,716 dated Feb. 13, 2013, 13 pages.
Bakhshi, et al. "Mesenchymal stem cells from the Wharton's jelly of umbilical cord segments provide stromal support for the maintenance of cord blood hematopoietic stem cells during long-term ex vivo culture", Transfusion, 2008; 48: 2638-2644.
Cell Isolation Theory, in Tissue Dissociation Guide, Worthington Biochemical, accessible at http://www.tissuedissociation.com, accessed Aug. 8, 2007.
Draper et al., "Surface Antigens of Human Embryonic Stem Cells: Changes Upon Differentiation in Culture," J. Anat., 2002; 200:249-258.
Igura et al. "Human Placental Derived Stem Cells Differentiate into Neural Cells," Blood , 2002; 100(11): 517A (Abstract 2021).
Kusama et al., "Growth and morphogenesis of mouse prostate epithelial cells in collagen gel matrix culture" Cell Biol Int Rep, 1989; 13:569-575.
Makino et al., "Cardiomyocytes can be generated from marrow stromal cells in vitro," J. Clin. Invest., 1999; 103:697-705[1 ].
Naughton et al., "Cells isolated from Wharton's jelly of the human umbilical cord develop a cartilage phenotype when treated with TGF-b in vitro," 1997; FASEB J 11:A19 (Abstract 108).
Seaver et al. "The chick oviduct in tissue culture. I. Initial characterization of growing primary oviduct tissue cultures," Exp. Cell Res., 1984; 155: 241-251.
Seiji, T. et al., Possibility of Regenerative Medicine Using Human Amniotic Cells, Regenerative Medicine, 2002; 1(2):79-85.
Shake et al., "Mesenchymal stem cell implantation in a swine myocardial infarct model: engraftment and functional effects," Ann Thorac Surg, 2002; 73:1919-1926.
Wang, Y. et al., "Enhanced Recovery of Hematopoietic Progenitor and Stem Cells from Cultivated, Postpartum Human Placenta," Blood, 2001; 98(11): 183a (Abstract 769 ).
In the U. S. Patent and Trademark 0ffice, Advisory Action in re: U.S. Appl. No. 11/315,969 dated Sep. 29, 2009, 9 pages.
In the U. S. Patent and Trademark Office, Advisory Action in re: U.S. Appl. No. 11/322,372 dated May 12, 2009, 10 pages.
In the U. S. Patent and Trademark Office, Final Office Action in re: U.S. Appl. No. 11/481,456 dated Oct. 9, 2009, 11 pages.
In the U. S. Patent and Trademark Office, Final Office Action in re: U.S. Appl. No. 11/321,863 dated Aug. 7, 2009, 11 pages.
In the U. S. Patent and Trademark Office, Final Office Action in re: U.S. Appl. No. 11/321,864 dated Aug. 17, 2009, 13 pages.
In the U. S. Patent and Trademark Office, Non-Final Office Action in re: U.S. Appl. No. 11/317,574 dated Dec. 28, 2009, 26 pages.
In the U. S. Patent and Trademark Office, Non-Final Office Action in re: U.S. Appl. No. 11/321,863 dated Jan. 7, 2010, 13 pages.
In the U.S. Patent and Trademark Office, Non-Final Office Action in re: U.S. Appl. No. 11/321,864 dated Jan. 27, 2010, 12 pages.
In the U.S. Patent and Trademark Office, Non-Final Office Action in re: U.S. Appl. No. 11/315,969 dated Jan. 27, 2010, 12 pages.
In the U. S. Patent and Trademark Office, Non-Final Office Action in re: U.S. Appl. No. 11/315,943 dated Feb. 19, 2010, 13 pages.
In the U. S. Patent and Trademark Office, Final Office Action in re: U.S. Appl. No. 11/316,104 dated Mar. 24, 2010, 12 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Final Office Action in re: U.S. Appl. No. 11/315,897 dated May 14, 2010, 13 pages.

(56) References Cited

OTHER PUBLICATIONS

In the U. S. Patent and Trademark Office, Non-Final Office Action in re: U.S. Appl. No. 11/481,480 dated May 17, 2010, 10 pages.
In the U. S. Patent and Trademark Office, Non-Final Office Action in re: U.S. Appl. No. 10/876,998 dated Aug. 3, 2010, 14 pages.
In the U. S. Patent and Trademark Office, Final Office Action in re: U.S. Appl. No. 11/321,863 dated Aug. 17, 2010, 15 pages.
In the U. S. Patent and Trademark Office, Final Office Action in re: U.S. Appl. No. 11/321,864 dated Aug. 31, 2010, 7 pages.
In the U. S. Patent and Trademark Office, Final Office Action in re: U.S. Appl. No. 11/315,969 dated Aug. 31, 2010, 6 pages.
In the U. S Patent and Trademark Office, Non-Final Office Action in re: U.S. Appl. No. 11/316,104 dated Sep. 21, 2010, 13 pages.
In the U. S. Patent and Trademark Office, Final Office Action in re: U.S. Appl. No. 11/317,574 dated Oct. 6, 2010, 16 pages.
In the U. S. Patent and Trademark Office, Non-Final Office Action in re: U.S. Appl. No. 12/054,718 dated Sep. 29, 2010, 18 pages.
In the U. S. Patent and Trademark Office, Final Office Action in re: U.S. Appl. No. 11/481,481 dated Sep. 18, 2009, 11 pages.
In the U. S. Patent and Trademark Office, Advisory Action in re: U.S. Appl. No. 11/315,897 dated Jun. 30, 2009, 3 pages.
In the U. S. Patent and Trademark Office, Non-Final Action in re: U.S. Appl. No. 11/315,897 dated Sep. 2, 2009, 12 pages.
In the U. S. Patent and Trademark Office, Final Action in re: U.S. Appl. No. 11/481,480 dated Sep. 17, 2009, 12 pages.
In the U. S. Patent and Trademark Office, Final Action in re: U.S. Appl. No. 10/877,446 dated Jun. 4, 2010, 17 pages.
In the U. S. Patent and Trademark Office, Non-Final Action in re: U.S. Appl. No. 11/316,104 dated Oct. 31, 2008, 15 pages.
In the U. S. Patent and Trademark Office, Final Action in re: U.S. Appl. No. 10/876,998 dated May 27, 2009, 14 pages.
In the U. S. Patent and Trademark Office, Non-Final Action in re: U.S. Appl. No. 10/876,998 dated Nov. 24, 2009, 7 pages.
In the U. S. Patent and Trademark Office, Final Action in re: U.S. Appl. No. 11/322,003 dated Feb. 13, 2009, 17 pages.
Diad et al, "Human Umbilical Cord Mesenchymal Stem Cells: Osteogenesis In Vivo as Seed Cells for Bone Tissue Engineering," *J. BioMed Mater Res.*, 2008; 91A:123-131.
Haynesworth et al., "Cell Surface Antigens on Human Marrow-Derived Mesenchymal Cells are Detected by Monoclonal Antibodies," *Bone*, 1992; 13:69-80.

* cited by examiner

SEQUENCE LISTING

```
<160> NUMBER OF SEQ ID NOS: 10

<210> SEQ ID NO 1
<211> LENGTH: 22
<212> TYPE: DNA
<213> ORGANISM: Artificial
<220> FEATURE:
<223> OTHER INFORMATION: Synthetic Construct

<400> SEQUENCE: 1
gagaaatcca aagagcaaat gg                                              22

<210> SEQ ID NO 2
<211> LENGTH: 21
<212> TYPE: DNA
<213> ORGANISM: Artificial
<220> FEATURE:
<223> OTHER INFORMATION: Synthetic Construct

<400> SEQUENCE: 2
agaatggaaa actggaatag g                                               21

<210> SEQ ID NO 3
<211> LENGTH: 20
<212> TYPE: DNA
<213> ORGANISM: Artificial
<220> FEATURE:
<223> OTHER INFORMATION: Synthetic Construct

<400> SEQUENCE: 3
tcttcgatgc ttcggattcc                                                 20
```

<210> SEQ ID NO 4
<211> LENGTH: 21
<212> TYPE: DNA
<213> ORGANISM: Artificial
<220> FEATURE:
<223> OTHER INFORMATION: Synthetic Construct

<400> SEQUENCE: 4
gaattctcgg aatctctgtt g                                              21

<210> SEQ ID NO 5
<211> LENGTH: 21
<212> TYPE: DNA
<213> ORGANISM: Artificial
<220> FEATURE:
<223> OTHER INFORMATION: Synthetic Construct

<400> SEQUENCE: 5
ttacaagcag tgcagaaaac c                                              21

<210> SEQ ID NO 6
<211> LENGTH: 22
<212> TYPE: DNA
<213> ORGANISM: Artificial
<220> FEATURE:
<223> OTHER INFORMATION: Synthetic Construct

<400> SEQUENCE: 6
agtaaacatt gaaaccacag cc                                             22

<210> SEQ ID NO 7
<211> LENGTH: 20
<212> TYPE: DNA
<213> ORGANISM: Artificial
<220> FEATURE:
<223> OTHER INFORMATION: Synthetic Construct

<400> SEQUENCE: 7
tctgcagctc tgtgtgaagg                                                20

<210> SEQ ID NO 8
<211> LENGTH: 22
<212> TYPE: DNA
<213> ORGANISM: Artificial
<220> FEATURE:
<223> OTHER INFORMATION: Synthetic Construct

<400> SEQUENCE: 8
cttcaaaaac ttctccacaa cc                                             22

<210> SEQ ID NO 9
<211> LENGTH: 17
<212> TYPE: DNA
<213> ORGANISM: Artificial
<220> FEATURE:
<223> OTHER INFORMATION: Synthetic Construct

<400> SEQUENCE: 9
cccacgccac gctctcc                                                   17

<210> SEQ ID NO 10
<211> LENGTH: 19
<212> TYPE: DNA
<213> ORGANISM: Artificial
<220> FEATURE:
<223> OTHER INFORMATION: Synthetic Construct

<400> SEQUENCE: 10
tcctgtcagt tggtgctcc                                                                 19

POSTPARTUM-DERIVED CELLS FOR USE IN TREATMENT OF DISEASE OF THE HEART AND CIRCULATORY SYSTEM

CROSS-REFERENCE TO RELATED APPLICATIONS

This application claims the benefit of U.S. Provisional Application Ser. No. 60/483,264, filed Jun. 27, 2003, the entire contents of which are incorporated by reference herein. Other related applications include the following commonly-owned, co-pending applications, the entire contents of each of which are incorporated by reference herein: U.S. application Ser. No. 10/877,012, filed Jun. 25, 2004, now U.S. Pat. No. 7,510,873; U.S. application Ser. No. 10/877,446, filed Jun. 25, 2004; U.S. application Ser. No. 10/877,269, filed Jun. 25, 2004, now U.S. Pat. No. 7,524,489; Ser. No. 10/877,541, filed Jun. 25, 2004, now U.S. Pat. No. 7,413,734; U.S. application Ser. No. 10/877,009, filed Jun. 25, 2004, now U.S. Pat. No. 7,560,276; U.S. application Ser. No. 10/876,998, filed Jun. 25, 2004; and U.S. Provisional Application No. 60/555,908, filed Mar. 24, 2004.

FIELD OF THE INVENTION

The invention relates to postpartum-derived cells that have the potential to divide, and to differentiate along mesenchymal lineage, towards cardiomyogenic, angiogenic and vasculogenic phenotypes. The invention also relates to methods for the use of such postpartum-derived cells in therapeutic treatment of diseases of the heart and circulatory system.

BACKGROUND OF THE INVENTION

It is generally recognized that the cells which comprise the heart muscle in mammals are post-mitotic. This leads to difficulties in injured or diseased heart muscles, which are largely unable to repair damaged cells that become necrotic. After such damage, the efficiency and output of the heart muscle are decreased, placing additional stress on the heart, leading to further damage and necrosis, and ultimately to heart failure.

The downward spiral from healthy heart to failing heart can result from a number of conditions including physical injury, heart disease, including congenital heart disease, and infections of the heart or circulatory tissue. Diseases of the heart and circulatory system are often ultimately fatal, particularly conditions which result in heart failure, for example cardiomyopathies. At present there is no cure for most such conditions and many patients require, for example, ventricular assist devices and eventually heart transplants.

Presently, there is interest in using either stem cells, which can divide and differentiate, or muscles cells from other sources, including smooth and skeletal muscles cells, to assist the heart to repair or reverse tissue damage, restore function, or to at least halt the damage cycle leading to further loss of healthy heart tissue. In addition many circulatory diseases and injuries involve chronic or acute damage to, or necrosis of, circulatory tissues, and the cells of which such tissues are comprised. Cell-based and cell-derived therapies are of interest for these conditions.

There is thus a need in the art for cell-based, or cell-derived therapies which can aid in healing damaged heart or circulatory tissues, or which can result in the repair or replacement of such damage in a patient.

SUMMARY OF THE INVENTION

The invention, in one of its aspects is generally directed to isolated postpartum-derived cells which are derived from postpartum tissue which is substantially free of blood and which is capable of self-renewal and expansion in culture and having the potential to differentiate along mesenchymal lineage, towards cardiomyogenic, angiogenic and vasculogenic phenotypes, and further towards cells such as cardiomyocytes, endothelial cells, myocardial cells, epicardial cells, vascular endothelial cells, smooth muscle cells (e.g. vascular smooth muscle cells), as well as cells of the excitatory and conductive systems, and progenitors or more primitive relatives of the foregoing. The invention, in other aspects, is directed to populations of cells comprising such cells, and therapeutic cell compositions, as well as methods of using the populations of cells for therapeutic treatment of cardiac or circulatory damage or disease In a first aspect, the invention provides isolated postpartum-derived cells comprising L-valine-requiring cells derived from postpartum tissue substantially free of blood. The cells are capable of self-renewal and expansion in culture and have the potential to differentiate into cells of other phenotypes; for example cardiomyocytes, or their progenitors. The cells are capable of growth in atmospheres containing oxygen from about 5% to at least about 20% and comprise at least one of the following characteristics:

the potential for at least about 40 doublings in culture;

attachment and expansion on a coated or uncoated tissue culture vessel, wherein a coated tissue culture vessel comprises a coating of gelatin, laminin, collagen, polyornithine, vitronectin, or fibronectin;

production of at least one of tissue factor, vimentin, and alpha-smooth muscle actin;

production of at least one of CD10, CD13, CD44, CD73, CD90, PDGFr-alpha, PD-L2 and HLA-A,B,C;

lack of production of at least one of CD31, CD34, CD45, CD80, CD86, CD117, CD141, CD178, B7-H2, HLA-G, and HLA-DR,DP,DQ, as detected by flow cytometry;

expression of at least one of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3;

expression of at least one of C-type (calcium dependent, carbohydrate-recognition domain) lectin, superfamily member 2 (activation-induced); Wilms tumor 1; aldehyde dehydrogenase 1 family, member A2; and renin; oxidized low density lipoprotein (lectin-like) receptor 1; *Homo sapiens*, clone IMAGE:4179671, mRNA, partial cds; protein kinase C, zeta; hypothetical protein DKFZp564F013; downregulated in ovarian cancer 1; *Homo sapiens* mRNA; cDNA DKFZp547K1113 (from clone DKFZp547K1113);

expression, which relative to a human cell that is a fibroblast, a mesenchymal stem cell, or an iliac crest bone marrow cell, is reduced for at least one of short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; dishevelled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*);

hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein I; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa;

secretion of at least one of MCP-1, IL-6, IL-8, GCP-2, HGF, KGF, FGF, HB-EGF, BDNF, TPO, MIP1a, RANTES, and TIMP1; and lack of secretion of at least one of TGF-beta2, ANG2, PDGFbb, MIP1b, 1309, MDC, and VEGF, as detected by ELISA.

In certain embodiments, the postpartum-derived cell is an umbilicus-derived cell. In other embodiments it is a placenta-derived cell. In specific embodiments, the cell has all identifying features of any one of: cell type PLA 071003 (P8) (ATCC Accession No. PTA-6074); cell type PLA 071003 (P11) (ATCC Accession No. PTA-6075); cell type PLA 071003 (P16) (ATCC Accession No. PTA-6079); cell type UMB 022803 (P7) (ATCC Accession No. PTA-6067); or cell type UMB 022803 (P17) (ATCC Accession No. PTA-6068).

The postpartum-derived cells are preferably isolated in the presence of one or more enzyme activities such as metalloprotease activity, neutral protease activity and mucolytic enzyme activity. The cells preferably comprise a normal karyotype, which is maintained as the cells are passaged.

Preferred cells produce each of CD10, CD13, CD44, CD73, CD90, PDGFr-alpha, and HLA-A,B,C, and do not produce any of CD31, CD34, CD45, CD117, CD141, or HLA-DR,DP,DQ, as detected by flow cytometry.

In another of its several aspects, the invention provides populations of cells comprising the cells described above. In certain embodiments the populations are incubated in the presence of one or more factors which stimulate stem cell differentiation along a cardiogenic pathway or lineage. In other embodiments, cells are incubated in the presence of compounds which tend to stimulate differentiation along angiogenic, hemangiogenic, and vasculogenic pathways, or towards more committed cells such as cardiomyocytes, endothelial cells, myocardial cells, epicardial cells, vascular endothelial cells, smooth muscle cells (e.g. vascular smooth muscle cells), as well as cells of the excitatory and conductive systems, and progenitors of any of the foregoing, for example, myoblasts, cardiomyoblasts, hemangioblasts, angioblasts and the like or their progenitors. The populations can be provided therapeutically to a patient, for example with heart or circulatory disease, such as a cardiomyopathy, or with a cardiac injury, such as from myocardial infarction, or with any damage or disease of the heart or circulatory system. In presently preferred embodiments, the population comprises about 50% postpartum-derived cells, while in other preferred embodiments the population is a substantially homogeneous population of postpartum-derived cells.

The invention provides in another of its aspects therapeutic cell compositions comprising a pharmaceutically-acceptable carrier and postpartum-derived cells derived from human postpartum tissue substantially free of blood. The cells are capable of self-renewal and expansion in culture and have the potential to differentiate into cells of other phenotypes; for example smooth or skeletal muscles phenotypes. In preferred embodiments, cells can differentiate along pathways leading to phenotypes of cardiomyocytes, cells of the endothelium, myocardium, epicardium, vascular endothelium, as well as smooth muscle cells (e.g. vascular smooth muscle cells), and cells of the excitatory and conductive systems (e.g. Purkinje cells), and progenitors of the foregoing. The cells are capable of growth in an atmosphere containing oxygen from about 5% to at least about 20%. The cells also require L-valine for growth; have the potential for at least about 40 doublings in culture; attach and expand on a coated or uncoated tissue culture vessel, wherein a coated tissue culture vessel is coated with gelatin, laminin, or fibronectin; produce tissue factor, vimentin, and alpha-smooth muscle actin; produce each of CD10, CD13, CD44, CD73, CD90, PDGFr-alpha, and HLA-A,B,C; and do not produce any of CD31, CD34, CD45, CD117, CD141, or HLA-DR,DP,DQ, as detected by flow cytometry.

The therapeutic cell compositions provided can be provided therapeutically in a patient with a cardiomyopathy, or other heart disease, or a cardiac injury, or any disease of the circulatory system which, for example, involves cell injury or tissue/cell necrosis. In certain embodiments, the therapeutic cell compositions comprise cells induced to differentiate along a cardiogenic, angiogenic, hemangiogenic, or vasculogenic pathway or lineage. The therapeutic cell compositions can comprise cells or cellular products that stimulate adult stem cells naturally present in the heart, blood, blood vessels or the like to divide, or differentiate, or both. Preferably the therapeutic cell compositions can at least survive, grow, stimulate in growth, stimulate angiogenesis or vasculogenesis, but in certain cases even nonviable cells such as senescent cells will be therapeutic, and in some embodiments, even dead cells, or fractions thereof will provide therapeutic improvements for a patient.

The therapeutic cell compositions are provided, for example, by injection. In certain preferred embodiments, the therapeutic cell compositions are provided by intracardiac injection. In other embodiments, they are placed adjacent to an inner or outer aspect of the cardiac muscles directly, or on a matrix as a cell-matrix complex. The therapeutic cell compositions provided in the form of a matrix-cell complex comprise matrices including, for example, biocompatible scaffolds, lattices, self-assembling structures and the like, whether bioabsorbable or not, liquid or solid. Many such matrices are known to those of skill in the arts of tissue engineering, wound healing, and the like. Therapeutic compositions can also comprise additional biological compounds or pharmaceuticals that may improve the therapeutic value to the patient, and the compositions can also comprise one or more additional cells or cell types.

The therapeutic cell compositions, in certain embodiments also comprise cells that:

express at least one of interleukin 8; reticulon 1; chemokine (C-X-C motif) ligand 1 (melonoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3;

express at least one of C-type (calcium dependent, carbohydrate-recognition domain) lectin, superfamily member 2 (activation-induced); Wilms tumor 1; aldehyde dehydrogenase 1 family, member A2; and renin; oxidized low density lipoprotein (lectin-like) receptor 1; *Homo sapiens*, clone IMAGE:4179671, mRNA, partial cds; protein kinase C, zeta; hypothetical protein DKFZp564F013; downregulated in ovarian cancer 1; *Homo sapiens* mRNA; and cDNA DKFZp547K1113 (from clone DKFZp547K1113);

have reduced expression, relative to a human cell that is a fibroblast, a mesenchymal stem cell, or an iliac crest bone marrow cell, for at least one of short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; dishevelled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa;

secrete at least one of MCP-1, IL-6, IL-8, GCP-2, HGF, KGF, FGF, HB-EGF, BDNF, TPO, MIP1a, RANTES, and TIMP1; and do not secrete at least one of TGF-beta2, ANG2, PDGFbb, MIP1b, I309, MDC, and VEGF, as detected by ELISA.

In yet another of its aspects, the invention provides methods for treating a patient with a disease or injury of the heart or circulatory system comprising administering a therapeutic postpartum-derived cell composition to a patient with a disease or injury of the heart or circulatory system; and evaluating the patient for improvements, for example in cardiac function. In certain preferred embodiments the disease is a cardiomyopathy, either idiopathic or with a known cause, and either ischemic or nonischemic in nature.

Measurement of improvement include any means known in the art, but preferred improvements include improvements in hemodynamic measurements including but not limited to chest cardiac output (CO), cardiac index (CI), pulmonary artery wedge pressures (PAWP), and cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (e.g. dP/dt), pressure-volume loops, measurements of cardiac work, as well as an increase in atrial or ventricular functioning; an increase in pumping efficiency, a decrease in the rate of loss of pumping efficiency, a decrease in loss of hemodynamic functioning; and a decrease in complications associated with cardiomyopathy.

In some presently preferred embodiments, the method comprises inducing the therapeutic postpartum-derived cells to differentiate along a cardiogenic, angiogenic, hemangiogenic, or vasculogenic pathway or or a towards cells or progenitors of cells such as cardiomyocytes, endothelial cells, myocardial cells, epicardial cells, vascular endothelial cells, smooth muscle cells (e.g. vascular smooth muscle cells), as well as cells of the excitatory and conductive systems. Cells which differentiate towards myoblasts, cardiomyoblasts, angioblasts, hemangioblasts, and the like are contemplated for use herein.

The administering is preferably in vivo by transplanting, grafting, implanting, injecting, infusing, delivering via catheter, or, providing as a matrix-cell complex, or any other means known in the art for providing cell therapy. For many applications, the cells can simply be injected, for example intravenously, and the cells will locate or home in accordance with their commitment in the direction of a phenotype associated with a particular tissue. For example, cells differentiated into a cardiomyogenic lineage may home in to the cardiac muscle when injected intravenously anywhere in the body.

The invention also provides in another aspect, methods for treating a patient with a disease or injury of the heart or circulatory system comprising administering a therapeutic postpartum-derived cell composition to a patient with a disease or injury of the heart or circulatory system; and evaluating the patient for improvements in cardiac function, wherein the administering is with a population of another cell type. Administration of cocultures, mixed populations or other nonclonal populations are sometimes preferred. Other cell types which can be coadministered are stem cells in certain embodiments, while in others myoblasts, myocytes, cardiomyoblasts, cardiomyocytes, angioblasts, hemangioblasts or a progenitors of myoblasts, myocytes, cardiomyoblasts, angioblasts, hemangioblasts, or cardiomyocytes are used. Other angiogenic, hemangiogenic, and vasculogenic cells, or more committed cells from such lineages are also suitable for coadministration.

Also provided herein are methods for treating a patient with a disease or injury of the heart or circulatory system comprising administering a therapeutic postpartum-derived cell composition to a patient with a disease or injury of the heart or circulatory system; and evaluating the patient for improvements in the diseased or injured state, wherein the therapeutic cell composition is administered as a matrix-cell complex. In certain embodiments, the matrix is a scaffold, preferably bioabsorbable, comprising in addition to the matrix proper, at least the postpartum-derived cells.

Co-cultures comprising the cells or cultures of the invention with other mammalian cells are also provided herein.

Preferably these co-cultures comprise another mammalian cell line whose growth or therapeutic potential, for example, is improved by the presence of the umbilicus-derived cells. Human cell lines are particular preferred. Such co-cultures are useful for therapeutic application in vitro or in vivo.

Also provided herein are therapeutic compositions comprising a postpartum-derived cell and another therapeutic agent, factor, or bioactive agent, such as a pharmaceutical compound. Such bioactive agents include, but are not limited to, IGF, LIF, PDGF, EGF, FGF, as well as antithrombogenic, antiapoptotic agents, anti-inflammatory agents, immunosuppressive or immunomodulatory agents, and antioxidants. Such therapeutic compositions can further comprise one or more additional cell types in addition to the PPDCs and the bioactive component.

In addition to the above, compositions derived from the cells are provided herein. Cell lysates, soluble cell fractions and membrane-enriched cell fractions are provided herein. Extracellular matrices derived from the cells, for example, fractions comprising basement membranes are also useful and are provided herein.

Compositions of the invention also include conditioned culture media as provided herein. Such media have first been used to grow the cells or cultures of the invention, which during growth secrete one or more useful products into the medium. Conditioned medium from these novel cells are useful for many purposes, including for example, supporting the growth of other mammalian cells in need of growth factors or trophic factors secreted into the media by the cells and cultures of the invention, and promoting, for example, angiogenesis.

Kits are also provided herein. Various preferred kits are those providing the required components for practicing the several aspects of the inventions, for example kits for growth and maintenance of the cells, kits for isolation of the cells, kits for coculturing the cells, kits for utilizing the cells and culture in vitro and kits for utilizing the cells and cultures in vivo are all provided herein. Kits are also provided for the preparation of cell fractions derived from the cells including for example, cell lysates, soluble and membrane-enriched fractions, and extracellular fractions.

These and other aspects of the invention are described in more detail below.

DETAILED DESCRIPTION

Definitions

Various terms used throughout the specification and claims are defined as set forth below.

Stem cells are undifferentiated cells defined by the ability of a single cell both to self-renew, and to differentiate to produce progeny cells, including self-renewing progenitors, non-renewing progenitors, and terminally differentiated cells. Stem cells are also characterized by their ability to differentiate in vitro into functional cells of various cell lineages from multiple germ layers (endoderm, mesoderm and ectoderm), as well as to give rise to tissues of multiple germ layers following transplantation, and to contribute substantially to most, if not all, tissues following injection into blastocysts.

Stem cells are classified according to their developmental potential as: (1) totipotent; (2) pluripotent; (3) multipotent; (4) oligopotent; and (5) unipotent. Totipotent cells are able to give rise to all embryonic and extraembryonic cell types. Pluripotent cells are able to give rise to all embryonic cell types. Multipotent cells include those able to give rise to a subset of cell lineages, but all within a particular tissue, organ, or physiological system (for example, hematopoietic stem cells (HSC) can produce progeny that include HSC (self-renewal), blood cell-restricted oligopotent progenitors, and all cell types and elements (e.g., platelets) that are normal components of the blood). Cells that are oligopotent can give rise to a more restricted subset of cell lineages than multipotent stem cells; and cells that are unipotent are able to give rise to a single cell lineage (e.g., spermatogenic stem cells).

Stem cells are also categorized on the basis of the source from which they may be obtained. An adult stem cell is generally a multipotent undifferentiated cell found in tissue comprising multiple differentiated cell types. The adult stem cell can renew itself. Under normal circumstances, it can also differentiate to yield the specialized cell types of the tissue from which it originated, and possibly other tissue types. An embryonic stem cell is a pluripotent cell from the inner cell mass of a blastocyst-stage embryo. A fetal stem cell is one that originates from fetal tissues or membranes. A postpartum stem cell is a multipotent or pluripotent cell that originates substantially from extraembryonic tissue available after birth, namely, the placenta and the umbilical cord. These cells have been found to possess features characteristic of pluripotent stem cells, including rapid proliferation and the potential for differentiation into many cell lineages. Postpartum stem cells may be blood-derived (e.g., as are those obtained from umbilical cord blood) or non-blood-derived (e.g., as obtained from the non-blood tissues of the umbilical cord and placenta).

Embryonic tissue is typically defined as tissue originating from the embryo (which in humans refers to the period from fertilization to about six weeks of development. Fetal tissue refers to tissue originating from the fetus, which in humans refers to the period from about six weeks of development to parturition. Extraembryonic tissue is tissue associated with, but not originating from, the embryo or fetus. Extraembryonic tissues include extraembryonic membranes (chorion, amnion, yolk sac and allantois), umbilical cord and placenta (which itself forms from the chorion and the maternal decidua basalis).

Differentiation is the process by which an unspecialized ("uncommitted") or less specialized cell acquires the features of a specialized cell, such as a nerve cell or a muscle cell, for example. A differentiated cell is one that has taken on a more specialized ("committed") position within the lineage of a cell. The term committed, when applied to the process of differentiation, refers to a cell that has proceeded in the differentiation pathway to a point where, under normal circumstances, it will continue to differentiate into a specific cell type or subset of cell types, and cannot, under normal circumstances, differentiate into a different cell type or revert to a less differentiated cell type. De-differentiation refers to the process by which a cell reverts to a less specialized (or committed) position within the lineage of a cell. As used herein, the lineage of a cell defines the heredity of the cell, i.e. which cells it came from and what cells it can give rise to. The lineage of a cell places the cell within a hereditary scheme of development and differentiation.

In a broad sense, a progenitor cell is a cell that has the capacity to create progeny that are more differentiated than itself, and yet retains the capacity to replenish the pool of progenitors. By that definition, stem cells themselves are also progenitor cells, as are the more immediate precursors to terminally differentiated cells. When referring to the cells of the present invention, as described in greater detail below, this broad definition of progenitor cell may be used. In a narrower sense, a progenitor cell is often defined as a cell that is intermediate in the differentiation pathway, i.e., it arises from a stem cell and is intermediate in the production of a mature cell type or subset of cell types. This type of progenitor cell is generally not able to self-renew. Accordingly, if this type of cell is referred to herein, it will be referred to as a non-renewing progenitor cell or as an intermediate progenitor or precursor cell.

As used herein, the phrase differentiates into a mesodermal, ectodermal or endodermal lineage refers to a cell that becomes committed to a specific mesodermal, ectodermal or endodermal lineage, respectively. Examples of cells that differentiate into a mesodermal lineage or give rise to specific mesodermal cells include, but are not limited to, cells that are adipogenic, chondrogenic, cardiogenic, dermatogenic, hematopoietic, hemangiogenic, myogenic, nephrogenic, urogenitogenic, osteogenic, pericardiogenic, or stromal. Examples of cells that differentiate into ectodermal lineage include, but are not limited to epidermal cells, neurogenic cells, and neurogliagenic cells. Examples of cells that differentiate into endodermal lineage include, but are not limited to, pleurigenic cells, hepatogenic cells, cells that give rise to the lining of the intestine, and cells that give rise to pancreogenic and splanchogenic cells.

The cells of the present invention are generally referred to as umbilicus-derived cells (or UDCs). They also may sometimes be referred to more generally herein as postpartum-derived cells or postpartum cells (PPDCs). In addition, the cells may be described as being stem or progenitor cells, the latter term being used in the broad sense. The term derived is used to indicate that the cells have been obtained from their biological source and grown or otherwise manipulated in vitro (e.g., cultured in a Growth Medium to expand the population and/or to produce a cell line). The in vitro manipulations of umbilical stem cells and the unique features of the umbilicus-derived cells of the present invention are described in detail below.

Various terms are used to describe cells in culture. Cell culture refers generally to cells taken from a living organism and grown under controlled condition ("in culture" or "cultured"). A primary cell culture is a culture of cells, tissues, or organs taken directly from an organism(s) before the first subculture. Cells are expanded in culture when they are placed in a Growth Medium under conditions that facilitate cell growth and/or division, resulting in a larger population of the cells. When cells are expanded in culture, the rate of cell proliferation is sometimes measured by the amount of time needed for the cells to double in number. This is referred to as doubling time.

A cell line is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A conditioned medium is a medium in which a specific cell or population of cells has been cultured, and then removed. When cells are cultured in a medium, they may secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a trophic factor is defined as a substance that promotes survival, growth, proliferation and/or maturation of a cell, or stimulates increased activity of a cell.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term Growth Medium generally refers to a medium sufficient for the culturing of umbilicus-derived cells. In particular, one presently preferred medium for the culturing of the cells of the invention in comprises Dulbecco's Modified Essential Media (also abbreviated DMEM herein). Particularly preferred is DMEM-low glucose (also DMEM-LG herein) (Invitrogen, Carlsbad, Calif.). The DMEM-low glucose is preferably supplemented with serum, most preferably fetal bovine serum or human serum. Typically, 15% (v/v) fetal bovine serum (e.g. defined fetal bovine serum, Hyclone, Logan Utah) is added, along with antibiotics/antimycotics ((preferably 100 Unit/milliliter penicillin, 100 milligrams/milliliter streptomycin, and 0.25 microgram/milliliter amphotericin B; Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to Growth Medium. In certain chemically-defined media the cells may be grown without serum present at all. In such cases, the cells may require certain growth factors, which can be added to the medium to support and sustain the cells. Presently preferred factors to be added for growth on serum-free media include one or more of bFGF, EGF, IGF-I, and PDGF. In more preferred embodiments, two, three or all four of the factors are add to serum free or chemically defined media. In other embodiments, LIF is added to serum-free medium to support or improve growth of the cells.

Also relating to the present invention, the term standard growth conditions, as used herein refers to culturing of cells at 37° C., in a standard atmosphere comprising 5% $CO_2$. Relative humidity is maintained at about 100%. While the foregoing conditions are useful for culturing, it is to be understood that such conditions are capable of being varied by the skilled artisan who will appreciate the options available in the art for culturing cells.

The following abbreviations are used herein:
ANG2 (or Ang2) for angiopoietin 2;
APC for antigen-presenting cells;
BDNF for brain-derived neurotrophic factor;
bFGF for basic fibroblast growth factor;
bid (BID) for "bis in die" (twice per day);
BSP for bone sialoprotein;
C:D for collagenase and dispase treatment
C:D:H for collagenase, dispase, and hyaluronidase treatment
CK18 for cytokeratin 18;
CXC ligand 3 for chemokine receptor ligand 3;
DAPI for 4'-6-Diamidino-2-phenylindole-2HCl
DMEM for Dulbecco's Minimal Essential Medium;
DMEM:lg (or DMEM:Lg, DMEM:LG) for DMEM with low glucose;
EDTA for ethylene diamine tetraacetic acid;
EGF for epidermal growth factor;
FACS for fluorescent activated cell sorting;
FBS for fetal bovine serum;
GCP-2 for granulocyte chemotactic protein 2;
GCP-2 for granulocyte chemotactic protein-2;
GFAP for glial fibrillary acidic protein;
HB-EGF for heparin-binding epidermal growth factor;
HCAEC for Human coronary artery endothelial cells;
HGF for hepatocyte growth factor;
hMSC for Human mesenchymal stem cells;
HNF-1 alpha for hepatocyte-specific transcription factor;
HUVEC for Human umbilical vein endothelial cells;
I309 for a chemokine and the ligand for the CCR8 receptor, responsible for chemoattraction of TH2 type T-cells. I309 binds to endothelial cells, stimulates chemotaxis and invasion of these cells, and enhances HUVEC differentiation into capillary-like structures in an in vitro Matrigel assay. Furthermore, I309 is an inducer of angiogenesis in vivo in both the rabbit cornea and the chick chorioallantoic membrane assay (CAM).
IL-6 for interleukin-6;
IL-8 for interleukin-8;
K19 for keratin 19;
K8 for keratin 8;
KGF for keratinocyte growth factor;
MCP-1 for monocyte chemotactic protein 1;
MDC for macrophage-derived chemokine;
MIP1alpha for macrophage inflammatory protein 1alpha;
MIP1 beta for macrophage inflammatory protein 1beta;
MSC for mesenchymal stem cells;
NDRI for National Disease Research Interchange in Philadelphia, Pa.
NHDF for Normal Human Dermal Fibroblasts;
NPE for Neural Progenitor Expansion media;
PBMC for Peripheral blood mononuclear cell;
PBS for phosphate buffered saline;
PDGFbb for platelet derived growth factor;
PDGFr/alpha for platelet derived growth factor receptor alpha;
PD-L2 for programmed—death ligand 2;
PO (or po) for "per os" (by mouth);
PPDC for postpartum-derived cell;
Rantes (or RANTES) for regulated on activation, normal T cell expressed and secreted;
rhGDF-5 for recombinant human growth and differentiation factor 5;
SC for subcutaneously;
SDF-1 alpha for stromal-derived factor 1 alpha;
SHH for sonic hedgehog;
SOP for standard operating procedure;
TARC for thymus and activation-regulated chemokine;
TCP for Tissue culture plastic;
TGFbeta2 for transforming growth factor beta2;
TGFbeta-3 for transforming growth factor beta-3;
TIMP1 for tissue inhibitor of matrix metalloproteinase 1;
TPO for thrombopoietin;
TuJ1 for BIII Tubulin;
UDC for umbilicus-derived cell;
VEGF for vascular endothelial growth factor;
vWF for von Willebrand factor;
alphaFP for alpha-fetoprotein;

DESCRIPTION

Various articles and references are cited herein and throughout, each of which is hereby incorporated in its entirety by such reference.

As summarized above, the invention, in one of its aspects is generally directed to isolated postpartum-derived cells which are derived from postpartum tissue which is substantially free of blood and which are capable of self-renewal and expansion in culture and having the potential to differentiate along mesenchymal lineage, towards cardiomyogenic, angiogenic and vasculogenic phenotypes, and further towards cells such as cardiomyocytes, endothelial cells, myocardial cells, epicardial cells, vascular endothelial cells, smooth muscle cells (e.g. vascular smooth muscle cells), as well as cells of the excitatory and conductive systems, and progenitors of the foregoing. Other aspects provide populations comprising such cells, therapeutic cell compositions, and methods of using the therapeutic cell compositions for treatment of patients with injury or disease of the heart or circulatory system. The postpartum-derived cells have been characterized by their growth properties in culture, by their cell surface markers, by their gene expression, by their ability to produce certain biochemical trophic factors, and by their immunological properties.

In a first aspect, the invention provides isolated postpartum-derived cells comprising L-valine-requiring cells derived from mammalian postpartum tissue substantially free of blood. The cells are capable of self-renewal and expansion in culture and have the potential to differentiate into cells of other phenotypes; for example cardiomyocytes, or their progenitors. Cells may be isolated from postpartum tissue, for example umbilicus or placenta, of any mammal of interest by the techniques provided herein. Human cells are presently preferred. The cells can be grown under a wide range of conditions, including a wide variety of culture media, and environmental conditions. The cells can be grown at least from about 35° C. to about 39° C., and possibly a wider range depending on other conditions. The cells can be grown in chemically-defined media, or in medium with added mammalian serum, for example fetal bovine serum. The cells also tolerate cryopreservation at various stages. Cells can maintained frozen, or banked at temperatures preferably below −80° C. for long periods. Temperature below −90° C. are also preferred and can be attained by specialized electric freezers. Temperature of −180° C. and below are also preferred and can be attained in liquid- or vapor-phase nitrogen. Tissues can also be banked prior to the isolation of the cells. Preferably such tissues are banked within a few hours or less after the completion of the pregnancy.

The cells are capable of growth in atmospheres containing oxygen from about 5% to at least about 20% and comprise at least one of the following characteristics: the cells have the potential for at least about 40 doublings in culture; the cells preferably are adherent, thus attachment and expansion on a coated or uncoated tissue culture vessel is preferred, wherein a coated tissue culture vessel comprises a coating of gelatin, laminin, collagen, polyornithine, polylysine, vitronectin, or fibronectin. While the cells are preferably adherent and isolated as such, the cells have been grown in a spherical form in some embodiments.

Many populations of cells are present in postpartum tissue, but the cells of the invention preferably produce of at least one of tissue factor, vimentin, and alpha-smooth muscle actin; more preferred are cells which produce each of tissue factor, vimentin, and alpha-smooth muscle actin; production of at least one of CD10, CD13, CD44, CD73, CD90, PDGFr-alpha, PD-L2 and HLA-A,B,C is also preferred. The cells are also characterized in their lack of production of at least one of CD31, CD34, CD45, CD80, CD86, CD117, CD141, CD178, B7-H2, HLA-G, and HLA-DR,DP,DQ, as detected by flow cytometry; more preferable cells lack production of all of these surface markers. Also preferred are cells which express at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3. The cells, in other embodiments, preferably also express one or more of C-type (calcium dependent, carbohydrate-recognition domain) lectin, superfamily member 2 (activation-induced); Wilms tumor 1; aldehyde dehydrogenase 1 family, member A2; and renin; oxidized low density lipoprotein (lectin-like) receptor 1; *Homo sapiens*, clone IMAGE:4179671, mRNA, partial cds; protein kinase C, zeta; hypothetical protein DKFZp564F013; downregulated in ovarian cancer 1; *Homo sapiens* mRNA; and cDNA DKFZp547K1113 (from clone DKFZp547K1113). Preferred cells also have expression, which relative to a human cell that is a fibroblast, a mesenchymal stem cell, or an iliac crest bone marrow cell, is reduced for at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; dishevelled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FlJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FlJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FlJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ 14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; and insulin-like growth factor binding protein 2, 36 kDa. The skilled artisan will appreciate that the expression of a wide variety of genes is conveniently characterized on oligonucleotide arrays, for example on a Affymetrix GENECHIP.

The cells secrete a variety of biochemically active factors, such as growth factors, chemokines, cytokines and the like. Preferred cells secrete at least one of MCP-1, IL-6, IL-8, GCP-2, HGF, KGF, FGF, HB-EGF, BDNF, TPO, MIP1a, RANTES, and TIMP1; preferred cells may alternatively be characterized in their lack of secretion of at least one of TGF-beta2, ANG2, PDGFbb, MIP1b, I309, MDC, and VEGF, as detected by ELISA. These and other characteristics are available to identify and characterize the cells, and distinguish the cells of the invention from others known in the art.

In preferred embodiments, the cell comprises two or more of the foregoing characteristics. More preferred are those cells comprising, three, four, or five or more of the characteristics. Still more preferred are those isolated postpartum cells comprising six, seven, or eight or more of the characteristics. Still more preferred presently are those cells comprising all nine of the claimed characteristics.

Also presently preferred are cells that produce at least two of tissue factor, vimentin, and alpha-smooth muscle actin. More preferred are those cells producing all three of the proteins tissue factor, vimentin, and alpha-smooth muscle actin.

The skilled artisan will appreciate that cell markers are subject to vary somewhat under vastly different growth conditions, and that generally herein described are characterizations in Growth Medium, or variations thereof. Postpartum-derived cells that produce of at least one, two, three, or four of CD10, CD13, CD44, CD73, CD90, PDGFr-alpha, PD-L2 and HLA-A,B,C are preferred. More preferred are those cells producing five, six, or seven of these cell surface markers. Still more preferred are postpartum cells that can produce all eight of the foregoing cell surface marker proteins.

Similarly, postpartum cells that lack production of at least one, two, three, four of the proteins CD31, CD34, CD45, CD80, CD86, CD117, CD141, CD178, B7-H2, HLA-G, and HLA-DR,DP,DQ, as detected by flow cytometry are presently preferred. Cells lacking production of at least five, six, seven or eight or more of these markers are also preferred. More preferred are cells which lack production of at least nine or ten of the cell surface markers. Most highly preferred are those cells lacking production of all eleven of the foregoing identifying proteins.

Presently preferred cells produce each of CD10, CD13, CD44, CD73, CD90, PDGFr-alpha, and HLA-A,B,C, and do not produce any of CD31, CD34, CD45, CD117, CD141, or HLA-DR,DP,DQ, as detected by flow cytometry.

Presently, it is preferred that postpartum-derived cells express at least one, two or three of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3. More preferred are those cells which express four or five, and still more preferred are cell capable of expressing all six of the foregoing genes.

In some embodiments, the cells preferably also express two, three, four or more of C-type (calcium dependent, carbohydrate-recognition domain) lectin, superfamily member 2 (activation-induced); Wilms tumor 1; aldehyde dehydrogenase 1 family, member A2; renin; oxidized low density lipoprotein (lectin-like) receptor 1; *Homo sapiens*, clone IMAGE:4179671, mRNA, partial cds; protein kinase C, zeta; hypothetical protein DKFZp564F013; down-regulated in ovarian cancer 1; *Homo sapiens* mRNA; and cDNA DKFZp547K1113 (from clone DKFZp547K1113). In other embodiments, it is preferred that the cells express five, six, seven or eight of the foregoing. Also preferred are those cells expressing genes corresponding to nine, ten or even all of the foregoing sequences.

For some embodiments, preferred are cells, which relative to a human cell that is a fibroblast, a mesenchymal stem cell, or an iliac crest bone marrow cell, have reduced expression for at least one of the genes corresponding to: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; dishevelled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein FLJ20373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus E1B 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa. More preferred are cells that have, relative to human fibroblasts, mesenchymal stem cells, or iliac crest bone marrow cells, reduced expression of at least 5, 10, 15 or 20 genes corresponding to those listed above. Presently more preferred are cell with reduced expression of at least 25, 30, or 35 of the genes corresponding to the listed sequences. Also more preferred are those postpartum-derived cells having expression that is reduced, relative to that of a human fibroblast, a mesenchymal stem cell, or an ilea iliac crest bone marrow cell, of genes corresponding to 35 or more, 40 or more, or even all of the sequences listed.

Secretion of certain growth factors and other cellular proteins can make cells of the invention particularly useful. Preferred postpartum-derived cells secrete at least one, two, three or four of MCP-1, IL-6, IL-8, GCP-2, HGF, KGF, FGF, HB-EGF, BDNF, TPO, MIP1a, RANTES, and TIMP1. Cells which secrete more than five, six, seven or eight of the listed proteins are also useful and preferred. Cells which can secrete at least nine, ten, eleven or more of the factors are more preferred, as are cells which can secrete twelve or more, or even all thirteen of the proteins in the foregoing list.

While secretion of such factors is useful, cells can also be characterized by their lack of secretion of factors into the medium. Postpartum-derived cells that lack secretion of at least one, two, three or four of TGF-beta2, ANG2, PDGFbb, MIP1b, I309, MDC, and VEGF, as detected by ELISA, are presently preferred for use. Cells that are characterized in their lack secretion of five or six of the foregoing proteins are more preferred. Cells which lack secretion of all seven of the factors listed above are also preferred.

The postpartum-derived cells are preferably isolated in the presence of one or more enzyme activities. A broad range of digestive enzymes for use in cell isolation from tissue are known in the art, including enzymes ranging from those considered weakly digestive (e.g. deoxyribonucleases and the neutral protease, dispase) to strongly digestive (e.g. papain and trypsin). For example, collagenases are known to be useful for isolating various cells from (tissues. Deoxyribonucleases can digest single-stranded DNA and can minimize cell-clumping during isolation. Enzymes can be used alone or in combination. Serine protease are preferably used in a sequence following the use of other enzymes as they may degrade the other enzymes being used. The temperature and time of contact with serine proteases must be monitored. Serine proteases may be inhibited with alpha 2 microglobulin in serum and therefore the medium used for digestion is preferably serum-free. EDTA and DNase are commonly used and may improve yields or efficiencies. Preferred methods involve enzymatic treatment with for example collagenase and dispase, or collagenase, dispase, and hyaluronidase, and such methods are provided wherein in certain preferred embodiments, a mixture of collagenase and the neutral protease dispase are used in the dissociating step. Presently preferred are mucolytic enzyme activities, metalloproteases, neutral proteases, serine proteases (such as trypsin, chymotrypsin, or elastase), and deoxyribonucleases. More preferred are enzyme activites selected from metalloproteases, neutral proteases and mucolytic activities. Presently preferred are cells that are isolated in the presence of one or more activities of collagenase, hyaluronidase and dispase. More preferred are those cells isolated in the presence of a collagenase from *Clostridium histolyticum*, and either of the protease activities, dispase and thermolysin. Still more preferred are cells isolated with collagenase and dispase enzyme activities. Also preferred are such cells isolated in the presence of a hyaluronidase activity, in addition to collagenase and dispase activity. The skilled artisan will appreciate that many such enzyme treatments are known in the art for isolating cells from various tissue sources. Also useful for isolation of certain cells of the invention are commercial enzyme preparations such as blends of enzymes, for example, LIBERASE Blendzymes available from Roche Diagnostics. The skilled artisan will appreciate the methods for optimizing enzyme use during isolation, and information on such optimization procedures is available from the manufacturers of commercial enzymes. Preferred are those methods which can result in homogenous populations or nearly homogeneous populations of cells.

The cells also preferably comprise a normal karyotype, which is maintained as the cells are passaged. Karyotyping is particularly useful for identifying and distinguishing neonatal from maternal cells derived from placenta. Methods for karyotyping are available and known to those of skill in the art.

Among cells that are presently preferred for use with the invention in several of its aspects are postpartum cells having the characteristics described above and more particularly those wherein the cells have normal karyotypes and maintain normal karyotypes with passaging, and during cryopreservation and subsequent thawing and use, and further wherein the cells express each of the markers CD10, CD13, CD44, CD73, CD90, PDGFr-alpha, and HLA-A,B,C, wherein the cells produce the immunologically-detectable proteins which correspond to the listed markers. Still more preferred are those cells which in addition to the foregoing do not produce proteins corresponding to any of the markers CD31, CD34, CD45, CD 117, CD141, or HLA-DR,DP,DQ, as detected by flow cytometry.

Certain prior art cells having the potential to differentiate along lines leading to various phenotypes are unstable and thus can spontaneously differentiate. Presently preferred for use with the invention are cells which do not spontaneously differentiate, for example along cardiomyogenic, angiogenic, hemangiogenic, or vasculagenic lines. Preferred cells when grown in Growth Medium are substantially stable with respect to the cell markers produced on their surface, and with respect to the expression pattern of various genes, for example as determined using oligonucleotide arrays, such as an Affymetrix GENECHIP. The cells remain substantially constant in their biochemical, genetic, and immunological characteristics, for example, their cell surface markers, over passaging, and through multiple population doublings.

In another of its several aspects, the invention provides populations of cells comprising the cells described above. Cell populations are useful in connection with the methods of the invention, as well as in connection with making the therapeutic cell compositions and cell lysates in larger amounts than isolated cells can provide.

Preferred populations comprise from about 1% postpartum-derived cells to about 10% postpartum cells. More preferred populations comprise at least about 10% postpartum-derived cells. More preferred populations comprise at least about 25% postpartum-derived cells. Also, some preferred populations comprise about 50% postpartum-derived cells. Such populations may be useful for coculture or other cultures wherein the cells are equally populous and divide at the same rate, or where the population is adjusted to about 50% of each culture after expansion of the cultures in coculture or separately. More preferred for some applications are populations comprising at least about 65% postpartum-derived cells. Populations that comprising at least 90% postpartum-derived cells are highly preferred for certain aspects of the invention. More preferred populations comprise substantially only postpartum-derived cells.

The populations may comprise a clonal cell line of postpartum-derived cells. Such populations are particularly useful wherein a cell clone with highly desirable functionality is isolated. Both neotal and maternal clones are useful and are provided herein. Methods of isolating clonal cell lines from cultured cells are known in the art.

The invention also provides cell lysates, soluble cell fractions and membrane-enriched cell fractions prepared from the populations of the postpartum cells. Such lysates and fractions have many utilities. Use of cell lysates, and more particularly soluble cell fractions, in vivo allows the beneficial intracellular milieu to be used in a patient allogeneic patient without stimulating allogeneic lymphocytes, or generating other adverse immunological responses, or triggering rejection. Methods of lysing cells are well-known in the art and include various means of mechanical disruption, enzymatic disruption, or chemical disruption, or combinations thereof. Such cell lysates may be prepared from cells directly in their Growth Medium and thus containing secreted growth factors and the like, or may be prepared from cells washed free of medium in, for example, PBS or another solution. For making lysates from cells directly in the growth medium it is preferred that cells are grown in serum from the species in which the lysates are to be used, in some embodiments, washed cells may be preferred. Washed cells may be resuspended at concentrations greater than the original population density if preferred. Cell lysates prepared from populations of postpartum-derived cells may be used as is, further concentrated, by for example, ultrafiltration or lyophilization, or even dried, enriched, partially purified, combined with pharmaceutically-acceptable carriers or diluents as are known in the art, or combined with other compounds such as biologicals, for example pharmaceutically useful protein compositions. Cell lysates may be used in vitro or in vivo, alone or, for example, with syngeneic or autologous live cells. The lysates, if introduced in vivo, may be introduced locally at a site of treatment, or remotely to provide, for example, needed cellular growth factors to a patient. Preferably, the lysates are not immunogenic, and more preferably they are immunologically tolerated in a broad population of syngeneic and allogeneic recipients without adverse immunological consequences or reaction. Cell lysates of the invention are useful from cells at any stage or age which have been grown under conditions for growth and expansion, for example on Growth Medium. Even senescent cells are useful for the preparation of lysate and can provide certain factors which are biologically useful. Nonviable or even dead or killed cells have utility for preparing lysates, and cellular fractions. Also useful are lysates from cells which have been exposed to factors which tend to induce them along a mesenchymal pathway, particularly towards cardiomyogenic, angiogenic, hemangiogenic, and vasculogenic lines. Cell lysates from differentiated cells, or cells more committed than the PPDCs are also desirable. For example, lysates from cells with characteristics of cardiomyoblasts, cardiomyocytes, angioblasts, hemangioblasts and the like, or their progenitors are also useful and contemplated for use herewith.

Also provided herein are populations of cells incubated in the presence of one or more factors which stimulate stem cell differentiation along a cardiogenic, angiogenic, hemangiogenic, or vasculogenic pathway. Such factors are known in the art and the skilled artisan will appreciate that determination of suitable conditions for differentiation can be accomplished with routine experimentation. Optimization of such conditions can be accomplished by statistical experimental design and analysis, for example, response surface methodology allows simultaneous optimization of multiple variables, for example biological culture conditions. Presently preferred factors include, but are not limited to factors, such as growth factors, chemokines, cytokines, cellular products, demethylating agents, and other stimuli which are now known or later determined to stimulate differentiation, for example of stem cells, along cardiogenic, angiogenic, hemangiogenic, or vasculogenic pathways or lineages. Presently preferred for inducing or stimulating differentiation along a cardiogenic, angiogenic, hemangiogenic, or vasculogenic pathway are cells incubated in the presence of factors comprising at least one of a demethylation agent, a member of BMP, FGF, TAK, GATA, Csx, NK, MEF2, ET-1, and Wnt factor families, Hedgehog, Csx/Nkx-2.5, and anti-Wnt factors. DNA methylation is known to silence certain genes, preventing their expression, demethylation may allow expression of such genes, including some required for differentiation. Preferred demethylation agents include inhibitors of DNA methyltransferases or inhibitors of histone deacetylase, or inhibitors of a repressor complex.

Presently preferred demethylation agents comprise at least one of 5-azacytidine, 5-aza-2'-deoxycytidine, DMSO, chelerythrine chloride, retinoic acid or salts thereof, 2-amino-4-(ethylthio)butyric acid, procainamide, and procaine. Inclusion of such factors tend to induce the cells to differentiate along mesenchymal lines, toward a cardiomyogenic pathway, as determined, for example, by the expression of at least one of cardiomyosin, skeletal myosin, or GATA4; or by the acquisition of a beating rhythm, spontaneous or otherwise induced; or by the ability to integrate at least partially into a patient's cardiac muscle without inducing arrhythmias.

In preferred embodiments herein, cells induced with one or more factors as identified above may become cardiomyogenic, angiogenic, hemangiogenic, or vasculogenic cells, or progenitors or primitive relatives thereof. Preferably at least some of the cells can integrate at least partially into the patient's heart or vasculature tree, including but not limited to heart muscle, vascular and other structures of the heart, blood vessels, and the like. More preferred are differentiated cells acquiring two or more of the indicia of cardiomyogenic, cells or their progenitors, and able to fully integrate into a patient's heart or vasculature. Still more preferred are those cells which when placed into a patient, result in no increase in arrhythmias, heart defects, blood vessel defects or other anomalies related to the patient's circulatory system or health. Also preferred are those cells which can stimulate stem cells naturally present in the patient's cardiac muscle, blood vessels, blood and the like to themselves differentiate into for example, cardiomyocytes, or at least along cardiomyogenic, angiogenic, hemangiogenic, or vasculogenic lines. Equally preferred are PPDCs which can support the stem cells naturally present in the patient's cardiac muscle, blood, blood stream and the like to grow and expand and be available for later differentiation.

The populations can be provided therapeutically to a patient, for example with a disease of the heart or circulatory system. Common examples, not intended to limit the invention, include congestive heart failure due to atherosclerosis, cardiomyopathy, or cardiac injury, such as from myocardial infarction or wound (acute or chronic). In presently preferred embodiments, the population comprises about 50% postpartum-derived cells, while in other preferred embodiments the population is a substantially homogeneous population of postpartum-derived cells. In other embodiments the population comprises at least about 1, 10, 20, 25, 30, 33, 40, 60, 66, 70, 75, 80, or 90% postpartum-derived cells.

Co-cultures comprising the cells or cultures of the invention with other mammalian cells are also provided herein. Preferably these co-cultures comprise another mammalian cell line whose growth or therapeutic potential, for example, is improved by the presence of the umbilicus-derived cells. Human cell lines are particular preferred. Such co-cultures are useful for therapeutic application in vitro or in vivo.

Also provided herein are therapeutic compositions comprising a postpartum-derived cell and another therapeutic agent, factor, or bioactive agent, such as a pharmaceutical compound. Such bioactive agents include, but are not limited to, IGF, LIF, PDGF, EGF, FGF, as well as antithrombogenic, antiapoptotic agents, anti-inflammatory agents, immunosuppressive or immunomodulatory agents, and antioxidants. Such therapeutic compositions can further comprise one or more additional cell types in addition to the PPDCs and the bioactive component.

Thus, in conjunction with therapeutic cells, other biologically active molecules, such as antithrombogenic agents, antiapoptotic agents, and anti-inflammatory agents may be useful and may be administered in sequence with, or coadministered with the the cells, individually or in combinations or two or more such compounds or agents. For example, anti-apoptotic agents may be useful to minimize programmed cell death. Such agents include but are not limited to EPO, EPO derivatives and analogs, and their salts, TPO, IGF-I, IGF-II, hepatocyte growth factor (HGF), and caspase inhibitors. Anti-inflammatory agents include but are not limited to P38 MAP kinase inhibitors, statins, IL-6 and IL-1 inhibitors, Pemirolast, Tranilast, Remicade, Sirolimus, nonsteroidal anti-inflammatory compounds, for example, Tepoxalin, Tolmetin, and Suprofen.

Other bioactive factors or therapeutic agents which can be coadministered with the therapeutic cells of the invention include, for example, antithrombogenic factors, immunosuppressive or immunomodulatory agents, and antioxidants. Examples of immunosuppressive and immudulatory agents include calcineurin inhibitors, for example cyclosporine, Tacrolimus, mTOR inhibitors such as Sirolimus or Everolimus; anti-proliferatives such as azathioprine and mycophenolate mofetil; corticosteroids for example prednisolone or hydrocortisone; antibodies such as monoclonal anti-IL-2Rα receptor antibodies, Basiliximab, Daclizumab; polyclonal anti-T-cell antibodies such as anti-thymocyte globulin (ATG), anti-lymphocyte globulin (ALG), and the monoclonal anti-T cell antibody OKT3. Antithrombogenic compounds which can be therapeutically provided in conjunction with the cells of the invention include, for example, heparin, heparin derivatives, urokinase, and PPack (dextrophenylalanine proline arginine chloromethylketone); antithrombin compounds, platelet receptor antagonists, anti-thrombin antibodies, anti-platelet receptor antibodies, aspirin, dipyridamole, protamine, hirudin, prostaglandin inhibitors, and platelet inhibitors. Antioxidants are well known in the art of course and any pharmaceutically acceptable antioxidant may be administered in conjunction with the cells of the invention including probucol; vitamins A, C, and E, coenzyme Q-10, glutathione, L cysteine, N-acetylcysteine, or antioxidant derivative, analogs or salts of the foregoing.

In addition to the above, compositions derived from the cells are provided herein. Cell lysates, soluble cell fractions and membrane-enriched cell fractions are provided herein, as described above in detail. Extracellular matrices derived from the cells, for example, comprising basement membranes are also useful and are provided herein. Cell lysates, soluble cell fractions, membrane-enriched cell fractions and extracellular matrix derived from the cells can all be administered to patients as appropriate, or coadministered with the cells of the invention, with or without additional cells or cell types.

Compositions of the invention also include conditioned culture media as provided herein. Such media have first been used to grow the cells or cultures of the invention, which during growth secrete one or more useful products into the medium. Conditioned medium from these novel cells are useful for many purposes, including for example, supporting the growth of other mammalian cells in need of growth factors or trophic factors secreted into the media by the cells and cultures of the invention, and promoting, for example, angiogenesis. Methods of preparing and storing conditioned media are known in the art and primarily involve removal of the cells, for example by centrifugation.

The invention provides in another of its aspects therapeutic cell compositions comprising a pharmaceutically-acceptable carrier and postpartum-derived cells derived from mammalian postpartum tissue substantially free of blood. The cells are capable of self-renewal and expansion in culture and have the potential to differentiate along mesenchymal lineage, towards cardiomyogenic, angiogenic and vasculogenic phenotypes, and further towards cells such as cardiomyocytes, endothelial cells, myocardial cells, epicardial cells, vascular endothelial cells, smooth muscle cells (e.g. vascular smooth muscle cells), as well as cells of the excitatory and conductive systems, and progenitors of the foregoing. The cells are capable of growth in an atmosphere containing oxygen from about 5% to at least about 20%. The cells also require L-valine for growth; have the potential for at least about 40 doublings in culture; attach and expand on a coated or uncoated tissue culture vessel, wherein a coated tissue culture vessel is coated with gelatin, laminin, or fibronectin; produce tissue factor, vimentin, and alpha-smooth muscle actin; produce each of CD10, CD13, CD44, CD73, CD90, PDGFr-alpha, and HLA-A,B,C; and do not produce any of CD31, CD34, CD45, CD117, CD141, or HLA-DR,DP,DQ, as detected by flow cytometry. In preferred embodiments the cells are derived from human tissue.

The therapeutic cell compositions provided can be provided therapeutically in a patient with a disease of the heart or circulatory system, such as a cardiomyopathy, or other heart disease, or a cardiac injury. In certain embodiments, the therapeutic cell compositions comprise cells induced to differentiate along a cardiogenic, angiogenic, hemangiogenic, or vasculogenic pathway or lineage. The therapeutic cell compositions can comprise cells or cell products that stimulate adult stem cells present in the heart, blood, blood vessels and the like, to divide, or differentiate, or both.

The therapeutic cell compositions are provided, for example, by injection. In certain embodiments, the therapeutic cell compositions are provided by intracardiac injection. In other embodiments, the injection may be onto the surface of the heart, into an adjacent area, or even to a more remote area. In preferred embodiments, the cells can home to the diseased or injured area. Particularly preferred are cells that can be injected intravenously and locate appropriately to the desired site of action, for example, cardiomyocytes or their progenitors preferably have the ability to locate and home to the heart muscle or it structures.

The therapeutic cell compositions can also be provided in the form of a matrix-cell complex. Matrices include biocompatible scaffolds, lattices, self-assembling structures and the like, whether bioabsorbable or not, liquid, gel, or solid. Such matrices are known in the arts of therapeutic cell treatment, surgical repair, tissue engineering, and wound healing. Preferably the matrices are pretreated with the therapeutic cells. More preferably the matrices are populated with cells in close association to the matrix or its spaces. The cells can adhere to the matrix in some embodiments, in others the cells are entrapped or contained within the matrix spaces. Most preferred are those matrix-cell complexes were the cells are growing in close association with the matrix and when used therapeutically, in growth of the patient's cells is stimulated and supported, and proper angiogenesis is similarly stimulated or supported. The matrix-cell compositions can be introduced into a patients body in any way known in the art, including but not limited to implantation, injection, surgical attachment, transplantation with other tissue, injection, and the like. In some embodiments, the matrices form in vivo, or even more preferably in situ, for example in situ polymerizable gels can be used in accordance with the invention. Examples of such gels are known in the art.

In some embodiments, the cells of the invention, or co-cultures thereof, may be seeded onto such three-dimensional matrices, such as scaffolds and implanted in vivo, where the seeded cells may proliferate on or in the framework or help establish replacement tissue in vivo with or without cooperation of other cells.

Growth of PPDCs or co-cultures thereof on the three-dimensional framework preferably results in the formation of a three-dimensional tissue, or foundation therefor, which can be utilized in vivo, for example for repair of damaged or diseased tissue. For example, the three-dimensional scaffolds can be used to form tubular structures, for example for use in repair of blood vessels; or aspects of the circulatory system or coronary structures.

In accordance with one aspect of the invention, PPDCs or co-cultures thereof are inoculated, or seeded on a three-dimensional framework or matrix, such as a scaffold, a foam or hydrogel. The framework may be configured into various shapes such as generally flat, generally cylindrical or tubular, or can be completely free-form as may be required or desired for the corrective structure under consideration. In some embodiments, the PPDCs grow on the three dimensional structure, while in other embodiments, the cells only survive, or even die, however in doing so they stimulate or promote ingrowth of new tissue, for example, and preferably vascularization. PPDCs may be co-administered with myocytes, myoblasts, vascular endothelial cells, dermal fibroblasts, keratinocytes, and other soft tissue type progenitors, including stem cells. When grown in this three-dimensional system, the proliferating cells mature and segregate properly to form components of adult tissues analogous to counterparts found naturally in vivo.

For example, but not by way of limitation, the matrix may be designed such that the matrix structure: (1) supports the PPDCs or co-cultures thereof without subsequent degradation; (2) supports the PPDCs or co-cultures thereof from the time of seeding until the tissue transplant is remodeled by the host tissue; (2) allows the seeded cells to attach, proliferate, and develop into a tissue structure having sufficient mechanical integrity to support itself in vitro, at which point, the matrix is degraded. A review of matrix design is provided by Hutmacher, *J. Biomat. Sci. Polymer Edn.*, 12(1):107-124 (2001).

The matrices, scaffolds, foams and self-assembling systems contemplated for use herein can be implanted in combination with any one or more cells, growth factors, drugs, or other components, such as bioactive agents that promote healing, or in growth of tissue, or stimulate vascularization or innervation thereof or otherwise enhance or improve the therapeutic outcome or the practice of the invention, in addition to the cells of the invention.

The cells of the invention can be grown freely in culture, removed from the culture and inoculated onto a three-dimensional framework. Inoculation of the three-dimensional framework with a concentration of cells, e.g., approximately $10^6$ to $5 \times 10^7$ cells per milliliter, preferably results in the establishment of the three-dimensional support in relatively shorter periods of time. Moreover in some application it may be preferably to use a greater or lesser number of cells depending on the result desired.

In some embodiments, it is useful to re-create in culture the cellular microenvironment found in vivo, such that the extent to which the cells are grown prior to implantation in vivo or use in vitro may vary. PPDCs or co-cultures thereof may be inoculated onto the framework before or after forming the shape desired for implantation, e.g., ropes, tubes, filaments, and the like. Following inoculation of the cells onto the framework, the framework is preferably incubated in an appropriate growth medium. During the incubation period, the inoculated cells will grow and envelop the framework and may for example bridge, or partially bridge any interstitial spaces therein. It is preferable, but not required to grow the cells to an appropriate degree which reflects the in vivo cell density of the tissue being repaired or regenerated. In other embodiments, the presence of the PPDCs, even in relatively low numbers on the framework encourages ingrowth of the other healthy cells to facilitate healing for example of a wounded or necrotic tissue.

Examples of matrices, for example scaffolds which may be used for aspects of the invention include mats (woven, knitted, and more preferably nonwoven) porous or semiporous foams, self assembling peptides and the like. Nonwoven mats may, for example, be formed using fibers comprised of natural or synthetic polymers. In a preferred embodiment, absorbable copolymers of glycolic and lactic acids (PGA/PLA), sold under the tradename VICRYL (Ethicon, Inc., Somerville, N.J.) are used to form a mat. Foams, composed of, for example, poly(epsilon-caprolactone)/poly(glycolic acid) (PCL/PGA) copolymer, formed by processes such as freeze-drying, or lyophilization, as discussed in U.S. Pat. No. 6,355,699, can also serve as scaffolds. Gels also form suitable matrices, as used herein. Examples include in situ polymerizable gels, and hydrogels, for example composed of self-assembling peptides. These materials are frequently used as supports for growth of tissue. In situ-forming degradable networks are also suitable for use in the invention (see, e.g., Anseth, K. S. et al., 2002, *J. Controlled Release* 78: 199-209; Wang, D. et al., 2003, *Biomaterials* 24: 3969-3980; U.S. Patent Publication 2002/0022676 to He et al.). These materials are formulated as fluids suitable for injection, then may be induced by a variety of means (e.g., change in temperature, pH, exposure to light) to form degradable hydrogel networks in situ or in vivo.

According to a preferred embodiment, the framework is a felt, which can be composed of a multifilament yarn made from a bioabsorbable material, e.g., PGA, PLA, PCL copolymers or blends, or hyaluronic acid. The yarn is made into a felt using standard textile processing techniques consisting of crimping, cutting, carding and needling. In another preferred embodiment the cells of the invention are seeded onto foam scaffolds that may be composite structures. In addition, the three-dimensional framework may be molded into a useful shape, such as a specific structure in the body to be repaired, replaced, or augmented.

The framework may be treated prior to inoculation of the cells of the invention in order to enhance cell attachment. For example, prior to inoculation with the cells of the invention, nylon matrices could be treated with 0.1 molar acetic acid and incubated in polylysine, PBS, and/or collagen to coat the nylon. Polystyrene could be similarly treated using sulfuric acid.

In addition, the external surfaces of the three-dimensional framework may be modified to improve the attachment or growth of cells and differentiation of tissue, such as by plasma coating the framework or addition of one or more proteins (e.g., collagens, elastic fibers, reticular fibers), glycoproteins, glycosaminoglycans (e.g., heparin sulfate, chondroitin-4-sulfate, chondroitin-6-sulfate, dermatan sulfate, keratin sulfate), a cellular matrix, and/or other materials such as, but not limited to, gelatin, alginates, agar, agarose, and plant gums, among others.

In some embodiments, the scaffold is comprised of or is treated with materials that render it non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the scaffold non-thrombogenic. Such treatments include anti-thrombotic agents such as heparin, and treatments which alter the surface charge of the material such as plasma coating.

Different proportions of the various types of collagen, for example, deposited on the framework can affect the growth of tissue-specific or other cells which may be later inoculated onto the framework or which may grow onto the structure in vivo. For example, for three-dimensional skin culture systems, collagen types I and III are preferably deposited in the initial matrix. Alternatively, the framework can be inoculated with a mixture of cells which synthesize the appropriate collagen types desired. Thus, depending upon the tissue to be cultured, the appropriate collagen type to be inoculated on the framework or produced by the cells seeded thereon may be selected. For example, the relative amounts of collagenic and elastic fibers present in the framework can be modulated by controlling the ratio of collagen-producing cells to elastin-producing cells in the initial inoculum. For example, since the inner walls of arteries are rich in elastin, an arterial scaffold should contain a co-culture of smooth muscle cells which secrete elastin.

The seeded or inoculated three-dimensional framework of the invention can be used in a variety of applications. These include but are not limited to transplantation or implantation of either the cultured cells obtained from the matrix or the cultured matrix itself in vivo. The three-dimensional scaffolds may, according to the invention, be used to replace or augment existing tissue, to introduce new or altered tissue, to modify artificial prostheses, or to join together biological tissues or structures. For example, and not by way of limitation, specific embodiments of the invention include but are not limited to, flat structures and tubular three-dimensional tissue implants for repair or regeneration, for example, of cardiac muscle, its structures, and those of the entire vascular tree, including for example the endovascular structures of the brain and intracranium.

PPDCs can be inoculated onto a flat scaffold. The scaffold is preferably incubated in culture medium prior to implantation. Two or more flat frameworks can be laid atop another and sutured together to generate a multilayer framework.

For example and not by way of limitation, the three-dimensional framework can also be used to construct single and multi-layer tubular tissues in vitro that can serve as a replacement for damaged or diseased tubular tissue in vivo.

A scaffold can be cut into a strip (e.g., rectangular in shape) of which the width is approximately equal to the inner circumference of the tubular organ into which it will ultimately be inserted. The cells can be inoculated onto the scaffold and incubated by floating or suspending in liquid media. At the appropriate stage of confluence, the scaffold can be rolled up into a tube by joining the long edges together. The seam can be closed by suturing the two edges together using fibers of a suitable material of an appropriate diameter.

According to the invention, a scaffold can be formed as a tube, inoculated with PPDCs, and suspended in media in an incubation chamber. In order to prevent cells from occluding the lumen, one of the open ends of the tubular framework can be affixed to a nozzle. Liquid media can be forced through this nozzle from a source chamber connected to the incubation chamber to create a current through the interior of the tubular framework. The other open end can be affixed to an outflow aperture which leads into a collection chamber from which the media can be recirculated through the source chamber. The tube can be detached from the nozzle and outflow aperture when incubation is complete. This method is described by Ballermann, B. J., et al., Int. Application No. WO 94/25584 and in U.S. application Ser. No. 08/430,768, both of which are incorporated herein by reference in its entirety.

In general, two three-dimensional frameworks can be combined into a tube in accordance with the invention using any of the following methods.

Two or more flat frameworks can be laid atop another and sutured together. This two-layer sheet can then be rolled up, and, as described above, joined together and secured.

One tubular scaffold that is to serve as the inner layer can be inoculated with PPDCs and incubated. A second scaffold can be grown as a flat strip with width slightly larger than the outer circumference of the tubular framework. After appropriate growth is attained, the flat framework can be wrapped around the outside of the tubular scaffold followed by closure of the seam of the two edges of the flat framework and, preferably, securing the flat framework to the inner tube.

Two or more tubular meshes of slightly differing diameters can be grown separately. The framework with the smaller diameter can be inserted inside the larger one and secured.

For each of these methods, more layers can be added by reapplying the method to the double-layered tube. The scaffolds can be combined at any stage of growth of the PPDCs, and incubation of the combined scaffolds can be continued when desirable.

The lumenal aspect of the tubular construct can be comprised of or treated with materials that render the lumenal surface of the tubular scaffold non-thrombogenic. These treatments and materials may also promote and sustain endothelial growth, migration, and extracellular matrix deposition. Examples of these materials and treatments include but are not limited to natural materials such as basement membrane proteins such as laminin and Type IV collagen, synthetic materials such as ePTFE, and segmented polyurethaneurea silicones, such as PURSPAN (The Polymer Technology Group, Inc., Berkeley, Calif.). These materials can be further treated to render the lumenal surface of the tubular scaffold non-thrombogenic. Such treatments include anti-thrombotic agents such as heparin, and treatments which alter the surface charge of the material such as plasma coating.

In conjunction with the above, the cells, cell lysates and fractions, and therapeutic compositions of the invention can be used in conjunction with implantable devices. For example the cells, cell lysates and cell fractions can be coadminstered with, for example stents, artificial valves, ventricular assist devices, Guglielmi detachable coils and the like. As the devices may constitute the dominant therapy provided to an individual in need of such therapy, the cells and the like may be used as supportive or secondary therapy to assist in, stimulate, or promote proper healing in the area of the implanted device. The cells, lysates, cell fractions and therapeutic compositions of the invention may also be used to "pretreat" certain implantable devices, to minimize problems when they are used in vivo. Such pretreated devices, including coated devices may be better tolerated by patients receiving them, with decrease risk of local or systemic infection, or for example, restenosis or further occulision of blood vessels.

The therapeutic cell compositions, in certain embodiments also comprise cells that express at least one of interleukin 8; reticulon 1; chemokine (C-X-C motif) ligand 1 (melanoma growth stimulating activity, alpha); chemokine (C-X-C motif) ligand 6 (granulocyte chemotactic protein 2); chemokine (C-X-C motif) ligand 3; and tumor necrosis factor, alpha-induced protein 3; or which have reduced expression, relative to a human cell that is a fibroblast, a mesenchymal stem cell, or an iliac crest bone marrow cell, for at least one of: short stature homeobox 2; heat shock 27 kDa protein 2; chemokine (C-X-C motif) ligand 12 (stromal cell-derived factor 1); elastin (supravalvular aortic stenosis, Williams-Beuren syndrome); *Homo sapiens* mRNA; cDNA DKFZp586M2022 (from clone DKFZp586M2022); mesenchyme homeobox 2 (growth arrest-specific homeobox); sine oculis homeobox homolog 1 (*Drosophila*); crystallin, alpha B; dishevelled associated activator of morphogenesis 2; DKFZP586B2420 protein; similar to neuralin 1; tetranectin (plasminogen binding protein); src homology three (SH3) and cysteine rich domain; B-cell translocation gene 1, anti-proliferative; cholesterol 25-hydroxylase; runt-related transcription factor 3; hypothetical protein FLJ23191; interleukin 11 receptor, alpha; procollagen C-endopeptidase enhancer; frizzled homolog 7 (*Drosophila*); hypothetical gene BC008967; collagen, type VIII, alpha 1; tenascin C (hexabrachion); iroquois homeobox protein 5; hephaestin; integrin, beta 8; synaptic vesicle glycoprotein 2; *Homo sapiens* cDNA FLJ12280 fis, clone MAMMA1001744; cytokine receptor-like factor 1; potassium intermediate/small conductance calcium-activated channel, subfamily N, member 4; integrin, alpha 7; DKFZP586L151 protein; transcriptional co-activator with PDZ-binding motif (TAZ); sine oculis homeobox homolog 2 (*Drosophila*); KIAA1034 protein; early growth response 3; distal-less homeobox 5; hypothetical protein F1120373; aldo-keto reductase family 1, member C3 (3-alpha hydroxysteroid dehydrogenase, type II); biglycan; fibronectin 1; proenkephalin; integrin, beta-like 1 (with EGF-like repeat domains); *Homo sapiens* mRNA full length insert cDNA clone EUROIMAGE 1968422; EphA3; KIAA0367 protein; natriuretic peptide receptor C/guanylate cyclase C (atrionatriuretic peptide receptor C); hypothetical protein FLJ14054; *Homo sapiens* mRNA; cDNA DKFZp564B222 (from clone DKFZp564B222); vesicle-associated membrane protein 5 (myobrevin); EGF-containing fibulin-like extracellular matrix protein 1; BCL2/adenovirus EIB 19 kDa interacting protein 3-like; AE binding protein 1; cytochrome c oxidase subunit VIIa polypeptide 1 (muscle); neuroblastoma, suppression of tumorigenicity 1; insulin-like growth factor binding protein 2, 36 kDa.

Preferred therapeutic cell compositions also comprise cells which secrete at least one of MCP-1, IL-6, IL-8, GCP-2, HGF, KGF, FGF, HB-EGF, BDNF, TPO, MIP1a, RANTES, and TIMP 1; and do not secrete at least one of TGF-beta2, ANG2, PDGFbb, MIP1b, I309, MDC, and VEGF, as detected by ELISA.

In yet another of its aspects, the invention provides methods for treating a patient with a heart disease or injury comprising administering a therapeutic postpartum-derived cell composition to a patient with a disease or injury of the heart or circulatory system; and evaluating the patient for improvements in cardiac function. In certain preferred embodiments the heart disease is a cardiomyopathy, either idiopathic or with a known cause, and either ischemic or nonischemic in nature. While patients with any heart or circulatory disease will benefit from such therapy, patients with myocardial infarction caused by any condition may benefit by receiving the therapeutic cell compositions of the invention as discussed below. In other preferred embodiments, the disease of the heart or circulatory system comprises one or more of angioplasty, aneurysm, angina (angina pectoris), aortic stenosis, aortitis, arrhythmias, arteriosclerosis, arteritis, asymmetric septal hypertrophy (ASH), atherosclerosis, Athletic Heart Syndrome, atrial fibrillation and flutter, bacterial endocarditis, Barlow's Syndrome (mitral valve prolapse), bradycardia, Buerger's Disease (thromboangiitis obliterans), cardiomegaly, cardiomyopathy, carditis, carotid artery disease, coarctation of the aorta, congenital heart diseases (congenital heart defects), congestive heart failure (heart failure), coronary artery disease, Eisenmenger's Syndrome, embolism, endocarditis, erythromelalgia, fibrillation, fibromuscular dysplasia, heart block, heart murmur, hypertension, hypotension, idiopathic infantile arterial calcification, Kawasaki Disease (mucocutaneous lymph node syndrome, mucocutaneous lymph node disease, infantile polyarteritis), metabolic syndrome, microvascular angina, myocardial infarction (heart attacks), myocarditis, paroxysmal atrial tachycardia (PAT), periarteritis nodosa (polyarteritis, polyarteritis nodosa), pericarditis, peripheral vascular disease, phlebitis, pulmonary valve stenosis (pulmonic stenosis), Raynaud's Disease, renal artery stenosis, renovascular hypertension, rheumatic heart disease, septal defects, silent ischemia, syndrome X, tachycardia, Takayasu's Arteritis, Tetralogy of Fallot, transposition of the great vessels, tricuspid atresia, truncus arteriosus, valvular heart disease, varicose ulcers, varicose veins, vasculitis, ventricular septal defect, Wolff-Parkinson-White Syndrome, and endocardial cushion defect.

In still other preferred embodiments, the disease of the heart or circulatory system comprises one or more of acute rheumatic fever, acute rheumatic pericarditis, acute rheumatic endocarditis, acute rheumatic myocarditis, chronic rheumatic heart diseases, diseases of the mitral valve, mitral stenosis, rheumatic mitral insufficiency, diseases of aortic valve, diseases of other endocardial structures, ischemic heart disease (acute and subacute), angina pectoris, diseases of pulmonary circulation (acute pulmonary heart disease, pulmonary embolism, chronic pulmonary heart disease), kyphoscoliotic heart disease, pericarditis, myocarditis, endocarditis, endomyocardial fibrosis, endocardial fibroelastosis, atrioventricular block, cardiac dysrhythmias, myocardial degeneration, diseases of the circulatory system including cerebrovascular disease, occlusion and stenosis of precerebral arteries, occlusion of cerebral arteries, diseases of arteries, arterioles and capillaries (atherosclerosis, aneurysm) diseases of veins and lymphatics, and other diseases of circulatory system.

Measurement of improvement in patients receiving the therapeutic compositions provided herein can include any means known in the art, but preferred improvements include improvements in hemodynamic measurements including but not limited to chest cardiac output (CO), cardiac index (CI), pulmonary artery wedge pressures (PAWP), and cardiac index (CI), % fractional shortening (% FS), ejection fraction (EF), left ventricular ejection fraction (LVEF); left ventricular end diastolic diameter (LVEDD), left ventricular end systolic diameter (LVESD), contractility (e.g. dP/dt), pressure-volume loops, measurements of cardiac work, an increase in atrial or ventricular functioning; an increase in pumping efficiency, a decrease in the rate of loss of pumping efficiency, a decrease in loss of hemodynamic functioning; and a decrease in complications associated with cardiomyopathy. Biochemical measurements of improvement are also contemplated herein, for example production of certain cellular products or factors. The presence or absence of biological molecules, for example particular enzymes (or their activities), mRNAs, transcription factors, proteins, modified proteins, lipids, sterols, or the like may be shown to correlate with improvement in cardiac or circulatory health and the use of these measurements of improvement are also contemplated for use herein. Also contemplated herein as a indications of improvement are histological changes deemed beneficial or for example, indicia of angiogenesis or improved vascularization.

In some presently preferred embodiments, the methods comprise inducing the therapeutic postpartum-derived cells to differentiate along mesenchymal lineage, towards cardiomyogenic, angiogenic and vasculogenic phenotypes, or even further towards cells such as cardiomyocytes, endothelial cells, myocardial cells, epicardial cells, vascular endothelial cells, smooth muscle cells (e.g. vascular smooth muscle cells), or towards cells of the excitatory and conductive systems, and progenitors or more primitive relatives of the foregoing. Such cells are discussed above, and the methods and factors for differentiating the cells, assessing the induction of cells to differentiate, and the uses of such cells for the therapeutic compositions is analogous. Also the therapeutic cell compositions can integrate into the patient's heart, or alternatively can provide support for growth or stimulation to differentiate for naturally present cardiac stem cells present. Therapeutic cells can be coadministered with cell lysates, or with other allogeneic, syngeneic or autologous cells. The survival of the cells delivered in administering the therapeutic cell compositions is not determinative of the success or results of their use, rather the improvement in cardiac or circulatory health is outcome determinative. Thus, the cells need not integrate and beat with the patient's heart, or into blood vessels, but rather the indicia of improvements in cardiac or circulatory health in the patient before and after treatment preferably include at least one of objective measurements of cardiac or circulatory health, and subjective assessment (including self-assessment) of the patient's condition. A successful treatment could thus comprise treatment of a patient with a cardiomyopathy with a therapeutic cell composition comprising the PPDCs, in the presence or absence of another cell type. For example, and not by way of limitation, the PPDCs preferably at least partially integrate, multiply, or survive in the patient. In other preferred embodiments, the patient experiences benefits from the therapy, for example from the ability of the PPDCs to support the growth of other cells, including stem cells or progenitor cells present in the heart, from the tissue ingrowth or vascularization of the tissue, and from the presence of beneficial cellular factors, chemokines, cytokines and the like, but the cells do not integrate or multiply in the patient. In another embodiment, the patient benefits from the therapeutic treatment with the PPDCs, but the cells do not survive for a prolonged period in the patient. In one embodiment, the cells gradually decline in number, viability or biochemical activity, in other embodiments, the decline in cells may be preceded by a period of activity, for example growth, division, or biochemical activity. In other embodiments, senescent, nonviable or even dead cells are able to have a beneficial therapeutic effect.

The administering is preferably in vivo by transplanting, implanting, injecting, fusing, delivering via catheter, or providing as a matrix-cell complex, or any other means known in the art for providing cell therapy.

Patients with myocardial infarction caused by any condition may benefit by receiving the therapeutic cell compositions of the invention. Such treatment is preferably provided within a reasonable therapeutic window after the cardiac event. Presently, it is preferred that treatment with the cells or compositions of the invention be initiated within 30 days of the myocardial infarction. Treatment within 1-21 days is preferred. It is also comtemplated herein that beneficial effects of certain applications, for example by intravenous injection where the cells home to the damaged site, will allow treatment far more rapidly. For example, it is presently contemplated that treatment in close temporal relation with the myocardial infarction or similar cardiac event may be beneficial. In preferred embodiments, treatment with the therapeutic cell compositions is within twenty four hours of the cardiac event. Also preferred is treatment within 12, 8, or even four hours. More preferably treatment is given with two hours. Treatment within one hour of the event is more preferred, with treatment within 30 minutes, or even 15 minutes most preferred. Also provided herein are kits for use in the treatment of myocardial infarction. The kits provide the therapeutic cell composition which can be prepared in a pharmaceutically acceptable form, for example by mixing with a pharmaceutically acceptable carrier, and an applicator, along with instructions for use. Ideally the kit can be used in the field, for example in a physician's office, or by an emergency care provider to be applied to a patient diagnosed as having had a myocardial infarction or similar cardiac event.

The invention also provides in another aspect, methods for treating a patient with a disease of the heart or circulatory system comprising administering a therapeutic postpartum-derived cell composition to a patient with a disease of the heart or circulatory system; and evaluating the patient for improvements in cardiac function, wherein the administering is with a population of another cell type. Administration of cocultures, mixed populations or other nonclonal populations are preferred. Other cell types which can be coadministered are stem cells in certain embodiments, while in others, myoblasts, myocytes, cardiomyoblasts, cardiomyocytes, or progenitors of myoblasts, myocytes, cardiomyoblasts, or cardiomyocytes are used.

Also provided herein are methods for treating a patient with a disease of the heart or circulatory system comprising administering a therapeutic postpartum-derived cell composition to a patient with a disease of the heart or circulatory system; and evaluating the patient for improvements in cardiac function, wherein the therapeutic cell composition is administered as a matrix-cell complex. In certain embodiments, the matrix is a scaffold, preferably bioabsorbable, comprising at least the postpartum-derived cells.

Kits for the therapeutic application of the populations and cocultures of the invention are also provided. Where used for treatment of cardiomyopathy, or other scheduled treatment, the kits include a therapeutic cell composition, with or without a matrix, and with or without a coculture present. The kits also optionally include a means of administering the cells, for example by injection, and a pharmaceutically-acceptable carrier for the cells, if required. The kits include instructions for use of the cells. Kits prepared for field hospital use, such as for military use may include full-procedure supplies including tissue scaffolds, surgical sutures, and the like, where the cells are to be used in conjunction with repair of acute cardiac injuries.

The invention also provides for banking of tissues, cells, populations and therapeutic cell compositions of the invention. As discussed above the cells are readily cryopreserved. The invention therefore provides methods of cryopreserving the cells in a bank, wherein the cells are stored frozen and associated with a complete characterization of the cells based on immunological, biochemical and genetic properties of the cells. The cells so frozen can be used for autologous, syngeneic, or allogeneic therapy, depending on the requirements of the procedure and the needs of the patient. Preferably, the information on each cryopreserved sample is stored in a computer which is searchable based on the requirements of the surgeon, procedure and patient with suitable matches being made based on the characterization of the cells or populations. Preferably, the cells of the invention are grown and expanded to the desired quantity of cells and therapeutic cell compositions are prepared either separately or as cocultures, in the presence or absence of a matrix or support. While for some applications it may be preferable to use cells freshly prepared, the remainder can be cryopreserved and banked by freezing the cells and entering the information in the computer to associate the computer entry with the samples. Even where it is not necessary to match a source or donor with a recipient of such cells, for immunological purposes, the bank system makes it easy to match, for example, desirable biochemical or genetic properties of the banked cells to the therapeutic needs. Upon matching of the desired properties with a particle banked sample, the sample is retrieved and readied for therapeutic use. Cell lysates prepared as described herein may also be cryopreserved and banked in accordance with the present invention.

In another aspect of the invention, kits for the growth and maintenance, the isolation and the use of the umbilical-derived cells are provided. The cells, cell lysates, soluble cell fractions, membrane fractions and matrices can conveniently be employed as parts of kits, for example, for a kit for culture or implantation. The invention provides a kit including the UDCs and additional components, including instructions for growth or maintenance, isolation, or use of the cells or cell fractions, together with for example, matrix (e.g., a scaffold) material, hydrating agents (e.g., physiologically-compatible saline solutions, prepared cell culture media), cell culture substrates (e.g., culture dishes, plates, vials, etc.), cell culture media (whether in liquid or dehydrated form), antibiotic compounds, hormones, and the like. Kits for growth can for example include all of the components of the Growth Medium as used herein, including serum, for example fetal bovine serum. While the kit can include any such components, preferably it includes all ingredients necessary for its intended use. If desired, the kit also can include cells (typically cryopreserved), which can be seeded into the lattice as described herein. Kits for isolation will contain everything required to practice the isolation methods as provided herein, except for the umbilicus tissue which should be obtained fresh or frozen from a tissue bank at the time of isolation. The surgical equipment for dissociating the tissue, preferred enzymes, or choices of enzymes in stable form are provided, as are the buffers and medium, cell strainers and the like, as required or preferred for the method as disclosed above.

Detailed instructions with optional steps and lists of suppliers of optional or alternative materials are also conveniently provided. Control cells can be included for comparison of the cells isolated to, for example the UDC cultures deposited with the ATCC. Kits for utilizing the umbilicus-derived cells preferably contain populations of the cells, or therapeutic compositions comprising the cells, components and products, or fractions or conditioned media derived from the cells as described above. In some embodiments, the kits may include one or more cell populations, including at least UDCs and a pharmaceutically acceptable carrier (liquid, semi-solid or solid). The populations in some embodiments are homogenous or even clonal cell lines of UDCs. In other embodiments, the kits include other cell lines for use in coculture. Therapeutic application kits preferably include additional bioactive agents as desired for example anithrombogenic agents, anti-inflammatory agents, antiapoptotic agents, and immunosuppressive or immunomodulatory compounds. The kits also optionally may include a means of administering the cells, for example by injection. The kits further may include instructions for use of the cells. Kits prepared for field hospital use, such as for military use, may include full-procedure supplies including tissue scaffolds, surgical sutures, and the like, where the cells are to be used in conjunction with repair of acute injuries. Kits for assays and in vitro methods as described herein may contain one or more of (1) UDCs or fractions, components or products of UDCs, (2) reagents for practicing the in vitro method, (3) other cells or cell populations, as appropriate, for example for cocultures and (4) instructions for conducting the in vitro method. Kits for the preparation of cell-derived components can include both the components required for growth of the cells and the components required for preparing the cell fraction of interest, along with instructions for obtaining the desired fraction from the cells. Kits for production of and collection of conditioned media are also provided herein and include cells, medium, collection vessels, instructions, standards for assaying the secreted molecules of interest and the like.

The following examples describe several aspects of embodiments of the invention in greater detail. These examples are provided to further illustrate, not to limit, aspects of the invention described herein.

Example 1

Isolation of Cells from Postpartum Tissues

Summary

Postpartum cells have been isolated from full- and pre-term placental and umbilical cord tissues. A highly preferred way of isolating cells from these tissues is by using a combination of digestive enzymes. Particularly preferred are collagenase, hyaluronidase and dispase. This combination results in the isolation of a cell population with good expansion and differentiation potentials. Other enzyme combinations used have yielded cell populations that can also be expanded.

Introduction

Populations of cells from placental and umbilical cord tissues were isolated. Postpartum umbilicus and placenta were obtained upon births of either full- or pre-term pregnancies. Cells were harvested from five separate donors of umbilicus and placental tissue. Different methods of cell isolation were tested for their ability to yield cells with: 1) the potential to differentiate into cells with different phenotypes, a characteristic common to stem cells, or 2) the potential to provide critical trophic factors useful for other cells and tissues.

Methods & Materials

Umbilical Cell Isolation

Umbilical cords were obtained from National Disease Research Interchange (NDRI, Philadelphia, Pa.). The tissues were obtained following normal deliveries. The cell isolation protocol was performed aseptically in a laminar flow hood. To remove blood and debris, the cord was washed in phosphate buffered saline (PBS; Invitrogen, Carlsbad, Calif.) in the presence of 10,000 Units of antimycotic and antibiotic per 100 milliliters of PBS (Invitrogen Carlsbad, Calif.). The tissues were then mechanically dissociated in 150 $cm^2$ tissue culture plates in the presence of 50 milliliters of medium (DMEM-Low glucose or DMEM-High glucose; Invitrogen), until the tissue was minced into a fine pulp. The chopped tissues were transferred to 50 milliliter conical tubes (approximately 5 grams of tissue per tube). The tissue was then digested in either DMEM-Low glucose medium or DMEM-High glucose medium, each containing 10,000 Units of antimycotic and antibiotic per 100 milliliters of PBS and digestion enzymes. In some experiments an enzyme mixture of collagenase and dispase was used ("C:D;" collagenase (Sigma, St Louis, Mo.), 500 Units/milliliter; and dispase (Invitrogen), 50 Units/milliliter in DMEM:-Low glucose medium). In other experiments a mixture of collagenase, dispase and hyaluronidase ("C:D:H") was used (collagenase, 500 Units/milliliter; dispase, 50 Units/milliliter; and hyaluronidase (Sigma), 5 Units/milliliter, in DMEM:-Low glucose). The conical tubes containing the tissue, medium and digestion enzymes were incubated at 37° C. in an orbital shaker (Environ, Brooklyn, N.Y.) at 225 rpm for 2 hrs.

After digestion, the tissues were centrifuged at 150×g for 5 minutes, the supernatant was aspirated. The pellet was resuspended in 20 milliliters of Growth Medium (DMEM:Low glucose (Invitrogen), 15 percent (v/v) fetal bovine serum (FBS; defined bovine serum; Lot#AND18475; Hyclone, Logan, Utah), 0.001% (v/v) 2-mercaptoethanol (Sigma), 1 milliliter per 100 milliliters of antibiotic/antimycotic (10,000 Units per milliliter penicillin, 10,000 micrograms per milliliter streptomycin, 25 micrograms per milliliter amphotericin B; Invitrogen, Carlsbad, Calif.)). The cell suspension was filtered through a 70-micrometer nylon cell strainer (Nalge Nunc International, Rochester, N.Y.). An additional 5 milliliters rinse comprising Growth Medium was passed through the strainer. The cell suspension was then passed through a 40-micrometer nylon cell strainer (Nalge Nunc International) and chased with a rinse of an additional 5 milliliters of Growth Medium.

The filtrate was resuspended in Growth Medium (total volume 50 milliliters) and centrifuged at 150×g for 5 minutes. The supernatant was aspirated and the cells were resuspended in 50 milliliters of fresh Growth Medium. This process was repeated twice more.

Upon the final centrifugation supernatant was aspirated and the cell pellet was resuspended in 5 milliliters of fresh Growth Medium. The number of viable cells was determined using trypan blue staining. Cells were then cultured under standard conditions.

The cells isolated from umbilical cord cells were seeded at 5,000 cells/$cm^2$ onto gelatin-coated T-75 $cm^2$ flasks (Corning Inc., Corning, N.Y.) in Growth Medium. After 2 days, spent medium was aspirated from the flasks. Cells were washed with PBS three times to remove debris and blood-derived cells. Cells were then replenished with Growth Medium and allowed to grow to confluence (about 10 days from passage 0) to passage 1. On subsequent passages (from passage 1 to 2 etc), cells reached sub-confluence (75-85 percent confluence) in 4-5 days. For these subsequent passages, cells were seeded at 5000 cells/cm$^2$. Cells were grown in a humidified incubator with 5 percent carbon dioxide and 20 percent oxygen, at 37° C.

Placental Cell Isolation

Placental tissue was obtained from NDRI (Philadelphia, Pa.). The tissues were from a pregnancy and were obtained at the time of a normal surgical delivery. Placental cells were isolated as described for umbilical cell isolation.

The following description applies to the isolation of separate populations of maternal-derived and neonatal-derived cells from placental tissue.

The cell isolation protocol was performed aseptically in a laminar flow hood. The placental tissue was washed in phosphate buffered saline (PBS; Invitrogen, Carlsbad, Calif.) in the presence of antimycotic and antibiotic (penicillin, 10,000 Units/milliliter; streptomycin, 10,000 micrograms/milliliter; amphotericin B, 25 micrograms/milliliter; Invitrogen) to remove as much blood and debris as practical. The placental tissue was then dissected into three sections: neonatal aspect, the villous region, the maternal aspect.

The separated sections were individually washed several times in PBS with antibiotic/antimycotic to further remove blood and debris. In this manner, substantially all the blood was removed. Each section was then mechanically dissociated in 150 cm$^2$ tissue culture plates in the presence of 50 milliliters of DMEM:Low glucose (Invitrogen), to a fine pulp. The pulp was transferred to 50 milliliter conical tubes. Each tube contained approximately 5 grams of tissue. The tissue was digested in either DMEM-Low glucose DMEM-High glucose medium containing 10,000 Units of antimycotic and antibiotic per 100 milliliters of PBS and digestion enzymes. In some experiments an enzyme mixture of collagenase and dispase ("C:D") was used containing collagenase (Sigma, St Louis, Mo.) at 500 Units/milliliter and dispase (Invitrogen) at 50 Units/milliliter in DMEM:-Low glucose medium. In other experiments, a mixture of collagenase, dispase and hyaluronidase (C:D:H) was used (collagenase, 500 Units/milliliter; dispase, 50 Units/milliliter; and hyaluronidase (Sigma), 5 Units/milliliter in DMEM:-Low glucose). The conical tubes containing the tissue, medium, and digestion enzymes were incubated for 2 h at 37° C. in an orbital shaker (Environ, Brooklyn, N.Y.) at 225 rpm.

After digestion, the tissues were centrifuged at 150×g for 5 minutes, the resultant supernatant was aspirated off. The pellet was resuspended in 20 milliliters of Growth Medium. The cell suspension was filtered through a 70 micrometer nylon cell strainer (Nalge Nunc International, Rochester, N.Y.), and rinsed with 5 milliliters of Growth Medium. The total cell suspension was passed through a 40 micrometer nylon cell strainer (Nalge Nunc International) and rinsed with an additional 5 milliliters of Growth Medium.

The filtrate was resuspended in Growth Medium (total volume 50 milliliters) and centrifuged at 150×g for 5 minutes. The supernatant was aspirated and the cell pellet was resuspended in 50 milliliters of fresh Growth Medium. This process was repeated twice more. After the final centrifugation, supernatant was aspirated and the cell pellet was resuspended in 5 milliliters of fresh Growth Medium. A cell count was determined using the trypan blue Exclusion test. Cells were cultured under standard conditions.

LIBERASE Cell Isolation

Cells were isolated from postpartum tissues in DMEM-Low glucose medium with LIBERASE (2.5 milligrams per milliliter, Blendzyme 3; (Roche Applied Sciences, Indianapolis, Ind.)) and hyaluronidase (5 Units/milliliter, Sigma). Digestion of the tissue and isolation of the cells was as described for other digestions above, with the LIBERASE/hyaluronidase mixture used instead of the C:D or C:D:H enzyme mixture. Tissue digestion with LIBERASE resulted in the isolation of cell populations from postpartum tissues that expanded readily.

Cell Isolation Using Other Enzyme Combinations

Procedures were compared for isolating cells from the umbilical cord using differing enzyme combinations. Enzymes compared for digestion included: i) collagenase; ii) dispase; iii) hyaluronidase; iv) collagenase:dispase mixture (C:D); v) collagenase:hyaluronidase mixture (C:H); vi) dispase:hyaluronidase mixture (D:H); and vii) collagenase:dispase:hyaluronidase mixture (C:D:H). Differences in cell isolation utilizing these different enzyme digestion conditions were observed (Table 1-1).

Isolation of Cells from Residual Blood in the Cords

Other attempts were made to isolate pools of cells from umbilical cords by different approaches. In one instance umbilical cord was sliced and washed with Growth Medium to dislodge the blood clots and gelatinous material. The mixture of blood, gelatinous material and Growth Medium was collected and centrifuged at 150×g. The pellet was resuspended and seeded onto gelatin coated flasks in Growth Medium. Cell populations that readily expanded were isolated.

Isolation of Cells from Cord Blood

Cells were also isolated from cord blood samples attained from NDRI. The isolation protocol used here was that of International Patent Application PCT/US2002/029971 by Ho et al. Samples (50 milliliter and 10.5 milliliters, respectively) of umbilical cord blood (NDRI, Philadelphia Pa.) were mixed with lysis buffer (filter-sterilized 155 millimolar ammonium chloride, 10 millimolar potassium bicarbonate, 0.1 millimolar EDTA buffered to pH 7.2 (all components from Sigma, St. Louis, Mo.)). Cells were lysed at a ratio of 1:20 cord blood to lysis buffer. The resulting cell suspension was vortexed for 5 seconds, and incubated for 2 minutes at ambient temperature. The lysate was centrifuged (10 minutes at 200×g). The cell pellet was resuspended in complete minimal essential medium (Gibco, Carlsbad Calif.) containing 10 percent fetal bovine serum (Hyclone, Logan Utah), 4 millimolar glutamine (Mediatech Herndon, Va.), 100 Units penicillin per 100 milliliters and 100 micrograms streptomycin per 100 milliliters (Gibco, Carlsbad, Calif.). The resuspended cells were centrifuged (10 minutes at 200×g), the supernatant was aspirated, and the cell pellet was washed in complete medium. Cells were seeded directly into either T75 flasks (Corning, N.Y.), T75 laminin-coated flasks, or T175 fibronectin-coated flasks (both Becton Dickinson, Bedford, Mass.).

Isolation of Postpartum Cells Using Different Enzyme Combinations and Growth Conditions To determine whether cell populations can be isolated under different conditions and expanded under a variety of conditions immediately after isolation, cells were digested in Growth Medium with or without 0.001 percent (v/v) 2-mercaptoethanol (Sigma, St. Louis, Mo.), using the C:D:H enzyme combination, according to the procedures provided above. Placental cells so isolated were seeded under a variety of conditions. All cells were grown in the presence of penicillin/streptomycin. (Table 1-2).

Isolation of Postpartum Cells Using Different Enzyme Combinations and Growth Conditions In all conditions tested, cells attached and expanded well from about passage 0 to 1 (Table 1-2). Cells in conditions 5-8 and 13-16 proliferated well up to 4 passages after seeding at which point they were cryopreserved. All cells were banked for later investigation.

Results

Cell Isolation Using Different Enzyme Combinations

The combination of C:D:H enzymes provided the best cell yield following isolation, and generated cells which expanded for many more generations in culture than the other conditions (Table 1). An expandable cell population was not attained using collagenase or hyaluronidase alone. No attempt was made to determine if this result is specific to the collagenase that was tested.

Isolation of Postpartum Cells Using Different Enzyme Combinations and Growth Conditions Cells attached and expanded well from about passage 0 to 1 under all conditions tested for enzyme digestion and growth (Table 1-2). Cells in experimental conditions 5-8 and 13-16 proliferated well up to 4 passages after seeding, at which point they were cryopreserved. All cells were banked for further investigation.

Isolation of Cells from Residual Blood in the Cords

Nucleated cells attached and grew rapidly. These cells were analyzed by flow cytometry and were similar to cells obtained by enzyme digestion.

Isolation of Cells from Cord Blood

The preparations contained red blood cells and platelets. No nucleated cells attached and divided during the first 3 weeks. The medium was changed 3 weeks after seeding and no cells were observed to attach and grow.

Discussion and Conclusion

Populations of cells can be isolated from umbilical and placental tissue most efficiently using the enzyme combination collagenase (a metalloprotease), dispase (a neutral protease) and hyaluronidase (a mucolytic enzyme which breaks down hyaluronic acid). LIBERASE Blendzyme, which is a commercial blend of collagenase and another protease may also be used. In the present study Blendzyme 3 which contains collagenase (4 Wunsch units/g) and thermolysin (1714 casein Units/g) was also used together with hyaluronidase to isolate cells. Cells isolated with these enzymes expand readily over many passages, for example, when cultured in Growth Medium on gelatin coated plastic.

Cells were also isolated from residual blood in the cords, but not cord blood. The presence of cells in blood clots washed from the tissue, that adhere and grow under the conditions used, may be due to cells being released during the dissection process. Other explanations may include the migration of cells from the matrix.

Recommendation

Use of C:D:H enzyme combinations for isolation of cell populations from postpartum tissues is preferred. Cells isolated using this combination of enzymes have been extensively characterized and have many desirable properties. LIBERASE extracted cells and cells treated with other enzyme combination cells provide useful cells with expansion potential. It may be useful to choose a process or method for cell isolation that helps minimize handling and transfer of the tissue. Such methods may include mechanical digestion for example with a blender, tissue homogenizer, and the like.

References

1. HO, Tony, W.; KOPEN, Gene, C.; RIGHTER, William, F.; RUTKOWSKI, J., Lynn; HERRING, W., Joseph; RAGAGLIA, Vanessa; WAGNER, Joseph; WO2003025149 A2 CELL POPULATIONS WHICH CO-EXPRESS CD49C AND CD90, NEURONYX, INC., Application No. PCT/US2002/029971, Filed 20020920, A2 Published 20030327, A3 Published 20031218.

TABLE 1-1

Isolation of cells from umbilical cord tissue using varying enzyme combinations

| Enzyme Digest | Cells Isolated | Cell Expansion |
|---|---|---|
| Collagenase | X | X |
| Dispase | + (>10 h) | + |
| Hyaluronidase | X | X |
| Collagenase:Dispase | ++ (<3 h) | ++ |
| Collagenase:Hyaluronidase | ++ (<3 h) | + |
| Dispase:Hyaluronidase | + (>10 h) | + |
| Collagenase:Dispase:Hyaluronidase | +++ (<3 h) | +++ |

Key:
+ = good,
++ = very good,
+++ = excellent,
X = no success

TABLE 1-2

Isolation and culture expansion of postpartum cells under varying conditions:

| Condition | Medium | 15% FBS | BME | Gelatin | 20% $O_2$ | Growth Factors |
|---|---|---|---|---|---|---|
| 1 | DMEM-Lg | Y | Y | Y | Y | N |
| 2 | DMEM-Lg | Y | Y | Y | N (5%) | N |
| 3 | DMEM-Lg | Y | Y | N | Y | N |
| 4 | DMEM-Lg | Y | Y | N | N (5%) | N |
| 5 | DMEM-Lg | N (2%) | Y | N (Laminin) | Y | EGF/FGF (20 ng/milliliter) |
| 6 | DMEM-Lg | N (2%) | Y | N (Laminin) | N (5%) | EGF/FGF (20 ng/milliliter) |
| 7 | DMEM-Lg | N (2%) | Y | N (Fibrone) | Y | PDGF/VEGF |
| 8 | DMEM-Lg | N (2%) | Y | N (Fibrone) | N (5%) | PDGF/VEGF |
| 9 | DMEM-Lg | Y | N | Y | Y | N |
| 10 | DMEM-Lg | Y | N | Y | N (5%) | N |
| 11 | DMEM-Lg | Y | N | N | Y | N |
| 12 | DMEM-Lg | Y | N | N | N (5%) | N |
| 13 | DMEM-Lg | N (2%) | N | N (Laminin) | Y | EGF/FGF (20 ng/milliliter) |
| 14 | DMEM-Lg | N (2%) | N | N (Laminin) | N (5%) | EGF/FGF (20 ng/milliliter) |
| 15 | DMEM-Lg | N (2%) | N | N (Fibrone) | Y | PDGF/VEGF |
| 16 | DMEM-Lg | N (2%) | N | N (Fibrone) | N (5%) | PDGF/VEGF |

Example 2

Growth Characteristics of Postpartum Cells

Summary

Commercially viable cell products must be able to be produced in sufficient quantities to provide therapeutic treatment to patients in need of the treatment. Postpartum cells can be expanded in culture for such purposes. Comparisons were made of the growth of postpartum cells in culture to that of other cell populations including mesenchymal stem cells. The data demonstrate that postpartum cell lines as developed herein can expand for greater than 40 doublings to provide sufficient cell numbers, for example, for pre-clinical banks. Furthermore, these postpartum cell populations can be expanded well from low- or high-density seeding. This study has demonstrated that mesenchymal stem cells, in contrast, cannot be expanded to obtain large quantities of cells.

Introduction

The cell expansion potential of postpartum cells was compared to other populations of isolated stem cells. The art of cell expansion to senescence is referred to as Hayflick's limit (Hayflick L. The longevity of cultured human cells. *J. Am. Geriatr. Soc.* 22(1):1-12, 1974; Hayflick L. The strategy of senescence. *Gerontologist* 14(1):37-45), 1974). Senescence is defined as the point at which cell division stops completely, i.e., when the cell loses its ability to proliferate and expand. Postpartum-derived cells are highly suited for therapeutic use because they can be readily expanded to sufficient cell numbers.

Materials and Methods
Gelatin-Coating Flasks

Tissue culture plastic flasks were coated by adding 20 milliliters of a 2% (w/v) gelatin (Type B: 225 Bloom; Sigma, St Louis, Mo.) solution each to T75 flasks (Corning, Corning, N.Y.) for 20 minutes at room temperature. After removing the gelatin solution, 10 milliliters phosphate-buffered saline (PBS) (Invitrogen, Carlsbad, Calif.) were added and then aspirated.

Comparison of Expansion Potential of Postpartum Cells vs. Other Stem Cell and Non-Stem Cell Populations For comparison of growth expansion potential the following cell populations were utilized; i) Mesenchymal stem cells (MSC; Cambrex, Walkersville, Md.); ii) Adipose-derived cells (U.S. Pat. No. 6,555,374 B1; U.S. Patent Application US20040058412); iii) Normal dermal skin fibroblasts (cc-2509 lot #9F0844; Cambrex, Walkersville, Md.); iv) Umbilical-derived cells; and vi) Placental-derived cells. Cells were initially seeded at 5,000 cells/cm$^2$ on gelatin-coated T75 flasks in Growth Medium.

For subsequent passages, cell cultures were treated as follows: After trypsinization, viable cells were counted after trypan blue staining. Cell suspension (50 microliters) was combined with trypan blue (50 ml, Sigma, St. Louis Mo.). Viable cell numbers were estimated using a hemocytometer.

Following counting, cells were seeded at 5,000 cells/cm$^2$ onto gelatin-coated T 75 flasks in 25 ml of fresh Growth Medium. Cells were grown under standard atmospheric conditions (5 percent carbon dioxide) at 37° C. in the presence of 20 percent oxygen and 75 percent nitrogen (v/v). The Growth Medium was changed twice per week. When cells reached about 85 percent confluence they were passaged; this process was repeated until the cells reached senescence.

At each passage, cells were trypsinized and counted. The viable cell yield, population doubling [ln(cell final/cell initial)/ln 2] and doubling time (time in culture (h)/population doubling) were calculated. For the purposes of determining optimal cell expansion, the total cell yield per passage was determined by multiplying the total yield for the previous passage by the expansion factor for each passage (i.e. expansion factor=cell final/cell initial).

Expansion of Potential of Cell Banks at Low Density

The expansion potential of cells banked at passage 10 was also tested. A different set of conditions was used. Normal dermal skin fibroblasts (cc-2509 lot #9F0844; Cambrex, Walkersville, Md.), umbilical-derived cells, and placenta-derived cells were tested. These cell populations had been banked at passage 10 previously, having been cultured at 5,000 cells/cm$^2$ at each passage to that point. The effect of cell density on the cell populations following cell thaw at passage 10 was determined. Cells were thawed under standard conditions, counted using trypan blue staining. Thawed cells were then seeded at 1000 cells/cm$^2$ in Growth Medium. Cells were grown under standard atmospheric conditions at 37° C. Growth Medium was changed twice a week and cells were passaged as they reached about 85% confluence. Cells were subsequently passaged until senescence, i.e., until they could not be expanded any further. Cells were trypsinized and counted at each passage. The cell yield, population doubling (ln(cell final/cell initial)/ln 2) and doubling time (time in culture (h)/population doubling). The total cell yield per passage was determined by multiplying total yield for the previous passage by the expansion factor for each passage (i.e., expansion factor=cell final/cell initial).

Expansion of Postpartum Cells at Low Density from Initial Cell Seeding

The expansion potential of freshly isolated postpartum cell cultures under low cell seeding conditions was tested in another experiment. Umbilical and placental cells were isolated as described herein. Cells were seeded at 1000 cells/cm$^2$ and passaged as described above until senescence. Cells were grown under standard atmospheric conditions at 37° C. Growth Medium was changed twice per week. Cells were passaged as they reached about 85% confluence. At each passage, cells were trypsinized and counted by trypan blue staining. The cell yield, population doubling (ln(cell final/cell initial)/ln 2) and doubling time (time in culture (h)/population doubling) were calculated for each passage. The total cell yield per passage was determined by multiplying the total yield for the previous passage by the expansion factor for each passage (i.e. expansion factor=cell final/cell initial). Cells were grown on gelatin and non-gelatin coated flasks.

Expansion of Clonal Neonatal Placental Cells

Cloning was used in order to expand a population of neonatal cells successfully from placental tissue. Following isolation of three differential cell populations from the placenta (as described herein), these cell populations were expanded under standard growth conditions and then karyotyped to reveal the identity of the isolated cell populations. Since these cells were isolated from a mother who delivered a boy it was very simple to distinguish between the male and female chromosomes by performing metaphase spreads. These experiments demonstrated that cells isolated from the neonatal aspect were primarily karyotype-positive for neonatal phenotpye, and cells isolated from the maternal aspect were primarily karyotype-positive for maternal cells, those cells isolated from the villous region were karyotype-positive for both neonatal and maternal phenotypes. Subcloning of populations derived from neonatal and maternal aspects is required to ensure that clonal populations are obtained for both neonatal and maternal cells.

Expansion of Cells in Low Oxygen Culture Conditions

It has been demonstrated that low $O_2$ cell culture conditions can improve cell expansion in certain circumstances (Csete, Marie; Doyle, John; Wold, Barbara J.; McKay, Ron; Studer, Lorenz. Low oxygen culturing of central nervous system progenitor cells. US20040005704). In order to determine if cell expansion of postpartum-derived cells could be improved by altering cell culture conditions, cultures of umbilical-derived cells were grown in low oxygen conditions. Cells were seeded at 5000 cells/cm$^2$ in Growth Medium on gelatin coated flasks. Cells were initially cultured under standard atmospheric conditions through passage 5, at which point they were transferred to low oxygen (5% $O_2$) culture conditions.

Other Growth Conditions

In other experiments cells were expanded on non-coated, collagen-coated, fibronectin-coated, laminin-coated and Matrigel-coated plates. Cultures have been demonstrated to expand well on these different matrices.

Results

Comparison of Expansion Potential of Postpartum Cells vs. Other Stem Cell and Non-Stem Cell Populations Both umbilical-derived and placenta-derived cells expanded for greater than 40 passages generating cell yields of >1E17 cells in 60 days. In contrast, MSCs and fibroblasts senesced after <25 days and <60 days, respectively. Although both adipose-derived and omental cells expanded for almost 60 days they generated total cell yields of 4.5E12 and 4.24E13 respectively. Thus, when seeded at 5000 cells/$cm^2$ under the experimental conditions utilized, postpartum-derived cells expanded much better than the other cell types grown under the same conditions (Table 1).

Expansion of Potential of Cell Banks at Low Density

Umbilical-derived, placental-derived and fibroblast cells expanded for greater than 10 passages generating cell yields of >1E11 cells in 60 days (Table 2). After 60 days under these conditions the fibroblasts became senescent whereas the umbilical-derived and placental-derived cell populations senesced after 80 days, completing >50 and >40 population doublings respectively.

Expansion of Postpartum Cells at Low Density from Initial Cell Seeding

Placental-derived cells were expanded at low density (1,000 cells/$cm^2$) on gelatin-coated and uncoated plates or flasks. Growth potential of these cells under these conditions was good. The cells expanded readily in a log phase growth. The rate of cell expansion was similar to that observed when placental-derived cells were seeded at 5000 cells/$cm^2$ on gelatin-coated flasks in Growth Medium. No differences were observed in cell expansion potential between culturing on either uncoated flasks or gelatin-coated flasks. However, cells appeared phenotypically much smaller on gelatin-coated flasks and more larger cell phenotypes were observed on uncoated flasks.

Expansion of Clonal Neonatal and Maternal Placental Cells

The expansion of a clonal cell populations of placental-derived cells isolated from the neonatal and maternal aspects of the placenta are studied. Populations derived from neotal and maternal aspects are serially diluted and then seeded onto gelatin-coated plates in Growth Medium for expansion at 1 cell/well in 96-well gelatin coated plates. From this initial cloning, expansive clones are identified, trypsinized and reseeded in 12 well gelatin coated plates in Growth Medium and then subsequently passaged into T25 gelatin coated flasks at 5,000 cells/$cm^2$ in Growth Medium. Subcloning is then performed to ensure that a clonal population of cells had been identified. For subcloning experiments cells are trypsinized and reseeded at 0.5 cells/well. The subclones that grow well are then expanded in gelatin-coated T25 flasks at 5,000 cells/$cm^2$. Cells are subsequently passaged at 5,000 cells/$cm^2$ in T75 flasks. Karyotyping confirms that clones so-derived are neotal or maternal in nature.

Expansion of Cells in Low Oxygen Culture Conditions

Cells expanded well under the reduced oxygen conditions, however, culturing under low oxygen conditions does not appear to have a significant effect on cell expansion for postpartum-derived cells. These results are preliminary in the sense that any ultimate conclusions to be made regarding the effect of reduced oxygen should include data from experiments on growing cells in low oxygen from initial isolation. Standard atmospheric conditions have already proven successful for growing sufficient numbers of cells, and low oxygen culture is compatible with, but not required for, the growth of postpartum-derived cells.

Discussion and Conclusions

The current cell expansion conditions of growing isolated postpartum-derived cells at densities of about 5000 cells/$cm^2$, in Growth Medium on gelatin-coated or uncoated flasks, under standard atmospheric oxygen, are sufficient to generate large numbers of cells at passage 11. Furthermore, the data suggest that the cells can be readily expanded using lower density culture conditions (e.g. 1000 cells/$cm^2$). Postpartum-derived cell expansion in low oxygen conditions also facilitates cell expansion, although no incremental improvement in cell expansion potential has yet been observed when utilizing these conditions for growth. Presently, culturing postpartum-derived cells under standard atmospheric conditions is preferred for generating large pools of cells. However, when the culture conditions are altered, postpartum-derived cell expansion can likewise be altered. This strategy may be used to enhance the proliferative and differentiative capacity of these cell populations.

Under the conditions utilized, while the expansion potential of MSC and adipose-derived cells is limited, postpartum-derived cells expand readily to large numbers.

Recommendations:

In order to optimize expansion and scale-up of postpartum-derived cell cultures additional work with new methods for cell expansion, media conditions, extracellular matrix conditions for cellular attachment and cell density would be useful. However, with all these changes the cell potential would have to be re-determined.

References

1) Hayflick L. The longevity of cultured human cells. *J Am Geriatr Soc.* 1974 January; 22(1):1-12.
2) Hayflick L. The strategy of senescence. *Gerontologist.* 1974 February; 14(1):37-45.
3) Patent US20040058412
4) Patent US20040048372
6) Csete, Marie; (Ann Arbor, Mich.); Doyle, John; (South Pasadena, Calif.); Wold, Barbara J.; (San Marino, Calif.); McKay, Ron; (Bethesda, Md.); Studer, Lorenz; (New York, N.Y.). Low oxygen culturing of central nervous system progenitor cells. US20040005704.

TABLE 1

Growth characteristics for different cell populations grown to senescence

| Cell Type | Senescence | Total Population Doublings | Total Cell Yield |
|---|---|---|---|
| MSc | 24 d | 8 | 4.72 E7 |
| Adipose-derived | 57 d | 24 | 4.5 E12 |
| Fibroblasts | 53 d | 26 | 2.82 E13 |
| Umbilical | 65 d | 42 | 6.15 E17 |
| Placenta | 80 d | 46 | 2.49 E19 |

TABLE 2

Growth characteristics for different cell populations using low density growth expansion from passage 10 till senescence

| Cell Type | Senescence | Total Population Doublings | Total Cell Yield |
|---|---|---|---|
| Fibroblast (P10) | 80 d | 43.68 | 2.59 E11 |
| Umbilical (P10) | 80 d | 53.6 | 1.25 E14 |
| Placental (P10) | 60 d | 32.96 | 6.09 E12 |

Example 3

Growth of Postpartum Cells in Medium Containing D-Valine

Summary

Culture media containing D-valine instead of the L-valine isoform reportedly selectively inhibit the growth of fibroblast-like cells in culture. To determine whether postpartum-derived cells can grow in medium containing D-valine, cells derived from placenta and umbilical cord were grown in medium containing D-valine for 4 weeks. The cells did not proliferate and eventually died. Medium containing D-valine is not suitable for selectively growing postpartum-derived cells. L-valine is required for postpartum-derived cell proliferation and long-term viability.

Introduction

It has been reported that medium containing D-valine instead of the normal L-valine isoform can be used to selectively inhibit the growth of fibroblast-like cells in culture (Hongpaisan, 2000; Sordillo et al., 1988). It was not previously known whether postpartum-derived cells can grow in medium containing D-valine.

Methods & Materials

Placenta-derived cells (P3), fibroblasts (P9) and umbilical-derived cells (P5) were seeded at $5 \times 10^3$ cells/cm$^2$ in gelatin-coated T75 flasks (Corning, Corning, N.Y.). After 24 hours the medium was removed and the cells were washed with phosphate buffered saline (PBS) (Gibco, Carlsbad, Calif.) to remove residual medium. The medium was replaced with a Modified Growth Medium (DMEM with D-valine (special order Gibco), 15% (v/v) dialyzed fetal bovine serum (Hyclone, Logan, Utah), 0.001% (v/v) betamercaptoethanol (Sigma), penicillin/streptomycin (Gibco)).

Results

Placenta-derived, umbilical-derived, and fibroblast cells seeded in the D-valine-containing medium did not proliferate, unlike cells seeded in Growth Medium containing dialyzed serum. Fibroblasts cells changed morphologically, increasing in size and changing shape. All of the cells died and eventually detached from the flask surface after 4 weeks.

Discussion and Conclusion

Postpartum-derived cells require L-valine for cell growth and to maintain long-term viability. L-valine should therefore not be removed from the Growth Medium for postpartum-derived cells.

References

Hongpaisan J. (2000) Inhibition of proliferation of contaminating fibroblasts by D-valine in cultures of smooth muscle cells from human myometrium. *Cell Biol Int.* 24:1-7.

Sordillo L M, Oliver S P, Akers R M. (1988) Culture of bovine mammary epithelial cells in D-valine modified medium: selective removal of contaminating fibroblasts. *Cell Biol Int Rep.* 12:355-64.

Example 4

Karyotype Analysis of PPDCs

Cell lines used in cell therapy are preferably homogeneous and free from any contaminating cell type. Cells used in cell therapy should have a normal chromosome number (46) and structure. To identify postpartum placental and umbilical cord cell lines that are homogeneous and free from cells of non-postpartum tissue origin, karyotypes of cell samples were analyzed.

Materials and Methods

PPDCs from postpartum tissue of a male neonate were cultured in Growth Media. Postpartum tissue from a male neonate (X,Y) was selected to allow distinction between neonatal-derived cells and maternal derived cells (X,X). Cells were seeded at 5,000 cells per square centimeter in Growth Medium in a T25 flask (Corning, Corning, N.Y.) and expanded to 80% confluence. A T25 flask containing cells was filled to the neck with Growth Medium. Samples were delivered to a clinical cytogenetics lab by courier (estimated lab to lab transport time is one hour). Chromosome analysis was performed by the Center for Human & Molecular) Genetics at the New Jersey Medical School, Newark, N.J. Cells were analyzed during metaphase when the chromosomes are best visualized. Of twenty cells in metaphase counted, five were analyzed for normal homogeneous karyotype number (two). A cell sample was characterized as homogeneous if two karyotypes were observed. A cell sample was characterized as heterogeneous if more than two karyotypes were observed. Additional metaphase cells were counted and analyzed when a heterogeneous karyotype number (four) was identified.

Results

All cell samples sent for chromosome analysis were interpreted by the cytogenetics laboratory staff as exhibiting a normal appearance. Three of the sixteen cell lines analyzed exhibited a heterogeneous phenotype (XX and XY) indicating the presence of cells derived from both neonatal and maternal origins (Table 4-1). Cells derived from tissue Placenta-N were isolated from the neonatal aspect of placenta. At passage zero, this cell line appeared homogeneous XY. However, at passage nine, the cell line was heterogeneous (XX/XY), indicating a previously undetected presence of cells of maternal origin.

TABLE 4-1

Karyotype results of PPDCs.

| Tissue | passage | Metaphase cells counted | Metaphase cells analyzed | number of karyotype | ISCN Karyotype |
|---|---|---|---|---|---|
| Placenta | 22 | 20 | 5 | 2 | 46, XX |
| Umbilical | 23 | 20 | 5 | 2 | 46, XX |
| Umbilical | 6 | 20 | 5 | 2 | 46, XY |

TABLE 4-1-continued

Karyotype results of PPDCs.

| Tissue | passage | Metaphase cells counted | Metaphase cells analyzed | number of karyotype | ISCN Karyotype |
|---|---|---|---|---|---|
| Placenta | 2 | 20 | 5 | 2 | 46, XX |
| Umbilical | 3 | 20 | 5 | 2 | 46, XX |
| Placenta-N | 0 | 20 | 5 | 2 | 46, XY |
| Placenta-V | 0 | 20 | 5 | 2 | 46, XY |
| Placenta-M | 0 | 21 | 5 | 4 | 46, XY[18]/46, XX[3] |
| Placenta-M | 4 | 20 | 5 | 2 | 46, XX |
| Placenta-N | 9 | 25 | 5 | 4 | 46, XY[5]/46, XX[20] |
| Placenta-N C1 | 1 | 20 | 5 | 2 | 46, XY |
| Placenta-N C3 | 1 | 20 | 6 | 4 | 46, XY[2]/46, XX[18] |
| Placenta-N C4 | 1 | 20 | 5 | 2 | 46, XY |
| Placenta-N C15 | 1 | 20 | 5 | 2 | 46, XY |
| Placenta-N C20 | 1 | 20 | 5 | 2 | 46, XY |

Key: N—Neonatal aspect; V—villous region; M—maternal aspect; C—clone

Summary

Chromosome analysis identified placenta- and umbilical cord-derived PPDCs whose karyotypes appear normal as interpreted by a clinical cytogenetic laboratory. Karyotype analysis also identified cell lines free from maternal cells, as determined by homogeneous karyotype.

Example 5

Evaluation of Postpartum-Derived Cell Surface Markers by Flow Cytometry

Summary

Characterization of cell surface protein expression, or "markers" by flow cytometry of cultured cell lines labeled with fluorescent monoclonal antibodies enables the determination of a cell line's identity. Placental and umbilicus-derived postpartum cells were characterized by flow cytometry for the expression of cell surface markers CD10, CD13, CD31, CD34, CD44, CD45, CD73, CD90, CD117, CD141, PDGFr-alpha, HLA-A,B,C and HLA-DR, DP,DQ. Both placenta- and umbilicus-derived postpartum cells are positive for the expression of CD10, CD13, CD44, CD73, CD90, PDGFr-alpha, HLA-A, B, C and negative for the expression of CD31, CD34, CD44, CD45, CD73, CD90, CD117, CD141 and HLA-DR, DP, DQ. This expression pattern was consistent across variables such as cell donor, passage, culture vessel surface coating, and digestion enzymes used in isolation. This expression pattern was also consistent in cells isolated from the maternal aspect, neonatal aspect and villous region of the placenta.

Introduction

Characterization of cell surface proteins or "markers" by flow cytometry can be used to determine a cell line's identity. The consistency of expression can be determined from multiple donors, and in cells exposed to different processing and culturing conditions. Postpartum cell lines isolated from the placenta and umbilicus were characterized (by flow cytometry) providing a profile for the identification of these cell lines.

Materials and Methods
Media
Cells were cultured in Growth Media.
Culture Vessels
Cells were cultured in plasma-treated T75, T150, and T225 tissue culture flasks (Corning, Corning, N.Y.) until confluent.

The growth surfaces of the flasks were coated with gelatin by incubating 2% (w/v) gelatin (Sigma, St. Louis, Mo.) for 20 minutes at room temperature.
Antibody Staining
Adherent cells in flasks were washed in phosphate buffered saline (PBS); (Gibco, Carlsbad, Mo.) and detached with Trypsin/EDTA (Gibco, Carlsbad, Mo.). Cells were harvested, centrifuged, and resuspended in 3% (v/v) FBS in PBS at a cell concentration of $1\times10^7$ per milliliter. In accordance to the manufacture's specifications, antibody to the cell surface marker of interest (see below) was added to one hundred microliters of cell suspension and the mixture was incubated in the dark for 30 minutes at 4° C. After incubation, cells were washed with PBS and centrifuged to remove unbound antibody. Cells were resuspended in 500 microliters PBS and analyzed by flow cytometry.
Flow Cytometry Analysis
Flow cytometry analysis was performed with a FACScalibur instrument (Becton Dickinson, San Jose, Calif.).
Antibodies to Cell Surface Markers
The following antibodies to cell surface markers were used.

| Antibody | Manufacture | Catalog Number |
|---|---|---|
| CD10 | BD Pharmingen (San Diego, CA) | 555375 |
| CD13 | BD Pharmingen | 555394 |
| CD31 | BD Pharmingen | 555446 |
| CD34 | BD Pharmingen | 555821 |
| CD44 | BD Pharmingen | 555478 |
| CD45RA | BD Pharmingen | 555489 |
| CD73 | BD Pharmingen | 550257 |
| CD90 | BD Pharmingen | 555596 |
| CD117 | BD Pharmingen | 340529 |
| CD141 | BD Pharmingen | 559781 |
| PDGFr-alpha | BD Pharmingen | 556002 |
| HLA-A, B, C | BD Pharmingen | 555553 |
| HLA-DR, DP, DQ | BD Pharmingen | 555558 |
| IgG-FITC | Sigma (St. Louis, MO) | F-6522 |
| IgG-PE | Sigma | P-4685 |

Placenta and Umbilicus Comparison
Placenta cells were compared to umbilicus at passage 8.
Passage to Passage Comparison
Placenta and umbilicus were analyzed at passages 8, 15, and 20.
Donor to Donor Comparison
To compare differences among donors, placenta cells from different donors were compared to each other, and umbilical from different donors were compared to each other.

Surface Coating Comparison

Placenta cultured on gelatin-coated flasks was compared to placenta cultured on uncoated flasks. Umbilicus cultured on gelatin-coated flasks was compared to umbilicus cultured on uncoated flasks.

Digestion Enzyme Comparison

Four treatments used for isolation and preparation of cells were compared. Cells isolated from placenta by treatment with 1) collagenase; 2) collagenase/dispase; 3) collagenase/hyaluronidase; and 4) collagenase/hyaluronidase/dispase were compared.

Placental Layer Comparison

Cells isolated from the maternal aspect of placental tissue were compared to cells isolated from the villous region of placental tissue and cells isolated from the neonatal fetal aspect of placenta.

Results

Placenta vs. Umbilicus Comparison

Placental- and umbilical-derived cells analyzed by flow cytometry showed positive expression of CD10, CD13, CD44, CD73, CD90, PDGFr-alpha and HLA-A, B, C, indicated by the increased values of fluorescence relative to the IgG control. These cells were negative for detectable expression of CD31, CD34, CD45, CD117, CD141, and HLA-DR, DP, DQ, indicated by fluorescence values comparable to the IgG control. Variations in florescence values of positive curves was accounted for. The mean (i.e. CD13) and range (i.e. CD90) of the positive curves showed some variation, but the curves appear normal, confirming a homogenous population. Both curves individually exhibited values greater than the IgG control.

Passage to Passage Comparison—Placenta

Placenta-derived cells at passages 8, 15, and 20 analyzed by flow cytometry all were positive for expression of CD10, CD 13, CD44, CD73, CD90, PDGFr-alpha and HLA-A, B, C, as reflected in the increased value of fluorescence relative to the IgG control. The cells were negative for expression of CD31, CD34, CD45, CD 117, CD 141, and HLA-DR, DP, DQ having fluorescence values consistent with the IgG control. Variations in florescence detection values of the positive curves was accounted for. While range (i.e. CD10) of the positive curves varied, the curves were normal, confirming a homogenous population, and each curves individually exhibited values greater than the IgG control.

Passage to Passage Comparison—Umbilicus

Umbilical cells at passage 8, 15, and 20 analyzed by flow cytometry all expressed CD10, CD13, CD44, CD73, CD90, PDGFr-alpha and HLA-A, B, C, indicated by increased fluorescence relative to the IgG control. These cells were negative for CD31, CD34, CD45, CD117, CD141, and HLA-DR, DP, DQ, indicated by fluorescence values consistent with the IgG control. Variations in florescence detection values of positive curves were within expected ranges. While the means (i.e. CD13) of the positive curves varied all curves individually exhibited values greater than the IgG control.

Donor to Donor Comparison—Placenta

Placenta-derived cells isolated from separate donors analyzed by flow cytometry each expressed CD10, CD13, CD44, CD73, CD90, PDGFr-alpha and HLA-A, B, C, with increased values of fluorescence relative to the IgG control. The cells were negative for expression of CD31, CD34, CD45, CD117, CD 141, and HLA-DR, DP, DQ as indicated by fluorescence value consistent with the IgG control. Variations in florescence detection values of positive curves are within expected ranges. While the range (i.e. CD44) of the positive curves varied, the curves appeared normal, confirming a homogenous population, and both curves individually exhibit values greater than the IgG control.

Donor to Donor Comparison—Umbilicus

Umbilical-derived cells isolated from separate donors analyzed by flow cytometry each showed positive expression of CD10, CD13, CD44, CD73, CD90, PDGFr-alpha and HLA-A, B, C, reflected in the increased values of fluorescence relative to the IgG control. These cells were negative for expression of CD31, CD34, CD45, CD 17, CD141, and HLA-DR, DP, DQ with fluorescence values consistent with the IgG control. Variations in florescence detection values of positive curves were accounted for. While the mean (i.e. CD10) of the positive curves varied, both curves individually exhibited values greater than the IgG control.

The Effect of Surface Coating with Gelatin on Placenta-Derived Cells

Placenta-derived cells expanded on either gelatin-coated or uncoated flasks analyzed by flow cytometry all expressed of CD10, CD13, CD44, CD73, CD90, PDGFr-alpha and HLA-A, B, C, reflected in the increased values of fluorescence relative to the IgG control. These cells were negative for expression of CD31, CD34, CD45, CD117, CD141, and HLA-DR, DP, DQ indicated by fluorescence values consistent with the IgG control. Variations in florescence detection values of positive curves were noted. While the mean (i.e. PDGFr-alpha) of the positive curves varied both curves individually exhibited values greater than the IgG control.

The Effect of Surface Coating with Gelatin on Umbilicus-Derived Cells

Umbilical cells expanded on gelatin and uncoated flasks analyzed by flow cytometry all were positive for expression of CD10, CD13, CD44, CD73, CD90, PDGFr-alpha and HLA-A, B, C, with increased values of fluorescence relative to the IgG control. These cells were negative for expression of CD31, CD34, CD45, CD117, CD141, and HLA-DR, DP, DQ, with fluorescence values consistent with the IgG control.

Does the Enzyme Digestion Procedure Used for Preparation and Isolation of the Cells Effect the Cell Surface Marker Profile?

Placenta cells isolated using various digestion enzymes analyzed by flow cytometry all expressed CD10, CD13, CD44, CD73, CD90, PDGFr-alpha and HLA-A, B, C, as indicated by the increased values of fluorescence relative to the IgG control. These cells were negative for expression of CD31, CD34, CD45, CD 117, CD 141, and HLA-DR, DP, DQ as indicated by fluorescence values consistent with the IgG control. Variations in the CD13 mean florescence value were noted. While the CD 13 mean fluorescence values of the collagenase-treated cells was less than the other CD 13 curves, the collagenase-treated curve appeared normal, confirming a homogenous population, and it individually exhibited values greater than the IgG control.

Placental Layer Comparison

Cells isolated from the maternal, villous, and neonatal layers of the placenta, respectively, analyzed by flow cytometry showed positive expression of CD10, CD13, CD44, CD73, CD90, PDGFr-alpha and HLA-A, B, C, as indicated by the increased value of fluorescence relative to the IgG control. These cells were negative for expression of CD31, CD34, CD45, CD117, CD 141, and HLA-DR, DP, DQ as indicated by fluorescence values consistent with the IgG control. Variations in florescence detection values of positive curves were noted. While the mean and range (i.e. CD10, CD73) of the positive curves varied, both curves appeared normal, confirming a homogenous population, and all curves individually exhibit values greater than the IgG control.

Conclusions

Analysis of placenta- and umbilicus-derived postpartum cells by flow cytometry has established of an identity of these cell lines. Placenta- and umbilicus-derived postpartum cells are positive for CD10, CD 13, CD44, CD73, CD90, PDGFr-alpha, HLA-A,B,C and negative for CD31, CD34, CD45, CD117, CD141 and HLA-DR, DP, DQ. This identity was consistent between variations in variables including the donor, passage, culture vessel surface coating, digestion enzymes, and placental layer. Some variation in individual fluorescence value histogram curve means and ranges were observed, but all positive curves under all conditions tested were normal and expressed fluorescence values greater than the IgG control, thus confirming that the cells comprise a homogenous population which has positive expression of the markers.

Example 6

Analysis of Postpartum Tissue-Derived Cells Using Oligonucleotide Arrays

Oligonucleotide arrays were used to compare gene expression profiles of umbilicus- and placenta-derived cells with fibroblasts, human mesenchymal stem cells, and another cell line derived from human bone marrow. This analysis provided a characterization of the postpartum-derived cells and identified unique molecular markers for these cells.

Materials and Methods
Isolation and Culture of Cells

Postpartum tissue-derived cells. Human umbilical cords and placenta were obtained from National Disease Research Interchange (NDRI, Philadelphia, Pa.) from normal full term deliveries with patient consent. The tissues were received and cells were isolated as described in Example 1. Cells were cultured in Growth Medium on gelatin-coated tissue culture plastic flasks. The cultures were incubated at 37° C. with 5% $CO_2$.

Fibroblasts.

Human dermal fibroblasts were purchased from Cambrex Incorporated (Walkersville, Md.; Lot number 9F0844) and ATCC CRL-1501 (CCD39SK). Both lines were cultured in DMEM/F12 medium (Invitrogen, Carlsbad, Calif.) with 10% (v/v) fetal bovine serum (Hyclone) and penicillin/streptomycin (Invitrogen). The cells were grown on standard tissue-treated plastic.

Human Mesenchymal Stem Cells (hMSC).

hMSCs were purchased from Cambrex Incorporated (Walkersville, Md.; Lot numbers 2F1655, 2F1656 and 2F1657) and cultured according to the manufacturer's specifications in MSCGM Media (Cambrex). The cells were grown on standard tissue cultured plastic at 37° C. with 5% $CO_2$.

Human Ileac Crest Bone Marrow Cells (ICBM).

Human ileac crest bone marrow was received from NDRI with patient consent. The marrow was processed according to the method outlined by Ho, et al. (WO03/025149). The marrow was mixed with lysis buffer (155 millimolar $NH_4Cl$, 10 millimolar $KHCO_3$, and 0.1 millimolar EDTA, pH 7.2) at a ratio of 1 part bone marrow to 20 parts lysis buffer. The cell suspension was vortexed, incubated for 2 minutes at ambient temperature, and centrifuged for 10 minutes at 500×g. The supernatant was discarded and the cell pellet was resuspended in Minimal Essential Medium-alpha (Invitrogen) supplemented with 10% (v/v) fetal bovine serum and 4 millimolar glutamine. The cells were centrifuged again and the cell pellet was resuspended in fresh medium. The viable mononuclear cells were counted using trypan-blue exclusion (Sigma, St. Louis, Mo.). The mononuclear cells were seeded in tissue-cultured plastic flasks at $5 \times 10^4$ cells/cm$^2$. The cells were incubated at 37° C. with 5% $CO_2$ at either standard atmospheric $O_2$ or at 5% $O_2$. Cells were cultured for 5 days without a media change. Media and non-adherent cells were removed after 5 days of culture. The adherent cells were maintained in culture.

Isolation of mRNA and GENECHIP Analysis.

Actively growing cultures of cells were removed from the flasks with a cell scraper in cold phosphate buffered saline (PBS). The cells were centrifuged for 5 minutes at 300×g. The supernatant was removed and the cells were resuspended in fresh PBS and centrifuged again. The supernatant was removed and the cell pellet was immediately frozen and stored at −80° C. Cellular mRNA was extracted and transcribed into cDNA. cDNA was then transcribed into cRNA and biotin-labeled. The biotin-labeled cRNA was hybridized with Affymetrix GENECHIP HG-U133A oligonucleotide arrays (Affymetrix, Santa Clara Calif.). The hybridizations and data collection were performed according to the manufacturer's specifications. The hybridization and data collection was performed according to the manufacturer's specifications. Data analyses were performed using "Significance Analysis of Microarrays" (SAM) version 1.21 computer software (Tusher, V. G. et al., 2001, *Proc. Natl. Acad. Sci. USA* 98: 5116-5121).

Results

Fourteen different populations of cells were analyzed in this study. The cells along with passage information, culture substrate, and culture media are listed in Table 6-1.

TABLE 6-1

Cells analyzed by the microarray study. The cells lines are listed by their identification code along with passage at the time of analysis, cell growth substrate, and growth media.

| Cell Population | Passage | Substrate | Media |
|---|---|---|---|
| Umbilical (022803) | 2 | Gelatin | DMEM, 15% FBS, βME |
| Umbilical (042103) | 3 | Gelatin | DMEM, 15% FBS, βME |
| Umbilical (071003) | 4 | Gelatin | DMEM, 15% FBS, βME |
| Placenta (042203) | 12 | Gelatin | DMEM, 15% FBS, βME |
| Placenta (042903) | 4 | Gelatin | DMEM, 15% FBS, βME |
| Placenta (071003) | 3 | Gelatin | DMEM, 15% FBS, βME |
| ICBM (070203) (5% $O_2$) | 3 | Plastic | MEM 10% FBS |
| ICBM (062703) (std $O_2$) | 5 | Plastic | MEM 10% FBS |
| ICBM (062703) (5% $O_2$) | 5 | Plastic | MEM 10% FBS |
| hMSC (Lot 2F1655) | 3 | Plastic | MSCGM |
| hMSC (Lot 2F1656) | 3 | Plastic | MSCGM |
| hMSC (Lot 2F1657) | 3 | Plastic | MSCGM |
| hFibroblast (9F0844) | 9 | Plastic | DMEM-F12, 10% FBS |
| hFibroblast (CCD39SK) | 4 | Plastic | DMEM-F12, 10% FBS |

The data were evaluated by Principle Component Analysis. Analysis revealed 290 genes that were expressed in different relative amounts in the cells tested. This analysis provided relative comparisons between the populations.

Table 6-2 shows the Euclidean distances that were calculated for the comparison of the cell pairs. The Euclidean distances were based on the comparison of the cells based on the 290 genes that were differentially expressed among the cell types. The Euclidean distance is inversely proportional to similarity between the expression of the 290 genes.

TABLE 6-2

The Euclidean Distances for the Cell Pairs.
The Euclidean distance was calculated for the cell types using the 290 genes that were expressed differently between the cell types. Similarity between the cells is inversely proportional to the Euclidean distance.

| Cell Pair | Euclidean Distance |
| --- | --- |
| ICBM-hMSC | 24.71 |
| Placenta-umbilical | 25.52 |
| ICBM-Fibroblast | 36.44 |
| ICBM-placenta | 37.09 |
| Fibroblast-MSC | 39.63 |
| ICBM-Umbilical | 40.15 |
| Fibroblast-Umbilical | 41.59 |
| MSC-Placenta | 42.84 |
| MSC-Umbilical | 46.86 |
| ICBM-placenta | 48.41 |

Tables 6-3, 6-4, and 6-5 show the expression of genes increased in placenta-derived cells (Table 6-3), increased in umbilical cord-derived cells (Table 6-4), and reduced in umbilical cord and placenta-derived cells (Table 6-5).

TABLE 6-3

Genes which are specifically increased in expression in the placenta-derived cells as compared to the other cell lines assayed.
Genes Increased in Placenta-Derived Cells

| Probe Set ID | Gene Name | NCBI Accession Number |
| --- | --- | --- |
| 209732_at | C-type (calcium dependent, carbohydrate-recognition domain) lectin, superfamily member 2 (activation-induced) | AF070642 |
| 206067_s_at | Wilms tumor 1 | NM_024426 |
| 207016_s_at | aldehyde dehydrogenase 1 family, member A2 | AB015228 |
| 206367_at | Renin | NM_000537 |

TABLE 6-3-continued

Genes which are specifically increased in expression in the placenta-derived cells as compared to the other cell lines assayed.
Genes Increased in Placenta-Derived Cells

| Probe Set ID | Gene Name | NCBI Accession Number |
| --- | --- | --- |
| 210004_at | oxidized low density lipoprotein (lectin-like) receptor 1 | AF035776 |
| 214993_at | Homo sapiens, clone IMAGE: 4179671, mRNA, partial cds | AF070642 |
| 202178_at | protein kinase C, zeta | NM_002744 |
| 209780_at | hypothetical protein DKFZp564F013 | AL136883 |
| 204135_at | downregulated in ovarian cancer 1 | NM_014890 |
| 213542_at | Homo sapiens mRNA; cDNA DKFZp547K1113 (from clone DKFZp547K1113) | AI246730 |

TABLE 6-4

Genes which are specifically increased in expression in umbilical cord-derived cells as compared to the other cell lines assayed.
Genes Increased in Umbilicus-Derived Cells

| Probe Set ID | Gene Name | NCBI Accession Number |
| --- | --- | --- |
| 202859_x_at | Interleukin 8 | NM_000584 |
| 211506_s_at | Interleukin 8 | AF043337 |
| 210222_s_at | reticulon 1 | BC000314 |
| 204470_at | chemokine (C-X-C motif) ligand 1 (melanoma growth stimulating activity | NM_001511 |
| 206336_at | chemokine (C-X-C motif) ligand 6 (granulocyte chemotactic protein 2) | NM_002993 |
| 207850_at | Chemokine (C-X-C motif) ligand 3 | NM_002090 |
| 203485_at | reticulon 1 | NM_021136 |
| 202644_s_at | tumor necrosis factor, alpha-induced protein 3 | NM_006290 |

TABLE 6-5

Genes which were decreased in expression in the umbilical cord and placenta cells as compared to the other cell lines assayed.
Genes Decreased in Umbilicus- and Placenta-Derived Cells

| Probe Set ID | Gene name | NCBI Accession Number |
| --- | --- | --- |
| 210135_s_at | short stature homeobox 2 | AF022654.1 |
| 205824_at | heat shock 27 kDa protein 2 | NM_001541.1 |
| 209687_at | chemokine (C-X-C motif) ligand 12 (stromal cell-derived factor 1) | U19495.1 |
| 203666_at | chemokine (C-X-C motif) ligand 12 (stromal cell-derived factor 1) | NM_000609.1 |
| 212670_at | elastin (supravalvular aortic stenosis, Williams-Beuren syndrome) | AA479278 |
| 213381_at | Homo sapiens mRNA; cDNA DKFZp586M2022 (from clone DKFZp586M2022) | N91149 |
| 206201_s_at | mesenchyme homeobox 2 (growth arrest-specific homeobox) | NM_005924.1 |
| 205817_at | Sine oculis homeobox homolog 1 (Drosophila) | NM_005982.1 |
| 209283_at | crystallin, alpha B | AF007162.1 |
| 212793_at | dishevelled associated activator of morphogenesis 2 | BF513244 |
| 213488_at | DKFZP586B2420 protein | AL050143.1 |
| 209763_at | similar to neuralin 1 | AL049176 |
| 205200_at | Tetranectin (plasminogen binding protein) | NM_003278.1 |
| 205743_at | src homology three (SH3) and cysteine rich domain | NM_003149.1 |
| 200921_s_at | B-cell translocation gene 1, anti-proliferative | NM_001731.1 |
| 206932_at | cholesterol 25-hydroxylase | NM_003956.1 |
| 204198_s_at | runt-related transcription factor 3 | AA541630 |
| 219747_at | hypothetical protein FLJ23191 | NM_024574.1 |
| 204773_at | Interleukin 11 receptor, alpha | NM_004512.1 |
| 202465_at | Procollagen C-endopeptidase enhancer | NM_002593.2 |
| 203706_s_at | Frizzled homolog 7 (Drosophila) | NM_003507.1 |

TABLE 6-5-continued

Genes which were decreased in expression in the umbilical cord and placenta cells as compared to the other cell lines assayed.
Genes Decreased in Umbilicus- and Placenta-Derived Cells

| Probe Set ID | Gene name | NCBI Accession Number |
| --- | --- | --- |
| 212736_at | hypothetical gene BC008967 | BE299456 |
| 214587_at | Collagen, type VIII, alpha 1 | BE877796 |
| 201645_at | Tenascin C (hexabrachion) | NM_002160.1 |
| 210239_at | iroquois homeobox protein 5 | U90304.1 |
| 203903_s_at | Hephaestin | NM_014799.1 |
| 205816_at | integrin, beta 8 | NM_002214.1 |
| 203069_at | synaptic vesicle glycoprotein 2 | NM_014849.1 |
| 213909_at | *Homo sapiens* cDNA FLJ12280 fis, clone MAMMA1001744 | AU147799 |
| 206315_at | cytokine receptor-like factor 1 | NM_004750.1 |
| 204401_at | potassium intermediate/small conductance calcium-activated channel, subfamily N, member 4 | NM_002250.1 |
| 216331_at | integrin, alpha 7 | AK022548.1 |
| 209663_s_at | integrin, alpha 7 | AF072132.1 |
| 213125_at | DKFZP586L151 protein | AW007573 |
| 202133_at | transcriptional co-activator with PDZ-binding motif (TAZ) | AA081084 |
| 206511_s_at | Sine oculis homeobox homolog 2 (*Drosophila*) | NM_016932.1 |
| 213435_at | KIAA1034 protein | AB028957.1 |
| 206115_at | early growth response 3 | NM_004430.1 |
| 213707_s_at | distal-less homeobox 5 | NM_005221.3 |
| 218181_s_at | hypothetical protein FLJ20373 | NM_017792.1 |
| 209160_at | aldo-keto reductase family 1, member C3 (3-alpha hydroxysteroid dehydrogenase, type II) | AB018580.1 |
| 213905_x_at | Biglycan | AA845258 |
| 201261_x_at | Biglycan | BC002416.1 |
| 202132_at | transcriptional co-activator with PDZ-binding motif (TAZ) | AA081084 |
| 214701_s_at | fibronectin 1 | AJ276395.1 |
| 213791_at | Proenkephalin | NM_006211.1 |
| 205422_s_at | Integrin, beta-like 1 (with EGF-like repeat domains) | NM_004791.1 |
| 214927_at | *Homo sapiens* mRNA full length insert cDNA clone EUROIMAGE 1968422 | AL359052.1 |
| 206070_s_at | EphA3 | AF213459.1 |
| 212805_at | KIAA0367 protein | AB002365.1 |
| 219789_at | natriuretic peptide receptor C/guanylate cyclase C (atrionatriuretic peptide receptor C) | AI628360 |
| 219054_at | hypothetical protein FLJ14054 | NM_024563.1 |
| 213429_at | *Homo sapiens* mRNA; cDNA DKFZp564B222 (from clone DKFZp564B222) | AW025579 |
| 204929_s_at | vesicle-associated membrane protein 5 (myobrevin) | NM_006634.1 |
| 201843_s_at | EGF-containing fibulin-like extracellular matrix protein 1 | NM_004105.2 |
| 221478_at | BCL2/adenovirus E1B 19 kDa interacting protein 3-like | AL132665.1 |
| 201792_at | AE binding protein 1 | NM_001129.2 |
| 204570_at | cytochrome c oxidase subunit VIIa polypeptide 1 (muscle) | NM_001864.1 |
| 201621_at | neuroblastoma, suppression of tumorigenicity 1 | NM_005380.1 |
| 202718_at | Insulin-like growth factor binding protein 2, 36 kDa | NM_000597.1 |

Tables 6-6, 6-7, and 6-8 show the expression of genes increased in human fibroblasts (Table 6-6), ICBM cells (Table 6-7), and MSCs (Table 6-8).

TABLE 6-6

Genes which were increased in expression in fibroblasts as compared to the other cell lines assayed.
Genes increased in fibroblasts dual specificity phosphatase 2
KIAA0527 protein
*Homo sapiens* cDNA: FLJ23224 fis, clone ADSU02206
dynein, cytoplasmic, intermediate polypeptide 1
ankyrin 3, node of Ranvier (ankyrin G)
inhibin, beta A (activin A, activin AB alpha polypeptide)
ectonucleotide pyrophosphatase/phosphodiesterase 4 (putative function)
KIAA1053 protein
microtubule-associated protein 1A
zinc finger protein 41
HSPC019 protein
*Homo sapiens* cDNA: FLJ23564 fis, clone LNG10773
*Homo sapiens* mRNA; cDNA DKFZp564A072 (from clone DKFZp564A072)

TABLE 6-6-continued

Genes which were increased in expression in fibroblasts as compared to the other cell lines assayed.
Genes increased in fibroblasts LIM protein (similar to rat protein kinase C-binding enigma)
inhibitor of kappa light polypeptide gene enhancer in B-cells, kinase complex-associated protein
hypothetical protein FLJ22004
Human (clone CTG-A4) mRNA sequence
ESTs, Moderately similar to cytokine receptor-like factor 2; cytokine receptor CRL2 precursor [*Homo sapiens*]
transforming growth factor, beta 2
hypothetical protein MGC29643
antigen identified by monoclonal antibody MRC OX-2
putative X-linked retinopathy protein

TABLE 6-7

Genes which were increased in expression in the
ICBM-derived cells as compared to the other cell lines assayed.
Genes Increased In ICBM Cells cardiac ankyrin repeat protein
MHC class I region ORF
integrin, alpha 10
hypothetical protein FLJ22362
UDP-N-acetyl-alpha-D-galactosamine: polypeptide
N-acetylgalactosaminyltransferase 3 (GalNAc-T3)
interferon-induced protein 44
SRY (sex determining region Y)-box 9
(campomelic dysplasia, autosomal sex-reversal)
keratin associated protein 1-1
hippocalcin-like 1
jagged 1 (Alagille syndrome)
proteoglycan 1, secretory granule

TABLE 6-8

Genes which were increased in expression in the MSC
cells as compared to the other cell lines assayed.
Genes Increased In MSC Cells interleukin 26
maltase-glucoamylase (alpha-glucosidase)
nuclear receptor subfamily 4, group A, member 2
v-fos FBJ murine osteosarcoma viral oncogene homolog
hypothetical protein DC42
nuclear receptor subfamily 4, group A, member 2
FBJ murine osteosarcoma viral oncogene homolog B
WNT1 inducible signaling pathway protein 1
MCF.2 cell line derived transforming sequence
potassium channel, subfamily K, member 15
cartilage paired-class homeoprotein 1
*Homo sapiens* cDNA FLJ12232 fis, clone MAMMA1001206
*Homo sapiens* cDNA FLJ34668 fis, clone LIVER2000775
jun B proto-oncogene
B-cell CLL/lymphoma 6 (zinc finger protein 51)
zinc finger protein 36, C3H type, homolog (mouse)

Summary

The present study was performed to provide a molecular characterization of the postpartum cells derived from umbilical cord and placenta. This analysis included cells derived from three different umbilical cords and three different placentas. The study also included two different lines of dermal fibroblasts, three lines of mesenchymal stem cells, and three lines of ileac crest bone marrow cells. The mRNA that was expressed by these cells was analyzed on an GENECHIP oligonucleotide array that contained oligonucleotide probes for 22,000 genes.

The analysis revealed that transcripts for 290 genes were present in different amounts in these five different cell types. These genes include ten genes that are specifically increased in the placenta-derived cells and seven genes specifically increased in the umbilical cord-derived cells. Fifty-four genes were found to have specifically lower expression levels in placenta and umbilical cord.

The expression of selected genes has been confirmed by PCR (see Example 7). These results demonstrate that the postpartum-derived cells have a distinct gene expression profile, for example, as compared to bone marrow-derived cells and fibroblasts.

Example 7

Cell Markers in Postpartum-Derived Cells

Summary

To examine cells derived from the human placenta and the human umbilical cord, their gene expression profiles were compared to those of cells derived from other sources using the Affymetrix GENECHIP. Through this technique we identified 6 genes that were highly expressed in postpartum cells: oxidized LDL receptor 1, interleukin-8, renin, reticulon, chemokine receptor ligand 3 (CXC ligand 3) and granulocyte chemotactic protein 2 (GCP-2). Four of these genes (oxidized LDL receptor 1, renin, reticulon and IL-8) were differentially regulated at the mRNA level in postpartum cells. IL-8 was found to also be differentially regulated at the protein level.

We also investigated the expression of vimentin and alpha-smooth muscle actin, which has previously been associated with stroma-derived cells. Immediately after isolation (passage 0), cells derived from the human placenta stained positive for both alpha-smooth muscle actin and vimentin. This pattern was also observed in cells at passage 11. The result suggests that vimentin and alpha-smooth muscle actin expression in cells is preserved with passaging in the Growth Medium.

Cells derived from the human umbilical cord at passage 0 were probed for the expression of vimentin and alpha-smooth muscle actin proteins and were positive for alpha-smooth muscle actin and vimentin with the potential staining pattern preservation through passage 11.

The mRNA data at least partially verify the data obtained from the microarray experiments.

Introduction

Similarities and differences in cells derived from the human placenta and the human umbilical cord were assessed by comparing their gene expression profiles with those of cells derived from other sources (using an Affymetrix GENECHIP). Six "signature" genes were identified: oxidized LDL receptor 1, interleukin-8, renin, reticulon, chemokine receptor ligand 3 (CXC ligand 3), and granulocyte chemotactic protein 2 (GCP-2). These "signature" genes were expressed at relatively high levels in postpartum-derived cells.

The present studies were conducted to verify the microarray data and determine correlations between gene and protein expression, as well as to establish a series of reliable assays for detection of unique identifiers for placenta- and umbilical cord-derived cells.

Methods & Materials

Cells

Placenta-derived cells (three isolates, including one isolate predominately neonatal as identified by karyotyping analysis), umbilical cord-derived cells (four isolates), and Normal Human Dermal Fibroblasts (NHDF; neonatal and adult) grown in Growth Medium in gelatin-coated T75 flasks. Mesenchymal Stem Cells (MSCs) were grown in Mesenchymal Stem Cell Growth Medium Bullet kit (MSCGM; Cambrex, Walkerville, Md.).

For IL-8 experiment, cells were thawed from liquid nitrogen and plated in gelatin-coated flasks at 5,000 cells/cm$^2$, grown for 48 hours in Growth Medium and then grown for further 8 hours in 10 milliliters of serum starvation medium [DMEM—low glucose (Gibco, Carlsbad, Calif.), penicillin/streptomycin (Gibco, Carlsbad, Calif.) and 0.1% (w/v) Bovine Serum Albumin (BSA; Sigma, St. Louis, Mo.)]. After this treatment RNA was extracted and the supernatants were centrifuged at 150×g for 5 minutes to remove cellular debris. Supernatants were then frozen at −80° C. for ELISA analysis.

Cell Culture for ELISA Assay.

Postpartum cells derived from placenta and umbilical cord, as well as human fibroblasts derived from human neonatal foreskin were cultured in Growth Medium in gelatin-coated T75 flasks. Cells were frozen at passage 11 in liquid nitrogen. Cells were thawed and transferred to 15 ml centrifuge tubes. After centrifugation at 150×g for 5 minutes, the supernatant was discarded. Cells were resuspended in 4 ml culture medium and counted. Cells were grown in a 75 cm² flask containing 15 ml of Growth Medium at 375,000 cells/flask for 24 hours. The medium was changed to a serum starvation medium for 8 hours. Serum starvation medium was collected at the end of incubation, centrifuged at 14,000×g for 5 minutes (and stored at −20° C.).

To estimate the number of cells in each flask, 2 milliliters of tyrpsin/EDTA (Gibco, Carlsbad, Calif.) was added each flask. After cells detached from the flask, trypsin activity was neutralized with 8 milliliters of Growth Medium. Cells were transferred to a 15 milliliters centrifuge tube and centrifuged at 150×g for 5 minutes. Supernatant was removed and 1 milliliter Growth Medium was added to each tube to resuspend the cells. Cell number was estimated using a hemocytometer.

ELISA Assay

The amount of IL-8 secreted by the cells into serum starvation medium was analyzed using ELISA assays (R&D Systems, Minneapolis, Minn.). All assays were tested according to the instructions provided by the manufacture.

Total RNA Isolation

RNA was extracted from confluent postpartum-derived cells and fibroblasts or for IL-8 expression from cells treated as described above. Cells were lysed with 350 microliters buffer RLT containing beta-mercaptoethanol (Sigma, St. Louis, Mo.) according to the manufacturer's instructions (RNeasy Mini Kit; Qiagen, Valencia, Calif.). RNA was extracted according to the manufacturer's instructions (RNeasy Mini Kit; Qiagen, Valencia, Calif.) and subjected to DNase treatment (2.7 U/sample) (Sigma St. Louis, Mo.). RNA was eluted with 50 microliters DEPC-treated water and stored at −80° C.

Reverse Transcription

RNA was also extracted from human placenta and umbilical cord. Tissue (30 mg) was suspended in 700 microliters of buffer RLT containing beta-mercaptoethanol. Samples were mechanically homogenized and the RNA extraction proceeded according to manufacturer's specification. RNA was extracted with 50 microliters of DEPC-treated water and stored at −80° C. RNA was reversed transcribed using random hexamers with the TaqMan® reverse transcription reagents (Applied Biosystems, Foster City, Calif.) at 25° C. for 10 minutes, 37° C. for 60 minutes, and 95° C. for 10 minutes. Samples were stored at −20° C.

Genes identified by cDNA microarray as uniquely regulated in postpartum cells (signature genes—including oxidized LDL receptor, interleukin-8, renin and reticulon), were further investigated using real-time and conventional PCR.

Real-Time PCR

PCR was performed on cDNA samples using Assays-on-Demand™ gene expression products: oxidized LDL receptor (Hs00234028); renin (Hs00166915); reticulon (Hs00382515); CXC ligand 3 (Hs00171061); GCP-2 (Hs00605742); IL-8 (Hs00174103); and GAPDH (Applied Biosystems, Foster City, Calif.) were mixed with cDNA and TaqMan® Universal PCR master mix according to the manufacturer's instructions (Applied Biosystems, Foster City, Calif.) using a 7000 sequence detection system with ABI Prism 7000 SDS software (Applied Biosystems, Foster City, Calif.). Thermal cycle conditions were initially 50° C. for 2 minutes and 95° C. for 10 min, followed by 40 cycles of 95° C. for 15 seconds and 60° C. for 1 minute. PCR data were analyzed according to manufacturer's specifications (User Bulletin #2 from Applied Biosystems for ABI Prism 7700 Sequence Detection System).

Conventional PCR

Conventional PCR was performed using an ABI PRISM 7700 (Perkin Elmer Applied Biosystems, Boston, Mass., USA) to confirm the results from real-time PCR. PCR was performed using 2 microliters of cDNA solution, 1× Ampli-Taq Gold universal mix PCR reaction buffer (Applied Biosystems, Foster City, Calif.) and initial denaturation at 94° C. for 5 minutes. Amplification was optimized for each primer set. For IL-8, CXC ligand 3, and reticulon (94° C. for 15 seconds, 55° C. for 15 seconds and 72° C. for 30 seconds for 30 cycles); for renin (94° C. for 15 seconds, 53° C. for 15 seconds and 72° C. for 30 seconds for 38 cycles); for oxidized LDL receptor and GAPDH (94° C. for 15 seconds, 55° C. for 15 seconds and 72° C. for 30 seconds for 33 cycles). Primers used for amplification are listed in Table 7-1. Primer concentration in the final PCR reaction was 1 µM except for GAPDH which was 0.5 µM. GAPDH primers were the same as real-time PCR, except that the manufacturer's TaqMan® probe was not added to the final PCR reaction. Samples were run on 2% (w/v) agarose gel and stained with ethidium bromide (Sigma, St. Louis, Mo.). Images were captured using a 667 Universal Twinpack film (VWR International, South Plainfield, N.J.) using a focal-length Polaroid™ camera (VWR International, South Plainfield, N.J.).

TABLE 7-1

Primers used

| Primer name | Primers | |
|---|---|---|
| Oxidized LDL receptor | S: 5'-GAGAAATCCAAAGAGCAAATGG-3' | (SEQ ID NO: 1) |
| | A: 5'-AGAATGGAAAACTGGAATAGG-3' | (SEQ ID NO: 2) |
| Renin | S: 5'-TCTTCGATGCTTCGGATTCC-3' | (SEQ ID NO: 3) |
| | A: 5'-GAATTCTCGGAATCTCTGTTG-3' | (SEQ ID NO: 4) |
| Reticulon | S: 5'-TTACAAGCAGTGCAGAAAACC-3' | (SEQ ID NO: 5) |
| | A: 5'-AGTAAACATTGAAACCACAGCC-3' | (SEQ ID NO: 6) |

TABLE 7-1-continued

Primers used

| Primer name | Primers | |
|---|---|---|
| Interleukin-8 | S: 5'-TCTGCAGCTCTGTGTGAAGG-3' | (SEQ ID NO: 7) |
| | A: 5'-CTTCAAAAACTTCTCCACAACC-3' | (SEQ ID NO: 8) |
| Chemokine (CXC) ligand 3 | S: 5'-CCCACGCCACGCTCTCC-3' | (SEQ ID NO: 9) |
| | A: 5'-TCCTGTCAGTTGGTGCTCC-3' | (SEQ ID NO: 10) |

Immunofluorescence

Postpartum cells were fixed with cold 4% (w/v) paraformaldehyde (Sigma-Aldrich, St. Louis, Mo.) for 10 minutes at room temperature. One isolate each of umbilical- and placental-derived cells at passage 0 (P0) (directly after isolation) and passage 11 (P11) (two isolates of Placenta-derived, two isolates of Umbilical cord-derived cells) and fibroblasts (P11) were used. Immunocytochemistry was performed using antibodies directed against the following epitopes: vimentin (1:500, Sigma, St. Louis, Mo.), desmin (1:150; Sigma—raised against rabbit; or 1:300; Chemicon, Temecula, Calif.—raised against mouse), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested on passage 11 postpartum cells: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGA-A (1:100; Santa Cruz, Biotech).

Cultures were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma, St. Louis, Mo.) for 30 minutes to access intracellular antigens. Where the epitope of interest was located on the cell surface (CD34, ox-LDL R1), Triton X-100 was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout. Primary antibodies, diluted in blocking solution, were then applied to the cultures for a period of 1 hour at room temperature. The primary antibody solutions were removed and the cultures were washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150, Santa Cruz Biotech). Cultures were then washed and 10 µM DAPI (Molecular Probes) applied for 10 minutes to visualize cell nuclei.

Following immunostaining, fluorescence was visualized using an appropriate fluorescence filter on an Olympus inverted epi-fluorescent microscope (Olympus, Melville, N.Y.). In all cases, positive staining represented fluorescence signal above control staining where the entire procedure outlined above was followed with the exception of application of a primary antibody solution (no 1° control). Representative images were captured using a digital color videocamera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Preparation of Cells for FACS Analysis

Adherent cells in flasks were washed in phosphate buffered saline (PBS) (Gibco, Carlsbad, Calif.) and detached with Trypsin/EDTA (Gibco, Carlsbad, Calif.). Cells were harvested, centrifuged, and re-suspended 3% (v/v) FBS in PBS at a cell concentration of $1 \times 10^7$ per milliliter. One hundred microliter aliquots were delivered to conical tubes. Cells stained for intracellular antigens were permeablized with Perm/Wash buffer (BD Pharmingen, San Diego, Calif.). Antibody was added to aliquots as per manufactures specifications and the cells were incubated for in the dark for 30 minutes at 4° C. After incubation, cells were washed with PBS and centrifuged to remove excess antibody. Cells requiring a secondary antibody were resuspended in 100 microliters of 3% FBS. Secondary antibody was added as per manufactures specification and the cells were incubated in the dark for 30 minutes at 4° C. After incubation, cells were washed with PBS and centrifuged to remove excess secondary antibody. Washed cells were resuspended in 0.5 milliliters PBS and analyzed by flow cytometry. The following antibodies were used: oxidized LDL receptor 1 (sc-5813; Santa Cruz, Biotech), GROa (555042; BD Pharmingen, Bedford, Mass.), Mouse IgG1 kappa, (P-4685 and M-5284; Sigma), Donkey against Goat IgG (sc-3743; Santa Cruz, Biotech.).

FACS Analysis

Flow cytometry analysis was performed with FACScalibur (Becton Dickinson San Jose, Calif.).

Results

Results of real-time PCR for selected "signature" genes performed on cDNA from cells derived from human placentas, adult and neonatal fibroblasts and Mesenchymal Stem Cells (MSCs) indicate that both oxidized LDL receptor and renin were expressed at higher level in the placenta-derived cells as compared to other cells. The data obtained from real-time PCR were analyzed by the $\Delta \Delta CT$ method and expressed on a logarithmic scale. Levels of reticulon and oxidized LDL receptor expression were higher in umbilical cord-derived cells as compared to other cells. No significant difference in the expression levels of CXC ligand 3 and GCP-2 were found between postpartum cells and controls. The results of real-time PCR were confirmed by conventional PCR. Sequencing of PCR products further validated these observations. No significant difference in the expression level of CXC ligand 3 was found between postpartum cells and controls using conventional PCR CXC ligand 3 primers listed in Table 7-1.

The expression of the cytokine, IL-8 in postpartum cells is elevated in both Growth Medium-cultured and serum-starved postpartum-derived cells. All real-time PCR data were validated with conventional PCR and by sequencing PCR products.

When supernatants of cells grown in serum-free medium were examined for the presence of IL-8, the highest amounts were detected in media derived from umbilical cells and some isolates of placenta cells (Table 7-2). No IL-8 was detected in medium derived from human dermal fibroblasts.

TABLE 7-2

IL-8 protein expression measured by ELISA

| Cell type | IL-8 |
|---|---|
| hFibro | ND |
| Placenta Isolate 1 | ND |
| UMBC Isolate 1 | 2058.42 ± 144.67 |
| Placenta Isolate 2 | ND |
| UMBC Isolate 2 | 2368.86 ± 22.73 |
| Placenta Isolate 3 (normal $O_2$) | 17.27 ± 8.63 |
| Placenta Isolate 3 (low$O_2$, W/O BME) | 264.92 ± 9.88 |

Results of the ELISA assay for interleukin-8 (IL-8) performed on placenta- and umbilical cord-derived cells as well as human skin fibroblasts. Values are presented here are pg/million cells, n = 2, sem.
ND: Not Detected Placenta-derived cells were also examined for the expression of oxidized LDL receptor, GCP-2 and GROalpha by FACS analysis. Cells tested positive for GCP-2. Oxidized LDL receptor and GRO were not detected by this method.

Placental cells were also tested for the expression of selected proteins by immunocytochemical analysis. Immediately after isolation (passage 0), cells derived from the human placenta were fixed with 4% paraformaldehyde and exposed to antibodies for six proteins: von Willebrand Factor, CD34, cytokeratin 18, desmin, alpha-smooth muscle actin, and vimentin. Cells stained positive for both alpha-smooth muscle actin and vimentin. This pattern was preserved through passage 11. Only a few cells (<5%) at passage 0 stained positive for cytokeratin 18.

Cells derived from the human umbilical cord at passage 0 were probed for the expression of selected proteins by immunocytochemical analysis. Immediately after isolation (passage 0), cells were fixed with 4% paraformaldehyde and exposed to antibodies for six proteins: von Willebrand Factor, CD34, cytokeratin 18, desmin, alpha-smooth muscle actin, and vimentin. Umbilical cord-derived cells were positive for alpha-smooth muscle actin and vimentin, with the staining pattern consistent through passage 11.

Placenta-derived and umbilical cord-derived cells at passage 11 were also investigated by immunocytochemistry for the expression of GROalpha, GCP-2, oxidized LDL receptor 1 and reticulon. Complete results of that experiment are still pending.

Discussion and Conclusion

Thus far concordance between gene expression levels measured by microarray and PCR (both real-time and conventional) has been established for four genes: oxidized LDL receptor 1, renin, reticulon, and IL-8. The expression of these genes was differentially regulated at the mRNA level in postpartum cells, with IL-8 also differentially regulated at the protein level. The presence of oxidized LDL receptor was not detected at the protein level by FACS analysis in cells derived from the placenta. Differential expression of GCP-2 and CXC ligand 3 was not confirmed at the mRNA level, however GCP-2 was detected at the protein level by FACS analysis in the placenta-derived cells. Differences between these data and that obtained from the microarray experiment may be due to differences in the sensitivity of the methodologies.

Immediately after isolation (passage 0), cells derived from the human placenta stained positive for both alpha-smooth muscle actin and vimentin. This pattern was also observed in cells at passage 11. These results suggest that vimentin and alpha-smooth muscle actin expression may be preserved in cells with passaging, at least in the Growth Medium used here.

Cells derived from the human umbilical cord at passage 0 were probed for the expression of alpha-smooth muscle actin and vimentin, and were positive for both. The staining pattern was preserved through passage 11.

In conclusion, the complete mRNA data at least partially verify the data obtained from the microarray experiments. As additional protein experiments are complete, the relationships between mRNA and protein expression will be more comprehensively understood.

Example 8

Immunohistochemical Characterization of PPDC Phenotype

The phenotypes of cells found within human postpartum tissues, namely umbilical cord and placenta, were analyzed by immunohistochemistry.

Materials & Methods

Tissue Preparation.

Human umbilical cord and placenta tissue was harvested and immersion fixed in 4% (w/v) paraformaldehyde overnight at 4° C. Immunohistochemistry was performed using antibodies directed against the following epitopes (see Table 8-1): vimentin (1:500; Sigma, St. Louis, Mo.), desmin (1:150, raised against rabbit; Sigma; or 1:300, raised against mouse; Chemicon, Temecula, Calif.), alpha-smooth muscle actin (SMA; 1:400; Sigma), cytokeratin 18 (CK18; 1:400; Sigma), von Willebrand Factor (vWF; 1:200; Sigma), and CD34 (human CD34 Class III; 1:100; DAKOCytomation, Carpinteria, Calif.). In addition, the following markers were tested: anti-human GROalpha-PE (1:100; Becton Dickinson, Franklin Lakes, N.J.), anti-human GCP-2 (1:100; Santa Cruz Biotech, Santa Cruz, Calif.), anti-human oxidized LDL receptor 1 (ox-LDL R1; 1:100; Santa Cruz Biotech), and anti-human NOGO-A (1:100; Santa Cruz Biotech). Fixed specimens were trimmed with a scalpel and placed within OCT embedding compound (Tissue-Tek OCT; Sakura, Torrance, Calif.) on a dry ice bath containing ethanol. Frozen blocks were then sectioned (10 μm thick) using a standard cryostat (Leica Microsystems) and mounted onto glass slides for staining.

TABLE 8-1

Summary of Primary Antibodies Used

| Antibody | Concentration | Vendor |
|---|---|---|
| Vimentin | 1:500 | Sigma, St. Louis, MO |
| Desmin (rb) | 1:150 | Sigma |
| Desmin (m) | 1:300 | Chemicon, Temecula, CA |
| alpha smooth muscle actin (SMA) | 1:400 | Sigma |
| Cytokeratin 18 (CK18) | 1:400 | Sigma |
| von Willebrand factor (vWF) | 1:200 | Sigma |
| CD34 III | 1:100 | DakoCytomation, Carpinteria, CA |
| GROalpha - PE | 1:100 | BD, Franklin Lakes, NJ |
| GCP-2 | 1:100 | Santa Cruz Biotech |
| Ox-LDL R1 | 1:100 | Santa Cruz Biotech |
| NOGO-A | 1:100 | Santa Cruz Biotech |

Immunohistochemistry.

Immunohistochemistry was performed similar to previous studies (e.g., Messina, et al. (2003) *Exper. Neurol.* 184: 816-829). Tissue sections were washed with phosphate-buffered saline (PBS) and exposed to a protein blocking solution containing PBS, 4% (v/v) goat serum (Chemicon, Temecula, Calif.), and 0.3% (v/v) Triton (Triton X-100; Sigma) for 1 hour to access intracellular antigens. In instances where the epitope of interest would be located on the cell surface (CD34, ox-LDL R1), Triton was omitted in all steps of the procedure in order to prevent epitope loss. Furthermore, in instances where the primary antibody was raised against goat (GCP-2, ox-LDL R1, NOGO-A), 3% (v/v) donkey serum was used in place of goat serum throughout the procedure. Primary antibodies, diluted in blocking solution, were then applied to the sections for a period of 4 hours at room temperature. Primary antibody solutions were removed, and cultures washed with PBS prior to application of secondary antibody solutions (1 hour at room temperature) containing block along with goat anti-mouse IgG-Texas Red (1:250; Molecular Probes, Eugene, Oreg.) and/or goat anti-rabbit IgG-Alexa 488 (1:250; Molecular Probes) or donkey anti-goat IgG-FITC (1:150; Santa Cruz Biotech). Cultures were washed, and 10 µM DAPI (Molecular Probes) was applied for 10 minutes to visualize cell nuclei.

Following immunostaining, fluorescence was visualized using the appropriate fluorescence filter on an Olympus inverted epi-fluorescent microscope (Olympus, Melville, N.Y.). Positive staining was represented by fluorescence signal above control staining. Representative images were captured using a digital color video camera and ImagePro software (Media Cybernetics, Carlsbad, Calif.). For triple-stained samples, each image was taken using only one emission filter at a time. Layered montages were then prepared using Adobe Photoshop software (Adobe, San Jose, Calif.).

Results

Umbilical Cord Characterization.

Vimentin, desmin, SMA, CK18, vWF, and CD34 markers were expressed in a subset of the cells found within umbilical cord. In particular, vWF and CD34 expression were restricted to blood vessels contained within the cord. CD34+ cells were on the innermost layer (lumen side). Vimentin expression was found throughout the matrix and blood vessels of the cord. SMA was limited to the matrix and outer walls of the artery & vein, but not contained with the vessels themselves. CK18 and desmin were observed within the vessels only, desmin being restricted to the middle and outer layers.

Placenta Characterization.

Vimentin, desmin, SMA, CK18, vWF, and CD34 were all observed within the placenta and regionally specific.

GROalpha, GCP-2, ox-LDL R1, and NOGO-A Tissue Expression.

None of these markers were observed within umbilical cord or placental tissue.

Summary

Vimentin, desmin, alpha-smooth muscle actin, cytokeratin 18, von Willebrand Factor, and CD34 are expressed in cells within human umbilical cord and placenta.

Example 9

Secretion of Trophic Factors by Postpartum Cells Derived From Placenta and Umbilical Cord The secretion of selected trophic factors from placenta- and umbilical cord-derived PPDCs was measured. Factors were selected that have angiogenic activity (i.e., hepatocyte growth factor (HGF) (Rosen et al. (1997) *Ciba Found. Symp.* 212:215-26), monocyte chemotactic protein 1 (MCP-1) (Salcedo et al. (2000) *Blood* 96; 34-40), interleukin-8 (IL-8) (L1 et al. (2003) *J. Immunol.* 170:3369-76), keratinocyte growth factor (KGF), basic fibroblast growth factor (bFGF), vascular endothelial growth factor (VEGF) (Hughes et al. (2004) *Ann. Thorac. Surg.* 77:812-8), matrix metalloproteinase 1 (TIMP1), angiopoietin 2 (ANG2), platelet derived growth factor (PDGF-bb), thrombopoietin (TPO), heparin-binding epidermal growth factor (HB-EGF), stromal-derived factor 1 alpha (SDF-1 alpha)), neurotrophic/neuroprotective activity (brain-derived neurotrophic factor (BDNF) (Cheng et al. (2003) *Dev. Biol.* 258; 319-33), interleukin-6 (IL-6), granulocyte chemotactic protein-2 (GCP-2), transforming growth factor beta2 (TGFbeta2)), or chemokine activity (macrophage inflammatory protein 1 alpha (MIP1a), macrophage inflammatory protein 1beta (MIP1b), monocyte chemoattractant-1 (MCP-1), Rantes (regulated on activation, normal T cell expressed and secreted), I309, thymus and activation-regulated chemokine (TARC), Eotaxin, macrophage-derived chemokine (MDC), IL-8).

Methods & Materials

Cell Culture.

PPDCs derived from placenta and umbilical cord as well as human fibroblasts derived from human neonatal foreskin were cultured in Growth Medium on gelatin-coated T75 flasks. Cells were cryopreserved at passage 11 and stored in liquid nitrogen. After thawing of the cells, Growth Medium was added to the cells followed by transfer to a 15 milliliters centrifuge tube and centrifugation of the cells at 150×g for 5 minutes. The supernatant was discarded. The cell pellet was resuspended in 4 milliliters Growth Medium, and cells were counted. Cells were seeded at 375,000 cells/75 cm$^2$ flask containing 15 milliliters of Growth Medium and cultured for 24 hours. The medium was changed to a serum-free medium (DMEM-low glucose (Gibco), 0.1% (w/v) bovine serum albumin (Sigma), penicillin/streptomycin (Gibco)) for 8 hours. Conditioned serum-free media was collected at the end of incubation by centrifugation at 14,000×g for 5 minutes and stored at −20° C. To estimate the number of cells in each flask, cells were washed with phosphate-buffered saline (PBS) and detached using 2 milliliters trypsin/EDTA (Gibco). Trypsin activity was inhibited by addition of 8 milliliters Growth Medium. Cells were centrifuged at 150×g for 5 minutes. Supernatant was removed, and cells were resuspended in 1 milliliter Growth Medium. Cell number was estimated using a hemocytometer.

ELISA Assay.

Cells were grown at 37° C. in 5% carbon dioxide and atmospheric oxygen. Placenta-derived PPDCs (101503) also were grown in 5% oxygen or beta-mercaptoethanol (BME). The amount of MCP-1, IL-6, VEGF, SDF-1alpha, GCP-2, IL-8, and TGF-beta2 produced by each cell sample was measured by an ELISA assay (R&D Systems, Minneapolis, Minn.). All assays were performed according to the manufacturer's instructions. Values presented are pg/ml/million cells (n=2, sem).

SearchLight® Multiplexed ELISA Assay.

Chemokines (MIP1a, MIP1b, MCP-1, Rantes, I309, TARC, Eotaxin, MDC, IL8), BDNF, and angiogenic factors (HGF, KGF, bFGF, VEGF, TIMP1, ANG2, PDGF-bb, TPO, HB-EGF were measured using SearchLight® Proteome Arrays (Pierce Biotechnology Inc.). The Proteome Arrays are multiplexed sandwich ELISAs for the quantitative measurement of two to 16 proteins per well. The arrays are produced by spotting a 2×2, 3×3, or 4×4 pattern of four to 16 different capture antibodies into each well of a 96-well plate. Following a sandwich ELISA procedure, the entire plate is imaged to capture chemiluminescent signal generated at each spot within each well of the plate. The amount of signal generated in each spot is proportional to the amount of target protein in the standard or sample.

Results

ELISA Assay.

MCP-1 and IL-6 were secreted by placenta- and umbilical cord-derived PPDCs and dermal fibroblasts (Table 9-1). SDF-1alpha was secreted by placenta-derived PPDCs cultured in 5% $O_2$ and by fibroblasts. GCP-2 and IL-8 were secreted by umbilical-derived PPDCs and by placenta-derived PPDCs cultured in the presence of BME or 5% $O_2$. GCP-2 also was secreted by human fibroblasts. TGF-beta2 was not detectable by ELISA assay.

TABLE 9-1

ELISA assay results

|  | MCP-1 | IL-6 | VEGF | SDF-1α | GCP-2 | IL-8 | TGF-β2 |
|---|---|---|---|---|---|---|---|
| Fibroblast | 17 ± 1 | 61 ± 3 | 29 ± 2 | 19 ± 1 | 21 ± 1 | ND | ND |
| Placenta (042303) | 60 ± 3 | 41 ± 2 | ND | ND | ND | ND | ND |
| Umbilical (022803) | 1150 ± 74 | 4234 ± 289 | ND | ND | 160 ± 11 | 2058 ± 145 | ND |
| Placenta (071003) | 125 ± 16 | 10 ± 1 | ND | ND | ND | ND | ND |
| Umbilical (071003) | 2794 ± 84 | 1356 ± 43 | ND | ND | 2184 ± 98 | 2369 ± 23 | ND |
| Placenta (101503) BME | 21 ± 10 | 67 ± 3 | ND | ND | 44 ± 9 | 17 ± 9 | ND |
| Placenta (101503) 5% $O_2$, W/O BME | 77 ± 16 | 339 ± 21 | ND | 1149 ± 137 | 54 ± 2 | 265 ± 10 | ND |

Key: ND: Not Detected.

SearchLight® Multiplexed ELISA Assay.

TIMP1, TPO, KGF, HGF, FGF, HBEGF, BDNF, MIP1b, MCP1, RANTES, I309, TARC, MDC, and IL-8 were secreted from umbilical cord-derived PPDCs (Tables 9-2 and 9-3). TIMP1, TPO, KGF, HGF, HBEGF, BDNF, MIP1a, MCP-1, RANTES, TARC, Eotaxin, and IL-8 were secreted from placenta-derived PPDCs (Tables 9-2 and 9-3). No Ang2, VEGF, or PDGF-bb were detected.

TABLE 9-2

SearchLight ® Multiplexed ELISA assay results

|  | TIMP1 | ANG2 | PDGFbb | TPO | KGF | HGF | FGF | VEGF | HBEGF | BDNF |
|---|---|---|---|---|---|---|---|---|---|---|
| hFB | 19306.3 | ND | ND | 230.5 | 5.0 | ND | ND | 27.9 | 1.3 | ND |
| P1 | 24299.5 | ND | ND | 546.6 | 8.8 | 16.4 | ND | ND | 3.81.3 | ND |
| U1 | 57718.4 | ND | ND | 1240.0 | 5.8 | 559.3 | 148.7 | ND | 9.3 | 165.7 |
| P3 | 14176.8 | ND | ND | 568.7 | 5.2 | 10.2 | ND | ND | 1.9 | 33.6 |
| U3 | 21850.0 | ND | ND | 1134.5 | 9.0 | 195.6 | 30.8 | ND | 5.4 | 388.6 |

Key: hFB (human fibroblasts), P1 (placenta-derived PPDC (042303)), U1 (umbilical cord-derived PPDC (022803)), P3 (placenta-derived PPDC (071003)), U3 (umbilical cord-derived PPDC (071003)). ND: Not Detected.

TABLE 9-3

SearchLight ® Multiplexed ELISA assay results

|  | MIP1a | MIP1b | MCP1 | RANTES | I309 | TARC | Eotaxin | MDC | IL8 |
|---|---|---|---|---|---|---|---|---|---|
| hFB | ND | ND | 39.6 | ND | ND | 0.1 | ND | ND | 204.9 |
| P1 | 79.5 | ND | 228.4 | 4.1 | ND | 3.8 | 12.2 | ND | 413.5 |
| U1 | ND | 8.0 | 1694.2 | ND | 22.4 | 37.6 | ND | 18.9 | 51930.1 |
| P3 | ND | ND | 102.7 | ND | ND | 0.4 | ND | ND | 63.8 |
| U3 | ND | 5.2 | 2018.7 | 41.5 | 11.6 | 21.4 | ND | 4.8 | 10515.9 |

Key: hFB (human fibroblasts), P1 (placenta-derived PPDC (042303)), U1 (umbilical cord-derived PPDC (022803)), P3 (placenta-derived PPDC (071003)), U3 (umbilical cord-derived PPDC (071003)). ND: Not Detected.

Summary

Umbilical cord- and placenta-derived cells secreted a number of trophic factors. Some of these trophic factors, such as HGF, bFGF, MCP-1 and IL-8, play important roles in angiogenesis. Other trophic factors, such as BDNF and IL-6, have important roles in neural regeneration.

Example 10

In Vitro Immunology

Postpartum cell lines were evaluated in vitro for their immunological characteristics in an effort to predict the immunological response, if any, these cells would elicit upon in vivo transplantation. Postpartum cell lines were assayed by flow cytometry for the expression of HLA-DR, HLA-DP, HLA-DQ, CD80, CD86, and B7-H2. These proteins are expressed by antigen-presenting cells (APC) and are required for the direct stimulation of naïve $CD4^+$ T cells (Abbas & Lichtman, CELLULAR AND MOLECULAR IMMUNOLOGY, 5th Ed. (2003) Saunders, Philadelphia, p. 171). The cell lines were also analyzed by flow cytometry for the expression of HLA-G (Abbas & Lichtman, CELLULAR AND MOLECULAR IMMUNOLOGY, 5th Ed. (2003) Saunders, Philadelphia, p. 171), CD178 (Coumans, et. al., (1999) *Journal of Immunological Methods* 224, 185-196), and PD-L2 (Abbas & Lichtman, CELLULAR AND MOLECULAR IMMUNOLOGY, 5th Ed. (2003) Saunders, Philadelphia, p. 171; Brown, et. al. (2003) *The Journal of Immunology* 170, 1257-1266). The expression of these proteins by cells residing in placental tissues is thought to mediate the immuno-privileged status of placental tissues in utero. To predict the extent to which postpartum placenta- and umbilical cord-derived cell lines elicit an immune response in vivo, the cell lines were tested in a one-way mixed lymphocyte reaction (MLR).

Materials and Methods
Cell Culture.

Cells were cultured in Growth Media until confluent in T75 flasks (Corning, Corning, N.Y.) coated with 2% gelatin (Sigma, St. Louis, Mo.).

Antibody Staining.

Cells were washed in phosphate buffered saline (PBS) (Gibco, Carlsbad, Calif.) and detached with Trypsin/EDTA (Gibco, Carlsbad, Mo.). Cells were harvested, centrifuged, and re-suspended in 3% (v/v) FBS in PBS at a cell concentration of $1\times10^7$ per milliliter. Antibody (Table 10-1) was added to one hundred microliters of cell suspension as per manufacturer's specifications and incubated in the dark for 30 minutes at 4° C. After incubation, cells were washed with PBS and centrifuged to remove unbound antibody. Cells were re-suspended in five hundred microliters of PBS and analyzed by flow cytometry using a FACSCalibur instrument (Becton Dickinson, San Jose, Calif.).

TABLE 10-1

| Antibodies | | |
|---|---|---|
| Antibody | Manufacture | Catalog Number |
| HLA-DRDPDQ | BD Pharmingen (San Diego, CA) | 555558 |
| CD80 | BD Pharmingen (San Diego, CA) | 557227 |
| CD86 | BD Pharmingen (San Diego, CA) | 555665 |
| B7-H2 | BD Pharmingen (San Diego, CA) | 552502 |
| HLA-G | Abcam (Cambridgeshire, UK) | ab 7904-100 |
| CD178 | Santa Cruz (San Cruz, CA) | sc-19681 |
| PD-L2 | BD Pharmingen (San Diego, CA) | 557846 |
| Mouse IgG2a | Sigma (St. Louis, MO) | F-6522 |
| Mouse IgG1kappa | Sigma (St. Louis, MO) | P-4685 |

Mixed Lymphocyte Reaction.

Cryopreserved vials of passage 10 umbilical cord-derived PPDCs labeled as cell line A and passage 11 placenta-derived PPDCs labeled as cell line B were sent on dry ice to CTBR (Senneville, Quebec) to conduct a mixed lymphocyte reaction using CTBR SOP no. CAC-031. Peripheral blood mononuclear cells (PBMCs) were collected from multiple male and female volunteer donors. Stimulator (donor) allogeneic PBMC, autologous PBMC, and postpartum cell lines were treated with mitomycin C. Autologous and mitomycin C-treated stimulator cells were added to responder (recipient) PBMCs and cultured for 4 days. After incubation, $[^3H]$thymidine was added to each sample and cultured for 18 hours. Following harvest of the cells, radiolabeled DNA was extracted, and $[^3H]$-thymidine incorporation was measured using a scintillation counter.

The stimulation index for the allogeneic donor (SIAD) was calculated as the mean proliferation of the receiver plus mitomycin C-treated allogeneic donor divided by the baseline proliferation of the receiver. The stimulation index of the postpartum cell was calculated as the mean proliferation of the receiver plus mitomycin C-treated postpartum cell line divided by the baseline proliferation of the receiver.

Results

Mixed Lymphocyte Reaction-Placenta.

Seven human volunteer blood donors were screened to identify a single allogeneic donor that would exhibit a robust proliferation response in a mixed lymphocyte reaction with the other six blood donors. This donor was selected as the allogeneic positive control donor. The remaining six blood donors were selected as recipients. The allogeneic positive control donor and placenta cell lines were treated with mitomycin C and cultured in a mixed lymphocyte reaction with the six individual allogeneic receivers. Reactions were performed in triplicate using two cell culture plates with three receivers per plate (Table 10-2). The average stimulation index ranged from 1.3 (plate 2) to 3 (plate 1) and the allogeneic donor positive controls ranged from 46.25 (plate 2) to 279 (plate 1) (Table 10-3).

TABLE 10-2

Mixed Lymphocyte Reaction Data - Cell Line B (Placenta)
DPM for Proliferation Assay

| Analytical number | Culture System | Replicates | | | Mean | SD | CV |
|---|---|---|---|---|---|---|---|
| | | 1 | 2 | 3 | | | |
| Plate ID: Plate 1 | | | | | | | |
| IM03-7769 | Proliferation baseline of receiver | 79 | 119 | 138 | 112.0 | 30.12 | 26.9 |
| | Control of autostimulation (Mitomycin C treated autologous cells) | 241 | 272 | 175 | 229.3 | 49.54 | 21.6 |
| | MLR allogenic donor IM03-7768 (Mitomycin C treated) | 23971 | 22352 | 20921 | 22414.7 | 1525.97 | 6.8 |
| | MLR with cell line (Mitomycin C treated cell type B) | 664 | 559 | 1090 | 771.0 | 281.21 | 36.5 |
| SI (donor) | | | | | 200 | | |
| SI (cell line) | | | | | 7 | | |

TABLE 10-2-continued

Mixed Lymphocyte Reaction Data - Cell Line B (Placenta)
DPM for Proliferation Assay

| Analytical number | Culture System | Replicates | | | Mean | SD | CV |
|---|---|---|---|---|---|---|---|
| | | 1 | 2 | 3 | | | |
| IM03-7770 | Proliferation baseline of receiver | 206 | 134 | 262 | 200.7 | 64.17 | 32.0 |
| | Control of autostimulation (Mitomycin C treated autologous cells) | 1091 | 602 | 524 | 739.0 | 307.33 | 41.6 |
| | MLR allogenic donor IM03-7768 (Mitomycin C treated) | 45005 | 43729 | 44071 | 44268.3 | 660.49 | 1.5 |
| | MLR with cell line (Mitomycin C treated cell type B) | 533 | 2582 | 2376 | 1830.3 | 1128.24 | 61.6 |
| SI (donor) | | | | | 221 | | |
| SI (cell line) | | | | | 9 | | |
| IM03-7771 | Proliferation baseline of receiver | 157 | 87 | 128 | 124.0 | 35.17 | 28.4 |
| | Control of autostimulation (Mitomycin C treated autologous cells) | 293 | 138 | 508 | 313.0 | 185.81 | 59.4 |
| | MLR allogenic donor IM03-7768 (Mitomycin C treated) | 24497 | 34348 | 31388 | 30077.7 | 5054.53 | 16.8 |
| | MLR with cell line (Mitomycin C treated cell type B) | 601 | 643 | a | 622.0 | 29.70 | 4.8 |
| SI (donor) | | | | | 243 | | |
| SI (cell line) | | | | | 5 | | |
| IM03-7772 | Proliferation baseline of receiver | 56 | 98 | 51 | 68.3 | 25.81 | 37.8 |
| | Control of autostimulation (Mitomycin C treated autologous cells) | 133 | 120 | 213 | 155.3 | 50.36 | 32.4 |
| | MLR allogenic donor IM03-7768 (Mitomycin C treated) | 14222 | 20076 | 22168 | 18822.0 | 4118.75 | 21.9 |
| | MLR with cell line (Mitomycin C treated cell type B) | a | a | a | a | a | a |
| SI (donor) | | | | | 275 | | |
| SI (cell line) | | | | | a | | |
| IM03-7768 (allogenic donor) | Proliferation baseline of receiver | 84 | 242 | 208 | 178.0 | 83.16 | 46.7 |
| | Control of autostimulation (Mitomycin treated autologous cells) | 361 | 617 | 304 | 427.3 | 166.71 | 39.0 |
| Cell line type B | Proliferation baseline of receiver | 126 | 124 | 143 | 131.0 | 10.44 | 8.0 |
| | Control of autostimulation (Mitomycin treated autologous cells) | 822 | 1075 | 487 | 794.7 | 294.95 | 37.1 |
| Plate ID: Plate 2 | | | | | | | |
| IM03-7773 | Proliferation baseline of receiver | 908 | 181 | 330 | 473.0 | 384.02 | 81.2 |
| | Control of autostimulation (Mitomycin C treated autologous cells) | 269 | 405 | 572 | 415.3 | 151.76 | 36.5 |
| | MLR allogenic donor IM03-7768 (Mitomycin C treated) | 29151 | 28691 | 28315 | 28719.0 | 418.70 | 1.5 |
| | MLR with cell line (Mitomycin C treated cell type B) | 567 | 732 | 905 | 734.7 | 169.02 | 23.0 |
| SI (donor) | | | | | 61 | | |
| SI (cell line) | | | | | 2 | | |
| IM03-7774 | Proliferation baseline of receiver | 893 | 1376 | 185 | 818.0 | 599.03 | 73.2 |
| | Control of autostimulation (Mitomycin C treated autologous cells) | 261 | 381 | 568 | 403.3 | 154.71 | 38.4 |
| | MLR allogenic donor IM03-7768 (Mitomycin C treated) | 53101 | 42839 | 48283 | 48074.3 | 5134.18 | 10.7 |
| | MLR with cell line (Mitomycin C treated cell type B) | 515 | 789 | 294 | 532.7 | 247.97 | 46.6 |
| SI (donor) | | | | | 59 | | |
| SI (cell line) | | | | | 1 | | |
| IM03-7775 | Proliferation baseline of receiver | 1272 | 300 | 544 | 705.3 | 505.69 | 71.7 |
| | Control of autostimulation (Mitomycin C treated autologous cells) | 232 | 199 | 484 | 305.0 | 155.89 | 51.1 |
| | MLR allogenic donor IM03-7768 (Mitomycin C treated) | 23554 | 10523 | 28965 | 21014.0 | 9479.74 | 45.1 |
| | MLR with cell line (Mitomycin C treated cell type B) | 768 | 924 | 563 | 751.7 | 181.05 | 24.1 |
| SI (donor) | | | | | 30 | | |
| SI (cell line) | | | | | 1 | | |
| IM03-7776 | Proliferation baseline of receiver | 1530 | 137 | 1046 | 904.3 | 707.22 | 78.2 |
| | Control of autostimulation (Mitomycin C treated autologous cells) | 420 | 218 | 394 | 344.0 | 109.89 | 31.9 |
| | MLR allogenic donor IM03-7768 (Mitomycin C treated) | 28893 | 32493 | 34746 | 32044.0 | 2952.22 | 9.2 |
| | MLR with cell line (Mitomycin C treated cell type B) | a | a | a | a | a | a |
| SI (donor) | | | | | 35 | | |
| SI (cell line) | | | | | a | | |

TABLE 10-3

Average stimulation index of placenta cells and an allogeneic donor in a mixed lymphocyte reaction with six individual allogeneic receivers.

Average Stimulation Index

| | Recipient | Placenta |
|---|---|---|
| Plate 1 (receivers 1-3) | 279 | 3 |
| Plate 2 (receivers 4-6) | 46.25 | 1.3 |

Mixed Lymphocyte Reaction—Umbilicus.

Six human volunteer blood donors were screened to identify a single allogeneic donor that will exhibit a robust proliferation response in a mixed lymphocyte reaction with the other five blood donors. This donor was selected as the allogeneic positive control donor. The remaining five blood donors were selected as recipients. The allogeneic positive control donor and placenta cell lines were mitomycin C-treated and cultured in a mixed lymphocyte reaction with the five individual allogeneic receivers. Reactions were performed in triplicate using two cell culture plates with three receivers per plate (Table 10-4). The average stimulation index ranged from 6.5 (plate 1) to 9 (plate 2) and the allogeneic donor positive controls ranged from 42.75 (plate 1) to 70 (plate 2) (Table 10-5).

TABLE 10-4

Mixed Lymphocyte Reaction Data- Cell Line A (Umbilicus)
DPM for Proliferation Assay

| Analytical number | Culture System | Replicates 1 | 2 | 3 | Mean | SD | CV |
|---|---|---|---|---|---|---|---|
| Plate ID: Plate 1 | | | | | | | |
| IM04-2478 | Proliferation baseline of receiver | 1074 | 406 | 391 | 623.7 | 390.07 | 62.5 |
| | Control of autostimulation (Mitomycin C treated autologous cells) | 672 | 510 | 1402 | 861.3 | 475.19 | 55.2 |
| | MLR allogenic donor IM04-2477 (Mitomycin C treated) | 43777 | 48391 | 38231 | 43466.3 | 5087.12 | 11.7 |
| | MLR with cell line (Mitomycin C treated cell type A) | 2914 | 5622 | 6109 | 4881.7 | 1721.36 | 35.3 |
| SI (donor) | | | | | 70 | | |
| SI (cell line) | | | | | 8 | | |
| IM04-2479 | Proliferation baseline of receiver | 530 | 508 | 527 | 521.7 | 11.93 | 2.3 |
| | Control of autostimulation (Mitomycin C treated autologous cells) | 701 | 567 | 1111 | 793.0 | 283.43 | 35.7 |
| | MLR allogenic donor IM04-2477 (Mitomycin C treated) | 25593 | 24732 | 22707 | 24344.0 | 1481.61 | 6.1 |
| | MLR with cell line (Mitomycin C treated cell type A) | 5086 | 3932 | 1497 | 3505.0 | 1832.21 | 52.3 |
| SI (donor) | | | | | 47 | | |
| SI (cell line) | | | | | 7 | | |
| IM04-2480 | Proliferation baseline of receiver | 1192 | 854 | 1330 | 1125.3 | 244.90 | 21.8 |
| | Control of autostimulation (Mitomycin C treated autologous cells) | 2963 | 993 | 2197 | 2051.0 | 993.08 | 48.4 |
| | MLR allogenic donor IM04-2477 (Mitomycin C treated) | 25416 | 29721 | 23757 | 26298.0 | 3078.27 | 11.7 |
| | MLR with cell line (Mitomycin C treated cell type A) | 2596 | 5076 | 3426 | 3699.3 | 1262.39 | 34.1 |
| SI (donor) | | | | | 23 | | |
| SI (cell line) | | | | | 3 | | |
| IM04-2481 | Proliferation baseline of receiver | 695 | 451 | 555 | 567.0 | 122.44 | 21.6 |
| | Control of autostimulation (Mitomycin C treated autologous cells) | 738 | 1252 | 464 | 818.0 | 400.04 | 48.9 |
| | MLR allogenic donor IM04-2477 (Mitomycin C treated) | 13177 | 24885 | 15444 | 17835.3 | 6209.52 | 34.8 |
| | MLR with cell line (Mitomycin C treated cell type A) | 4495 | 3671 | 4674 | 4280.0 | 534.95 | 12.5 |
| SI (donor) | | | | | 31 | | |
| SI (cell line) | | | | | 8 | | |
| Plate ID: Plate 2 | | | | | | | |
| IM04-2482 | Proliferation baseline of receiver | 432 | 533 | 274 | 413.0 | 130.54 | 31.6 |
| | Control of autostimulation (Mitomycin C treated autologous cells) | 1459 | 633 | 598 | 896.7 | 487.31 | 54.3 |
| | MLR allogenic donor IM04-2477 (Mitomycin C treated) | 24286 | 30823 | 31346 | 28818.3 | 3933.82 | 13.7 |
| | MLR with cell line (Mitomycin C treated cell type A) | 2762 | 1502 | 6723 | 3662.3 | 2724.46 | 74.4 |
| SI (donor) | | | | | 70 | | |
| SI (cell line) | | | | | 9 | | |
| IM04-2477 (allogenic donor) Cell line type A | Proliferation baseline of receiver | 312 | 419 | 349 | 360.0 | 54.34 | 15.1 |
| | Control of autostimulation (Mitomycin treated autologous cells) | 567 | 604 | 374 | 515.0 | 123.50 | 24.0 |
| | Proliferation baseline of receiver | 5101 | 3735 | 2973 | 3936.3 | 1078.19 | 27.4 |
| | Control of autostimulation (Mitomycin treated autologous cells) | 1924 | 4570 | 2153 | 2882.3 | 1466.04 | 50.9 |

TABLE 10-5

Average stimulation index of umbilical cells and an allogeneic donor in a mixed lymphocyte reaction with five individual allogeneic receivers.
Average Stimulation Index

| | Recipient | Umbilicus |
|---|---|---|
| Plate 1 (receivers 1-4) | 42.75 | 6.5 |
| Plate 2 (receiver 5) | 70 | 9 |

Antigen Presenting Cell Markers—Placenta.

Histograms of placenta cells analyzed by flow cytometry show negative expression of HLA-DR, DP, DQ, CD80, CD86, and B7-H2, as noted by fluorescence value consistent with the IgG control, indicating that placental cell lines lack the cell surface molecules required to directly stimulate CD4$^+$ T cells.

Immuno-Modulating Markers—Placenta.

Histograms of placenta cells analyzed by flow cytometry show positive expression of PD-L2, as noted by the increased value of fluorescence relative to the IgG control, and negative expression of CD178 and HLA-G, as noted by fluorescence value consistent with the IgG control.

Antigen Presenting Cell Markers—Umbilicus.

Histograms of umbilical cells analyzed by flow cytometry show negative expression of HLA-DR, DP, DQ, CD80, CD86, and B7-H2, as noted by fluorescence value consistent with the IgG control, indicating that umbilical cell lines lack the cell surface molecules required to directly stimulate CD4$^+$ T cells.

Immuno-Modulating Markers—Umbilicus.

Histograms of umbilical cells analyzed by flow cytometry show positive expression of PD-L2, as noted by the increased value of fluorescence relative to the IgG control, and negative expression of CD178 and HLA-G, as noted by fluorescence value consistent with the IgG control.

Summary

In the mixed lymphocyte reactions conducted with placental cell lines, the average stimulation index ranged from 1.3 to 3, and that of the allogeneic positive controls ranged from 46.25 to 279. In the mixed lymphocyte reactions conducted with umbilical cell lines the average stimulation index ranged from 6.5 to 9, and that of the allogeneic positive controls ranged from 42.75 to 70. Placental and umbilical cell lines were negative for the expression of the stimulating proteins HLA-DR, HLA-DP, HLA-DQ, CD80, CD86, and B7-H2, as measured by flow cytometry. Placental and umbilical cell lines were negative for the expression of immuno-modulating proteins HLA-G and CD 178 and positive for the expression of PD-L2, as measured by flow cytometry. Allogeneic donor PBMCs contain antigen-presenting cells expressing HLA-DR, DP, DQ, CD80, CD86, and B7-H2, thereby allowing for the stimulation of naïve CD4+ T cells. The absence of antigen-presenting cell surface molecules on placenta- and umbilical cord-derived cells required for the direct stimulation of naïve CD4+ T cells and the presence of PD-L2, an immuno-modulating protein, may account for the low stimulation index exhibited by these cells in a MLR as compared to allogeneic controls.

Example 11

Plasma Clotting Assay

Cell therapy may be injected systemically for certain applications where cells are able to target the site of action. It is important that injected cells not cause thrombosis, which may be fatal. Tissue factor, a membrane-bound procoagulant glycoprotein, is the initiator of the extrinsic clotting cascade, which is the predominant coagulation pathway in vivo. Tissue factor also plays an important role in embryonic vessel formation, for example, in the formation of the primitive vascular wall (Brodsky et al. (2002) *Exp. Nephrol.* 10:299-306). To determine the potential for PPDCs to initiate clotting, umbilical cord and placenta-derived PPDCs were evaluated for tissue factor expression and their ability to initiate plasma clotting.

Methods & Materials

Human Tissue Factor.

SIMPLASTIN, a human tissue factor (Organon Tekailca Corporation, Durham, N.C.), was reconstituted with 20 milliliters distilled water. The stock solution was serially diluted (1:2) in eight tubes. Normal human plasma (George King Bio-Medical, Overland Park, Kans.) was thawed at 37° C. in a water bath and then stored in ice before use. To each well of a 96-well plate was added 100 microliters phosphate buffered saline (PBS), 10 microliters diluted SIMPLASTIN (except a blank well), 30 microliters 0.1M calcium chloride, and 100 microliters of normal human plasma. The plate was immediately placed in a temperature-controlled microplate reader and absorbance measured at 405 nanometers at 40 second intervals for 30 minutes.

J-82 and Postpartum Cells.

J-82 cells (ATCC, MD) were grown in Iscove's modified Dulbecco's medium (IMDM; Gibco, Carlsbad, Calif.) containing 10% (v/v) fetal bovine serum (FBS; Hyclone, Logan Utah), 1 millimolar sodium pyruvate (Sigma Chemical, St. Louis, Mo.), 2 millimolar L-Glutamine (Mediatech Herndon, Va.), 1× non-essential amino acids (Mediatech Herndon, Va.). At 70% confluence, cells were transferred to wells of 96-well plate at 100,000, 50,000 and 25,000 cells/well. Postpartum cells derived from placenta and umbilical cord were cultured in Growth Medium in gelatin-coated T75 flasks (Corning, Corning, N.Y.). Placenta-derived cells at passage 5 and umbilical cord-derived cells at passages 5 and 18 were transferred to wells at 50,000 cells/well. Culture medium was removed from each well after centrifugation at 150×g for 5 minutes. Cells were suspended in PBS without calcium and magnesium. Cells incubated with anti-tissue factor antibody cells were incubated with 20 micrograms/milliliter CNTO 859 (Centocor, Malvern, Pa.) for 30 minutes. Calcium chloride (30 microliters) was added to each well. The plate was immediately placed in a temperature-controlled microplate reader and absorbance measured at 405 nanometers at 40 second intervals for 30 minutes.

Antibody Staining.

Cells were washed in PBS and detached from the flask with Trypsin/EDTA (Gibco Carlsbad, Calif.). Cells were harvested, centrifuged, and re-suspended 3% (v/v) FBS in PBS at a cell concentration of $1\times10^7$ per milliliter. Antibody was added to 100 microliters cell suspension as per the manufacturer's specifications, and the cells were incubated in the dark for 30 minutes at 4° C. After incubation, cells were washed with PBS and centrifuged at 150×g for 5 minutes to remove unbound antibody. Cells were re-suspended in 100 microliters of 3% FBS and secondary antibody added as per the manufacturer's instructions. Cells were incubated in the dark for 30 minutes at 4° C. After incubation, cells were washed with PBS and centrifuged to remove unbound secondary antibody. Washed cells were re-suspended in 500 microliters of PBS and analyzed by flow cytometry.

Flow Cytometry Analysis.

Flow cytometry analysis was performed with a FACSCalibur instrument (Becton Dickinson, San Jose, Calif.).

Results

Flow cytometry analysis revealed that both placenta- and umbilical cord-derived postpartum cells express tissue factor. A plasma clotting assay demonstrated that tissue factor was active. Both placenta- and umbilical cord-derived cells increased the clotting rate as indicated by the time to half maximal absorbance (T ½ to max; Table 11-1). Clotting was observed with both early (P5) and late (P18) cells. The T ½ to max is inversely proportional to the number of J82 cells. Preincubation of umbilical cells with CNTO 859, an antibody to tissue factor, inhibited the clotting reaction, thereby showing that tissue factor was responsible for the clotting.

TABLE 11-1

The effect of human tissue factor (SIMPLASTIN), placenta-derived cells (Pla), and umbilical cord-derived cells (Umb) on plasma clotting was evaluated. The time to half maximal absorbance (T ½ to max) at the plateau in seconds was used as a measurement unit.

| SIMPLASTIN Dilution | T ½ to max (seconds) |
|---|---|
| 1:2 | 61 |
| 1:4 | 107 |
| 1:8 | 147 |
| 1:16 | 174 |
| 1:32 | 266 |
| 1:64 | 317 |
| 1:128 | 378 |
| 0 (negative control) | 1188 |
| J-82 cells | |
| 100,000 | 122 |
| 50,000 | 172 |
| 25,000 | 275 |
| Pla P5 | |
| 50,000 | 757 |
| Umb P5 | |
| 50,000 | 833 |
| Umb P18 | |
| 50,000 | 443 |

Summary

Placenta- and umbilical cord-derived PPDCs express tissue factor. The addition of an antibody to tissue factor can inhibit tissue factor. Tissue factor is normally found on cells in a conformation that is inactive but is activated by mechanical or chemical (e.g., LPS) stress (Sakariassen et al. (2001) *Thromb. Res.* 104:149-74; Engstad et al. (2002) *Int. Immunopharmacol.* 2:1585-97). Thus, minimization of stress during the preparation process of PPDCs may prevent activation of tissue factor. In addition to the thrombogenic activity, tissue factor has been associated with angiogenic activity. Thus, tissue factor activity may be beneficial when umbilical cord- or placenta-derived PPDCs are transplanted in tissue but should be inhibited when PPDCs are injected intravenously.

FIG. 11-1.

Plasma clotting with J82 cells and umbilical cells without (A) and with (B) CNTO 859, anti-human tissue factor, 20 μg/milliliters. Antibody treatment showed that coagulation was due to tissue factor on umbilical cells.

Example 12

Differentiation of Postpartum Cells to the Cardiomyocyte Phenotype

There is a tremendous need for therapy that will slow the progression of and/or cure heart disease, such as ischemic heart disease and congestive heart failure. Cells that can differentiate into cardiomyocytes that can fully integrate into the patient's cardiac muscle without arrhythmias is highly desirable. Rodent mesenchymal stem cells treated with 5-azacytidine have been shown to express markers of cardiomyocytes (Fukuda et al. (2002) *C. R. Biol.* 325:1027-38). The same has not been shown for adult human stem cells. Additional factors have been used to improve stem cell differentiation including low oxygen (Storch (1990) *Biochim. Biophys. Acta* 1055: 126-9), retinoic acid (Wobus et al. (1997) *J. Mol. Cell Cardiol.* 29:1525-39), DMSO (Xu et al. (2002) *Circ. Res.* 91:501-8), and chelerythrine chloride (International PCT Publication No. WO03/025149), which effects the translocation of PKC from the cytosol to plasma membrane and is an inhibitor of PKC activity. In the present study, PPDCs (P10) were treated with 5-azacytidine either alone or in combination with DMSO or chelerythrine chloride and markers of cardiomyocytes measured by real-time PCR.

Methods & Materials

Cells.

Cryopreserved umbilical cord-derived cells (P10) and placenta-derived cells (P24) were grown in Growth Medium in gelatin-coated flasks. Cells were seeded at $5\times10^4$ cells/well in 96-well plates in Growth Medium for 24 hours. The medium was changed to 0, 3, 10 and 30 μM 5-azacytidine (Sigma, St. Louis, Mo.) alone or with 5 μM chelerythrine chloride (Sigma), 1% (v/v) dimethylsulfoxide (DMSO) (Sigma), or 1 μM retinoic acid (Sigma) in MEM-alpha (Sigma), insulin, transferrin, and selenium (ITS; Sigma), 10% (v/v) fetal bovine serum, penicillin and streptomycin, and cells incubated at 37° C., 5% (v/v) $O_2$ for 48 or 72 hours. Media was then changed to MEM-alpha, insulin, transferrin, and selenium, 10% (v/v) fetal bovine serum, penicillin and streptomycin, and cells incubated at 37° C., 5% (v/v) $O_2$ for 14 days.

RNA Extraction and Reverse Transcription.

Cells were lysed with 150 microliters buffer RLT containing beta-mercaptoethanol (Sigma St. Louis, Mo.) according to the manufacturer's instructions (RNeasy 96 kit, Qiagen, Valencia, Calif.) and stored at −80° C. Cell lysates were thawed and RNA extracted according to the manufacturer's instructions (RNeasy 96 kit, Qiagen, Valencia, Calif.) with a 2.7 U/sample DNase treatment (Sigma St. Louis, Mo.). RNA was eluted with 50 microliters DEPC-treated water and stored at −80° C. RNA was reverse transcribed using random hexamers with the TaqMan® reverse transcription reagents (Applied Biosystems, Foster City, Calif.) at 25° C. for 10 minutes, 37° C. for 60 minutes and 95° C. for 10 minutes. Samples were stored at −20° C.

PCR.

PCR was performed on cDNA samples using Assays-on-Demand™ gene expression products cardiac myosin (Hs00165276 ml), skeletal myosin (Hs00428600), GATA 4 (Hs00171403 ml), GAPDH (Applied Biosystems, Foster City, Calif.), and TaqMan® Universal PCR master mix according to the manufacturer's instructions (Applied Biosystems, Foster City, Calif.) using a 7000 sequence detection system with ABI prism 7000 SDS software (Applied Biosystems, Foster City, Calif.). Thermal cycle conditions were initially 50° C. for 2 minutes and 95° C. for 10 minutes followed by 40 cycles of 95° C. for 15 seconds and 60° C. for 1 minute. cDNA from heart and skeletal muscle (Ambion Austin Tex.) were used as a control.

Results

Analysis of RNA from cardiac muscle showed expression of cardiac myosin and GATA 4. Skeletal muscle RNA analysis showed expression skeletal myosin and cardiac myosin but not of GATA 4. Placenta-derived cells (P24) treated for 72 h with factors and grown for a further 14 days expressed GATA 4, but no skeletal myosin or cardiac myosin. Umbilical cord-derived cells (P12) treated for 48 h with factors and cultured for a further 14 days expressed low levels of GATA 4, but no skeletal myosin or cardiac myosin. Additional samples from placenta and umbilical cord cells that were analyzed showed expression of GATA 4 under the conditions tested.

Summary

Untreated placenta- and umbilical cord-derived cells constitutively express GATA 4, a nuclear transcription factor in cardiomyocytes, sertoli cells, and hepatocytes.

Example 13

Assessment of Postpartum Cell-Based Cardiovascular Therapy in a Rodent Coronary Ligation Model Animal models of heart failure have increased our understanding of the pathophysiology of the disease and have assisted in the development of new treatments for congestive heart failure (CHF). Coronary artery occlusion, or the blocking of the vessels that supply the heart tissue, in the rat closely mimics the pathophysiology of acute myocardial infarction in humans and has been used successfully to study pharmacological interventions for CHF. Transplantation of human cells into cardiac lesions is a potential viable therapeutic treatment for CHF.

The objective of this study was to determine the efficacy of intracardiac human cell treatment when administered 15 minutes post-coronary artery occlusion in a rodent model of myocardial ischemia/infarction.

Methods & Materials

The Charles River Worcester, Mass. test facility is accredited by the Association for the Assessment and Accreditation of Laboratory Animal Care, International (AAALAC) and registered with the United States Department of Agriculture to conduct research in laboratory animals. All the conditions of testing conform to the Animal Welfare Act (9 CFR) and its amendments. The protocol was reviewed and approved by the Institutional Animal Care and Use Committee (IACUC) at the Test Facility for compliance with regulations prior to study initiation.

The animals having characteristics identified in Table 13-1 were individually housed in micro-isolator cages on autoclaved bedding. The cages conform to standards set forth in The Guide for the Care and Use of Laboratory Animals.

TABLE 13-1

Animal characteristics

| Species: | *Rattus norvegicus* |
|---|---|
| Strain: | Rnu |
| Source: | Charles River Laboratories |
| Age at Dosing: | 6-8 weeks |
| Weight at Dosing: | ~200-250 g |
| Number of Males (including spares): | 40 + 10 |

Purina Certified Diet (irradiated) was provided to the animals ad libitum. This diet was routinely analyzed by the manufacturer for nutritional components and environmental contaminants. Results of the manufacturer's analyses are on file at the Test Facility.

Autoclaved Filtered tap water was provided ad libitum. Samples of the filtered water were analyzed for total dissolved solids, hardness, specified microbiological content, and selected environmental contaminants. Results of these analyses are on file at the Test Facility.

Environmental controls were set to maintain temperatures of 18 to 26° C. (64 to 79° F.) with a relative humidity of 30% to 70%. A 12:12 hour light:dark cycle was maintained. Ten or greater air changes per hour were maintained in the animal rooms. Upon receipt and prior to use on the study, the animals were held for a minimum of four days for conditioning according to the Test Facility Vendor Management Program as described in the Test Facility Standard Operating Procedure, Receipt, Conditioning, and Quarantine of Laboratory Animals.

Each animal was identified by a unique number and this number was indicated by an ear punch. Animals were randomly assigned to groups by a weight-ordered distribution such that individual body weights did not exceed ±20% of mean weight.

The animals were anesthetized with sodium pentobarbital (40 milligrams/kilogram) and buprenorphine (0.05 milligrams/kilogram) as a single cocktail given intramuscularly (IM). Following the establishment of anesthesia, animals were intubated using an 18-16 gauge, 2-inch length angiocath, or appropriate sized angiocath, and maintained on room air respiration (supplemented with oxygen) and a positive pressure ventilator throughout the surgical procedure. Additional anesthesia was given incrementally as needed. Preoperative antibiotic therapy was also administered, Benzathine/Procaine penicillin G, 40,000 Units/kilogram, IM. Additional antibiotic therapy was administered every 48 hours.

Electrode pads were placed around the appropriate paws of the animals to receive a useable ECG signal. Animals were positioned on a heating pad to help maintain body temperature throughout the procedure. A rectal temperature probe was inserted into the animal to monitor body temperature. Ophthalmic ointment was administered to each eye. The surgical sites (thoracic area) were prepared for aseptic surgery by removing any excess fur, and gently wiping the area with sponges that have been soaked in 70% isopropyl alcohol, which was allowed to dry. Medi Sepps™ or similar solution was then applied to the area and also allowed to dry. The area was appropriately draped for strict aseptic surgery.

A surgical incision was made on the skin over the fourth intercostal space. Blunt dissection through the muscle layers was used to access the thoracic cavity. A retractor was carefully inserted into the fourth intercostal space and opened to allow access to the interior cavity. The pericardium was carefully opened via gentle teasing with cotton swabs dampened in sterile saline solution. A damp cotton swab was used to gently push the apex of the heart into the opening where a length of 6-0 silk suture was attached into the myocardium for manipulation of the heart. After a pause to allow the heart to recover, the suture placed in the apex was used to ease the heart out of the chest cavity and to place sufficient tension on the heart to allow access to the upper heart and the left anterior descending coronary artery (LAD). Another length of 6-0 silk suture was placed into the myocardium so as to surround the LAD. The pressure on the apical suture was released and the heart allowed to return to the interior of the chest cavity.

Once the heart rate and ECG returned to baseline values, the ligatures around the LAD were tied off to occlude the LAD. This was a permanent occlusion with the suture tied off and the ends trimmed. Once the ligature was tied, the surgeon looked for the following indications of successful occlusion: change in color of the area of the heart directly below the ligature to a white/grayish white as a result of the termination of blood flow to the area and a significant change in the ECG corresponding to occlusion of the LAD. Arrhythmias may have developed within the first 10 minutes of the occlusion. The rat was monitored closely during this time period in the event that resuscitation was necessary. In the event of severe arrhythmia and failure of the rat to convert to normal sinus rhythm without assistance, aid was rendered via cardiac massage. Approximately 15 minutes following the initiation of the LAD occlusion, the area of left ventricle made ischemic was treated with either vehicle or test article by direct injection into the ischemic myocardium. Treatment consisted of three to ten intramyocardial injections (100 microliters/injection) into the ischemic zone of myocardium.

Human cells were grown in Growth Medium in gelatin-coated T300 flasks. Cells were washed with phosphate buffered saline (PBS, Gibco, Carlsbad Calif.) and trypsinized using Trypsin/EDTA (Gibco, Carlsbad Calif.). The trypsinization was stopped by adding Growth Medium. The cells were centrifuged at 150×g, supernatant removed, and the cell pellet was resuspended in approximately 1 milliliter Growth Medium per million cells. An aliquot of cells was removed and added to trypan blue (Sigma, St. Louis, Mo.). The viable cell number was estimated using a hemocytometer. The cell suspension was centrifuged and resuspended in 1 milliliters Growth containing 10% (v/v) DMSO (Hybrimax, Sigma, St. Louis, Mo.) per 5 million cells and transferred into Cryovials (Nalgene). The cells were cooled at approximately 1° C./min overnight in a −80° C. freezer using a "Mr Frosty" freezing container (Nalgene, Rochester, N.Y.). Vials of cells were transferred into liquid nitrogen. Vials were shipped from CBAT, Somerville, N.J. to Charles River, Worcester, Mass. on dry ice and stored at −80° C. Approximately 1-2 hours before injection of cells into the animal, a vial of cells was thawed rapidly in a 37° C. water bath. Under aseptic conditions in a BSL2 biosafety cabinet, cells were added to 40 milliliters PBS with magnesium and calcium (Sigma St. Louis, Mo.) and centrifuged at 150×g for 5 minutes before resuspending the cell pellet in 10 milliliters PBS. The cell number and viability was estimated as described above. The cells were centrifuged at 150×g for 5 minutes and resuspended in PBS at a final concentration of $10^6$ viable cells/100 microliters. The cell suspension was loaded into 1 milliliter syringes with a 30 G needle and kept on ice. Viability was assessed again up to 5 hours on ice.

Following the administration of treatment (Table 13-2) and stabilization of the heart, the surgeon began closing the surgical incision. The retractor was removed. The lungs were over-inflated for 3-4 breaths and visually inspected as much as possible to ensure that they were fully re-inflated. This created a negative pressure necessary to prevent pneumothorax post-recovery. To evacuate fluid and excess air from the thoracic cavity after closing the cavity, an intravenous catheter (i.e., 20 gauge, 2 mm in length) was placed through the skin and muscle layers so that the tip remains in the thoracic cavity. Care was taken so that the tip did not pierce the lung or heart. The separated ribs and associated muscle was sutured together with appropriate suture. The upper layers of muscle was sutured using a simple continuous pattern. The skin was closed with 4-0 silk using a horizontal mattress pattern. A 10 milliliter syringe was attached to the intravenous catheter that had been previously placed in the thoracic cavity and the plunger slowly pulled back to withdraw fluids and air from the cavity. At the same time, the catheter was slowly withdrawn from the entry site, thereby allowing the surrounding muscle mass and skin to seal the puncture. The surgical drape was removed and fluids (i.e., lactated Ringers solution, 25 milliliters/kilogram subcutaneously [SC] or intraperitoneally [IP]) were given.

Immediately after each rat had undergone treatment with test article and the incision sutured, the animal underwent an echocardiography (ECG) examination. Anesthesia was maintained throughout the completion of the echo examination. Upon the completion of the echo examination, ventilation was discontinued, and the rat was returned to the recovery area to recover in a heated, oxygenated recovery cage.

A second echo examination of each surviving animal was completed at the end of the study (approximately 28 days post-treatment), prior to termination. During the second examination, the animals were anesthetized as described previously.

For each echo examination, the left thoracic area was shaved, and warmed, ultrasonic gel was applied to the skin to enhance contact with the transducer. Electrode pads were placed around the appropriate extremities to receive an ECG signal. Echocardiographic images included short axis and long axis views to allow for the determination of ventricular cavity dimensions, contractility, blood flow through vasculature, and wall thickness. These images were saved on optical disk for further analysis. After examination, the gel medium was removed from the skin with gauze or paper towel. The rat was removed from the ventilator and placed in a warmed recovery cage until mobile.

At the conclusion of the surgical procedures, respiratory ventilation was turned off. The animals were observed for pedal reflex. The rectal probe and ECG electrodes subsequently were removed, and the animal was extubated and placed in a warmed oxygenated recovery cage. After complete recovery from anesthesia, the animals were given buprenorphine (0.05 milligrams/kilogram, SC). Observations were made regularly until the animals showed full mobility and an interest in food and water. The animals then were placed in a clean housing cage and returned to the animal housing room. Animals were monitored for surgical incision integrity twice daily post-surgery.

Analgesics (i.e., Buprenorphine, 0.05 milligrams/kilogram SC.) were given twice daily for 4 days post-operatively and thereafter as needed. Visual indications of post-operative pain include lack of normal body postures and movement (e.g., animal remains in hunched position), antipathy, lack of eating/drinking, lack of grooming, etc.

TABLE 13-2

Treatment regimens

| Gr. No. | No. of Males | Test Article | Dosage Level (cells/animal) | Dose Conc. (cells/milliliters) | Route/Dose Regimen | Time of Treatment Administration | Necropsy Day |
|---|---|---|---|---|---|---|---|
| 1 | 8 | Vehicle | 0 | 0 | Direct injection(s) into the ischemic region of the left ventricle of the heart, consisting of 3 to 10 intramyocardial injections of 100 μL total. | 15 minutes after coronary artery ligation | Day 28 (±1 Day) |
| 2 | 8 | Placenta #4 (P10) (A) | 1 million | 10 million | | | |
| 3 | 8 | Umbilical (P10) (B) | | | | | |
| 4 | 8 | Placenta #3 (P10) (C) | | | | | |
| 5 | 8 | Human fibroblasts 1F1853 (P10) (D) | | | | | |

Gr. = Group; No. = Number; Conc. = Concentration

Body weight was recorded for each animal prior to initial treatment, weekly thereafter, and on the day of necropsy. Animals found dead were weighed and necropsied.

In order for the heart to be harvested, each rat was anesthetized as was done for surgery. The jugular vein was cannulated. The heart was arrested in diastole with KCl infused via the jugular cannula. The heart was then removed from the thoracic cavity. A limited necropsy was then performed on the heart after which the heart was placed in 10% neutral buffered formalin. The remainder of each carcass was then discarded with no further evaluation.

Hearts of all animals that were found dead or euthanized moribund were placed in 4% paraformaldehyde until evaluated. The remainder of each carcass was then discarded with no further evaluation.

Histology and Image Analysis.

Fixed tissues sectioned with a stainless steel coronal heart matrix (Harvard Apparatus Holliston, Mass.) yielded four two-millimeter thick serial tissue sections. Sections were processed and serially embedded in paraffin using routine methods. Five-micron sections were obtained by microtome and stained Masson's Tri-chrome for Connective Tissue (Poly Scientific Bay Shore, N.Y.) using manufacturer's methods. Electronic photomicrographs were captured and analyzed using image analysis methods developed by Phase 3 Imaging System (Glen Mills, Pa.). Photomicrographs of the trichrome stained sections were color-metrically analyzed electronically to determine the overall area of the ventricle and free wall and the area of the differential staining.

Results

There was no loss in the initial viability of cells over 5 hours in the vehicle when kept on ice. Cells were injected into the infarct with one to three needle entry points and multiple changes in direction of needle orientation.

Echocardiography measurements taken from the infarct-treated rats were used to evaluate the results. The left ventricle fractional shortening and the ejection fraction were similarly utilized. These values were calculated as described by Sahn et al. (1978) *Circulation* 58:1072-1083. The fractional shortening of the vehicle-treated animals was significantly decreased from 47.7%±8.3% at Day 0 to 23.5%±30.2% at Day 28 ($p<0.05$). The animals that were treated with postpartum-derived cells showed small, non-significant differences between the fractional shortening between Day 0 and 28. There was no significant difference between the fractional shortening between the groups at Day 0. Each group had eight animals at the start but some did not survive the experiment. The fibroblast-treated animals experienced greater mortality (80%) than the groups treated with PPDCs.

Hearts collected at the study termination were subjected to histological analysis. The hearts were arrested in diastole and fixed. The results were calculated from an algorithm to estimate the percentage of total heart area that comprises the infarct. The infarct size in the vehicle-treated animals was 22.9%±6.7% of heart area, while the infarct size in hearts treated with placenta-derived cells (isolate 1) was 13.9%±3.7%, with umbilical cord cells was 12.5%±2.5%, with placenta-derived cells (isolate 2) was 12.9%±3.4%, and with fibroblasts was 19.3%±8.0%. The difference of infarct size of cell-treated animals relative to vehicle-treated animals was not statistically significant by either Student's t test or ANOVA.

Summary

The results of the present study suggest that the postpartum-derived cells may have some benefit in reducing the damage of a surgically induced myocardial infarction in rats. The vehicle-treated animals showed a significant reduction in cardiac function at day 28 as compared to day 0, as measured by fractional shortening, while the placenta- and umbilical cord-derived cell-treated animals showed minimal change over the 28-day study. The fibroblast-treated animals showed minimal change but only two animals survived the study. Evaluation of infarct size suggested that there may be some modest, but not statistically significant, reduction in the infarct size in the postpartum-derived cell-treated animals as compared to the vehicle controls at Day 28. Taken together, these data establish efficacy of the postpartum-derived cells in reducing damage from myocardial infarction.

Example 14

PPDCs can be Injected as a Matrix-Cell Complex

Cells derived from the postpartum umbilical cord are useful for regenerative therapies. The tissue produced by postpartum-derived cells transplanted into SCID mice with a biodegradable material was evaluated. The materials evaluated were Vicryl non-woven, 35/65 PCL/PGA foam, and RAD 16 self-assembling peptide hydrogel.

Methods & Materials

Cell Culture.

Umbilical cord-derived cells were grown in Growth Medium in gelatin-coated flasks.

Sample Preparation.

One million viable cells were seeded in 15 microliters Growth Medium onto 5 mm diameter, 2.25 mm thick Vicryl non-woven scaffolds (64.33 mg/cc; Lot#3547-47-1) or 5 mm diameter 35/65 PCL/PGA foam (Lot#3415-53). Cells were allowed to attach for two hours before adding more Growth Medium to cover the scaffolds. Cells were grown on scaffolds overnight. Scaffolds without cells were also incubated in medium.

RAD16 self-assembling peptides (3D Matrix, Cambridge, Mass. under a material transfer agreement) was obtained as a sterile 1% (w/v) solution in water, which was mixed 1:1 with $1\times10^6$ cells in 10% (w/v) sucrose (Sigma, St Louis, Mo.), 10 millimolar HEPES in Dulbecco's modified medium (DMEM; Gibco) immediately before use. The final concentration of cells in RAD16 hydrogel was $1\times10^6$ cells/100 microliters.

Test Material (N=4/Rx)
1. Vicryl non-woven+$1\times10^6$ umbilical cord-derived cells
2. 35/65 PCL/PGA foam+$1\times10^6$ umbilical cord-derived cells
3. RAD 16 self-assembling peptide+$1\times10^6$ umbilical cord-derived cells
4. 35/65 PCL/PGA foam
5. Vicryl non-woven Animal Preparation.

The animals utilized in this study were handled and maintained in accordance with the current requirements of the Animal Welfare Act. Compliance with the above Public Laws were accomplished by adhering to the Animal Welfare regulations (9 CFR) and conforming to the current standards promulgated in the Guide for the Care and Use of Laboratory Animals, 7th edition.

Mice (Mus Musculus)/Fox Chase SCID/Male (Harlan Sprague Dawley, Inc., Indianapolis, Ind.), 5 Weeks of Age.

All handling of the SCID mice took place under a hood. The mice were individually weighed and anesthetized with an intraperitoneal injection of a mixture of 60 milligrams/kilogram KETASET (ketamine hydrochloride, Aveco Co., Inc., Fort Dodge, Iowa) and 10 milligrams/kilogram ROMPUN (xylazine, Mobay Corp., Shawnee, Kans.) and saline. After induction of anesthesia, the entire back of the animal from the dorsal cervical area to the dorsal lumbosacral area was clipped free of hair using electric animal clippers. The area was then scrubbed with chlorhexidine diacetate, rinsed with alcohol, dried, and painted with an aqueous iodophor solution of 1% available iodine. Ophthalmic ointment was applied to the eyes to prevent drying of the tissue during the anesthetic period.

Subcutaneous Implantation Technique.

Four skin incisions, each approximately 1.0 cm in length, were made on the dorsum of the mice. Two cranial sites were located transversely over the dorsal lateral thoracic region, about 5-mm caudal to the palpated inferior edge of the scapula, with one to the left and one to the right of the vertebral column. Another two were placed transversely over the gluteal muscle area at the caudal sacro-lumbar level, about 5-mm caudal to the palpated iliac crest, with one on either side of the midline. Implants were randomly placed in these sites. The skin was separated from the underlying connective tissue to make a small pocket and the implant placed (or injected for RAD16) about 1-cm caudal to the incision. The appropriate test material was implanted into the subcutaneous space. The skin incision was closed with metal clips.

Animal Housing.

Mice were individually housed in microisolator cages throughout the course of the study within a temperature range of 64° F.-79° F. and relative humidity of 30% to 70%, and maintained on an approximate 12 hour light/12 hour dark cycle. The temperature and relative humidity were maintained within the stated ranges to the greatest extent possible. Diet consisted of Irradiated Pico Mouse Chow 5058 (Purina Co.) and water fed ad libitum.

Mice were euthanized at their designated intervals by carbon dioxide inhalation. The subcutaneous implantation sites with their overlying skin were excised and frozen for histology.

Histology.

Excised skin with implant was fixed with 10% neutral buffered formalin (Richard-Allan Kalamazoo, Mich.). Samples with overlying and adjacent tissue were centrally bisected, paraffin-processed, and embedded on cut surface using routine methods. Five-micron tissue sections were obtained by microtome and stained with hematoxylin and eosin (Poly Scientific Bay Shore, N.Y.) using routine methods.

Results

There was minimal in growth of tissue into foams implanted subcutaneously in SCID mice after 30 days. In contrast there was extensive tissue fill in foams implanted with umbilical-derived cells.

There was some tissue in growth in Vicryl non-woven scaffolds. Non-woven scaffolds seeded with umbilical cord-derived cells showed increased matrix deposition and mature blood vessels.

Summary

The purpose of this study was to determine the type of tissue formed by cells derived from human umbilical cord in scaffolds in immune deficient mice. Synthetic absorbable non-woven/foam discs (5.0 mm diameter×1.0 mm thick) or self-assembling peptide hydrogel were seeded with cells derived from human umbilical cord and implanted subcutaneously bilaterally in the dorsal spine region of SCID mice. The present study demonstrates that postpartum-derived cells can dramatically increase good quality tissue formation in biodegradable scaffolds.

Example 15

Endothelial Network Formation

PPDCs Promote Angiogenesis In Vitro

Angiogenesis, or the formation of new vasculature, is necessary for the growth of new tissue. Induction of angiogenesis is an important therapeutic goal in many pathological conditions. The present study was aimed at identifying potential angiogenic activity of the postpartum cells in in vitro assays. The study followed a well-established method of seeding endothelial cells onto a culture plate coated with a basement membrane extract (Nicosia and Ottinetti (1990) In Vitro Cell Dev. Biol. 26(2):119-28). Treating endothelial cells on extracellular matrix with angiogenic factors will stimulate the cells to form a network that is similar to capillaries. This is a common in vitro assay for testing stimulators and inhibitors of blood vessel formation (Ito et al. (1996) Int. J. Cancer 67(1):148-52). The present studies made use of a co-culture system with the postpartum cells seeded onto culture well inserts. The permeable inserts allow for the passive exchange of media components between the endothelial and the postpartum culture media.

Material & Methods

Cell Culture.

Postpartum Tissue-Derived Cells.

Human umbilical cords and placenta were received and cells were isolated as previously described (Example 1). Cells were cultured in Growth Medium on gelatin-coated tissue culture plastic flasks. The cultures were incubated at 37° C. with 5% $CO_2$. Cells used for experiments were from about passage 4 to 12.

Actively growing postpartum cells were trypsinized, counted, and seeded onto Costar® Transwell® 6.5 mm diameter tissue culture inserts (Corning, Corning, N.Y.) at 15,000 cells per insert. Cells were cultured on the inserts for 48-72 hours in Growth Medium at 37° C. with 5% $CO_2$.

Human Mesenchymal Stem Cells (hMSC).

hMSCs were purchased from Cambrex (Walkersville, Md.) and cultured in MSCGM (Cambrex). The cultures were incubated at 37° C. with 5% $CO_2$.

Actively growing MSCs were trypsinized, counted and seeded onto Costar® Transwell® 6.5 mm diameter tissue culture inserts (Corning, Corning, N.Y.) at 15,000 cells per insert. Cells were cultured on the inserts for 48-72 hours in Growth Medium at 37° C. with 5% $CO_2$.

Human Umbilical Vein Endothelial Cells. (HUVEC).

HUVEC were obtained from Cambrex (Walkersville, Md.). Cells were grown in separate cultures in either EBM or EGM endothelial cell media (Cambrex). Cells were grown on standard tissue cultured plastic at 37° C. with 5% $CO_2$. Cells used in the assay were from about passage 4 to 10.

Human Coronary Artery Endothelial Cells (HCAEC).

HCAEC were purchased from Cambrex Incorporated (Walkersville, Md.). The cells were maintained in separate cultures in either the EBM or EGM media formulations. Cells were grown on standard tissue culture plastic at 37° C. with 5% $CO_2$. Cells used for experiments were from about passage 4 to 8.

Matrigel™ Assays.

Culture plates were coated with Matrigel™ according to manufacturer's specifications. Briefly, Matrigel™ (BD Discovery Labware, Bedford, Mass.) was thawed at 4° C. and approximately 250 microliters was aliquoted and distributed evenly onto each well of a chilled 24-well culture plate (Corning). The plate was then incubated at 37° C. for 30 minutes to allow the material to solidify. Actively growing endothelial cell cultures were trypsinized and counted. Cells were washed twice in Growth Media with 2% FBS by centrifugation, resuspension, and aspiration of the supernatant. Cells were seeded onto the coated wells 20,000 cells per well in approximately 0.5 milliliters Growth Medium with 2% (v/v) FBS. Cells were then incubated for approximately 30 minutes to allow cells to settle.

Endothelial cell cultures were then treated with either 10 nanomolar human bFGF (Peprotech, Rocky Hill, N.J.) or 10 nanomolar human VEGF (Peprotech, Rocky Hill, N.J.) to serve as a positive control for endothelial cell response. Transwell inserts seeded with postpartum cells were added to appropriate wells with Growth media with 2% FBS in the insert chamber. Cultures were incubated at 37° C. with 5% $CO_2$ for approximately 24 hours. The well plate was removed from the incubator, and images of the endothelial cell cultures were collected with an Olympus inverted microscope (Olympus, Melville, N.Y.).

Results

In a co-culture system with placenta-derived cells or with umbilical cord-derived cells, HUVEC form cell networks. HUVEC cells form limited cell networks in co-culture experiments with hMSC and with 10 nanomolar bFGF. HUVEC cells without any treatment showed very little or no network formation. These results suggest that the postpartum cells release angiogenic factors that stimulate the HUVEC.

In a co-culture system with placenta-derived cells or with umbilical cord-derived cells, CAECs form cell networks.

Table 15-1 shows levels of known angiogenic factors released by the postpartum cells in Growth Medium. Postpartum cells were seeded onto inserts as described above. The cells were cultured at 37° C. in atmospheric oxygen for 48 hours on the inserts and then switched to a 2% FBS media and returned at 37° C. for 24 hours. Media were removed, immediately frozen and stored at −80° C., and analyzed by the SearchLight® multiplex ELISA assay (Pierce Chemical Company, Rockford, Ill.). Results shown are the averages of duplicate measurements. The results show that the postpartum cells do not release detectable levels of platelet-derived growth factor-bb (PDGF-bb) or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF), and vascular endothelial growth factor (VEGF).

TABLE 15-1

Potential angiogenic factors released from postpartum cells.
Postpartum cells were cultured in 24 hours in media with 2% FBS in atmospheric oxygen. Media were removed and assayed by the SearchLight ® multiplex ELISA assay (Pierce). Results are the means of a duplicate analysis. Values are concentrations in the media reported in picograms per milliliter of culture media.

|  | TIMP1 (pg/mL) | ANG2 (pg/mL) | PDGFBB (pg/mL) | TPO (pg/mL) | KGF (pg/mL) | HGF (pg/mL) | FGF (pg/mL) | VEGF (pg/mL) | HBEGF (pg/mL) |
|---|---|---|---|---|---|---|---|---|---|
| Placenta (P4) | 91655.3 | 175.5 | <2.0 | 275.5 | 3.0 | 58.3 | 7.5 | 644.6 | <1.2 |
| Placenta (P11) | 1592832.4 | 28.1 | <2.0 | 1273.1 | 193.3 | 5960.3 | 34.8 | 12361.1 | 1.7 |
| Umbilical cord (P4) | 81831.7 | <9.8 | <2.0 | 365.9 | 14.1 | 200.2 | 5.8 | <4.0 | <1.2 |
| Media alone | <9.8 | 25.1 | <2.0 | <6.4 | <2.0 | <3.2 | <5.4 | <4.0 | <1.2 |

Table 15-2 shows levels of known angiogenic factors released by the postpartum cells. Postpartum cells were seeded onto inserts as described above. The cells were cultured in Growth Medium at 5% oxygen for 48 hours on the inserts and then switched to a 2% FBS medium and returned to 5% $O_2$ incubation for 24 hours. Media were removed, immediately frozen, and stored at −80° C., and analyzed by the SearchLight® multiplex ELISA assay (Pierce Chemical Company, Rockford, Ill.). Results shown are the averages of duplicate measurements. The results show that the postpartum cells do not release detectable levels of platelet-derived growth factor-bb (PDGF-BB), or heparin-binding epidermal growth factor (HBEGF). The cells do release measurable quantities of tissue inhibitor of metallinoprotease-1 (TIMP-1), angiopoietin 2 (ANG2), thrombopoietin (TPO), keratinocyte growth factor (KGF), hepatocyte growth factor (HGF), fibroblast growth factor (FGF) and vascular endothelial growth factor (VEGF).

TABLE 15-2

Potential angiogenic factors released from postpartum cells.
Postpartum cells were cultured in 24 hours in media with 2% FBS in 5% oxygen.
Media were removed and assayed by the SearchLight ® multiplex ELISA assay
(Pierce). Results are the means of a duplicate analysis. Values are concentrations
in the media reported in picograms per milliliter of culture media.

|  | TIMP1 (pg/mL) | ANG2 (pg/mL) | PDGFBB (pg/mL) | TPO (pg/mL) | KGF (pg/mL) | HGF (pg/mL) | FGF (pg/mL) | VEGF (pg/mL) | HBEGF (pg/mL) |
|---|---|---|---|---|---|---|---|---|---|
| Placenta (P4) | 72972.5 | 253.6 | <2.0 | 743.1 | 2.5 | 30.2 | 15.1 | 1495.1 | <1.2 |
| Placenta (P11) | 458023.1 | 55.1 | <2.0 | 2562.2 | 114.2 | 2138.0 | 295.1 | 7521.3 | 1.8 |
| Umbilical cord (P4) | 50244.7 | <9.8 | <2.0 | 403.3 | 10.7 | 156.8 | 5.7 | <4.0 | <1.2 |
| Media alone | <9.8 | 25.1 | <2.0 | <6.4 | <2.0 | <3.2 | <5.4 | <4.0 | <1.2 |

Summary

Postpartum cells can stimulate both human umbilical vein and coronary artery endothelial cells to form networks in an in vitro Matrigel™ assay. This effect is similar to that with known angiogenic factors in this assay system, suggesting that the postpartum cells are useful for stimulating angiogenesis in vivo.

Biological Deposit of Postpartum-Derived Cells and Cultures

Consistent with the detailed description and the written examples provided herein, examples of umbilicus-derived cells of the invention were deposited with the American Type Culture Collection (ATCC, 10801 University Blvd. Manassas, Va. 20110-2209) on Jun. 10, 2004, and assigned ATCC Accession Numbers as follows: (1) strain designation UMB 022803 (P7) was assigned Accession No. PTA-6067; and (2) strain designation UMB 022803 (P17) was assigned Accession No. PTA-6068.

As with the umbilicus-derived cells, examples of placenta-derived cells of the invention were also deposited with the American Type Culture Collection (ATCC, 10801 University Blvd. Manassas, Va. 20110-2209) and assigned ATCC Accession Numbers as follows: (1) strain designation PLA 071003 (P8) was deposited Jun. 15, 2004 and assigned Accession No. PTA-6074; (2) strain designation PLA 071003 (P11) was deposited Jun. 15, 2004 and assigned Accession No. PTA-6075; and (3) strain designation PLA 071003 (P16) was deposited Jun. 16, 2004 and assigned Accession No. PTA-6079.

What is claimed:

1. A method for maintaining cardiac function as measured by fractional shortening following myocardial infarction in a patient, the method comprising
   administering by injection to the ischemic myocardium of the patient a homogeneous population of cells in an amount effective to maintain cardiac function as measured by fractional shortening following myocardial infarction,
   wherein the homogeneous population of cells is isolated from human umbilical cord tissue substantially free of blood, does not express CD31, CD34, CD45, CD80, CD86, CD178, B7-H2, HLA-G, CD117, CD141 and HLA-DR, DP, DQ, does express CD10, CD13, CD44, CD73, CD90 PDGFr-alpha PD-L2 and HLA-A, B, C, has the potential for at least 40 doublings in culture, maintains a normal karyotype upon passaging, has the potential to express GATA4, and has increased expression of an endogenous gene encoding interleukin 8 and an endogenous gene encoding reticulon 1 relative to expression of an endogenous gene encoding interleukin 8 and an endogenous gene encoding reticulon 1 by a human cell that is a fibroblast, a mesenchymal stem cell, or an iliac crest bone marrow cell.

2. The method of claim 1, wherein the homogenous cell population is administered with at least one other agent.

3. The method of claim 2, wherein the at least one other agent is an antithrombogenic agent, an anti-inflammatory agent, an immunosuppressive agent, an immunomodulatory agent, or an antiapoptotic agent.

4. The method of claim 2, wherein the at least one other agent is administered simultaneously with, or before, or after, the cell population.

5. A method for maintaining cardiac function as measured by fractional shortening following myocardial infarction in a patient, the method comprising administering by injection to the ischemic myocardium of the patient a substantially homogeneous population of cells in an amount effective to maintain cardiac function as measured by fractional shortening following myocardial infarction, wherein the cells are isolated from human umbilical cord tissue substantially free of blood and identified by ATCC Accession No. PTA-6067.

6. A method for maintaining cardiac function as measured by fractional shortening following myocardial infarction in a patient, the method comprising administering by injection to the ischemic myocardium of the patient a substantially homogeneous population of cells in an amount effective to maintain cardiac function as measured by fractional shortening following myocardial infarction, wherein the cells are isolated from human umbilical cord tissue substantially free of blood and identified by ATCC Accession No. PTA-6068.

* * * * *

UNITED STATES PATENT AND TRADEMARK OFFICE
CERTIFICATE OF CORRECTION

| | | |
|---|---|---|
| PATENT NO. | : 8,703,121 B2 | Page 1 of 1 |
| APPLICATION NO. | : 10/877445 | |
| DATED | : April 22, 2014 | |
| INVENTOR(S) | : Harris et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 722 days.

Signed and Sealed this
Eleventh Day of August, 2015

Michelle K. Lee
*Director of the United States Patent and Trademark Office*